US012797646B2

(12) United States Patent
Reo et al.

(10) Patent No.: US 12,797,646 B2
(45) Date of Patent: Nov. 17, 2026

(54) CATHETERS WITH BALLOONS ON WHICH ARE LOCATED ELECTRODES

(71) Applicant: Otsuka Medical Devices Co., Ltd., Tokyo (JP)

(72) Inventors: Michael L. Reo, Redwood City, CA (US); Stephen Bower, Morgan Hill, CA (US); Ashby Shaw, Santa Clara, CA (US); David Elliot Faulk, Jr., San Jose, CA (US)

(73) Assignee: Otsuka Medical Devices Co., Ltd., Tokyo (JP)

( * ) Notice: Subject to any disclaimer, the term of this patent is extended or adjusted under 35 U.S.C. 154(b) by 360 days.

(21) Appl. No.: 18/407,306

(22) Filed: Jan. 8, 2024

(65) Prior Publication Data

US 2024/0238620 A1 Jul. 18, 2024

Related U.S. Application Data

(60) Provisional application No. 63/480,208, filed on Jan. 17, 2023.

(51) Int. Cl.
*A61N 7/02* (2006.01)
*A61B 18/00* (2006.01)
(Continued)

(52) U.S. Cl.
CPC ........ *A61N 7/02* (2013.01); *A61B 2018/0022* (2013.01); *A61M 25/1018* (2013.01);
(Continued)

(58) Field of Classification Search
CPC ...... A61N 2007/0026; A61N 2007/003; A61B 2018/0022; A61B 5/6853; A61M 25/1018; A61M 25/1038
See application file for complete search history.

(56) References Cited

U.S. PATENT DOCUMENTS 4,469,100 A * 9/1984 Hardwick ......... A61M 25/1002 604/908
4,554,925 A 11/1985 Young
(Continued)

FOREIGN PATENT DOCUMENTS

EP 1299035 4/2003
EP 1503685 2/2005
(Continued)

OTHER PUBLICATIONS

Borchert, Bianca et al., "Lethal Atrioesophageal Fistual After Pulmonary Vein Isolation using High-Intensity Focused Ultrasound (HIFU)" J. Hrthm vol. 5, Issue 1, p. 145-148, Jan. 2008.
(Continued)

*Primary Examiner* — Sean W Collins
(74) *Attorney, Agent, or Firm* — Theresa Ann Raymer

(57) ABSTRACT

A catheter for use in analyzing neural activity of nerves that surround a biological lumen includes a handle and a shaft extending from the handle. The shaft configured to be inserted into the biological lumen. The selectively inflatable balloon is located on the shaft. The distal electrode and the proximal electrode are longitudinally spaced apart from one another on the shaft. Each of the distal electrode and the proximal electrode is configured to be selectively transitioned between a non-intussuscepted position and an intussuscepted position.

10 Claims, 23 Drawing Sheets

(51) Int. Cl.
*A61M 25/10* (2013.01)
*A61N 7/00* (2006.01)

(52) U.S. Cl.
CPC . *A61M 25/1038* (2013.01); *A61M 2205/3606* (2013.01); *A61M 2205/366* (2013.01); *A61M 2230/08* (2013.01); *A61N 2007/0026* (2013.01); *A61N 2007/003* (2013.01)

(56) References Cited

U.S. PATENT DOCUMENTS 4,643,186 A 2/1987 Rosen
4,650,466 A 3/1987 Luther
4,709,698 A 12/1987 Johnston et al.
4,841,977 A 6/1989 Griffith et al.
4,983,169 A 1/1991 Furukawa
5,000,185 A 3/1991 Yock
5,114,423 A 5/1992 Kasprzyk
5,368,591 A 11/1994 Lennox
5,391,197 A 2/1995 Burdette et al.
5,423,811 A 6/1995 Imran et al.
5,558,672 A 9/1996 Edwards et al.
5,575,788 A 11/1996 Baker et al.
5,657,755 A 8/1997 Desai
5,685,839 A 11/1997 Edwards et al.
5,688,266 A 11/1997 Edwards et al.
5,800,482 A 9/1998 Pomeranz et al.
6,066,134 A 5/2000 Eggers et al.
6,097,985 A 8/2000 Kasevich et al.
6,117,101 A 9/2000 Diederich et al.
6,254,598 B1 7/2001 Edwards
6,283,989 B1 9/2001 Laufer et al.
6,292,695 B1 9/2001 Webster
6,296,619 B1 10/2001 Brisken et al.
6,383,151 B1 5/2002 Diederich et al.
6,514,249 B1 2/2003 Maguire et al.
6,529,756 B1 3/2003 Phan
6,564,096 B2 5/2003 Mest
6,584,360 B2 6/2003 Francischelli et al.
6,635,054 B2 10/2003 Fjield et al.
6,648,883 B2 11/2003 Francischelli et al.
6,669,655 B1 12/2003 Acker
6,692,490 B1 2/2004 Edwards
6,719,755 B2 4/2004 Sliwa, Jr. et al.
6,763,722 B2 7/2004 Field et al.
6,837,886 B2 1/2005 Collins
6,845,267 B2 1/2005 Harrison et al.
6,954,977 B2 10/2005 Maguire
7,052,695 B2 5/2006 Kalish
7,156,816 B2 1/2007 Schwartz et al.
7,162,303 B2 1/2007 Levin et al.
7,371,231 B2 5/2008 Rioux et al.
7,510,536 B2 3/2009 Foley et al.
7,540,846 B2 6/2009 Harhen et al.
7,617,005 B2 11/2009 Demarais et al.
7,621,873 B2 11/2009 Owen et al.
7,653,438 B2 1/2010 Deem et al.
7,717,948 B2 5/2010 Demarais et al.
7,837,676 B2 11/2010 Sinelnikov et al.
7,942,871 B2 5/2011 Thapliyal et al.
8,024,050 B2 9/2011 Libbus et al.
8,025,688 B2 9/2011 Diederich et al.
8,137,274 B2 3/2012 Weng et al.
8,447,414 B2 5/2013 Johnson et al.
8,483,831 B1 7/2013 Hiavka et al.
8,626,300 B2 1/2014 Demarais et al.
8,702,619 B2 4/2014 Wang
8,774,913 B2 7/2014 Demarais et al.
8,790,281 B2 7/2014 Diederich et al.
8,818,514 B2 8/2014 Zarins et al.
8,845,629 B2 9/2014 Demarais et al.
8,932,289 B2 1/2015 Mayse et al.
9,022,948 B2 5/2015 Wang
9,028,472 B2 5/2015 Mathur et al.
9,066,720 B2 6/2015 Ballakur et al.
9,072,902 B2 7/2015 Mathur et al.
9,155,590 B2 10/2015 Mathur
9,186,198 B2 11/2015 Demarais et al.
9,186,212 B2 11/2015 Nabulovsky et al.
9,289,132 B2 3/2016 Ghaffari
9,326,816 B2 5/2016 Srivastava
9,327,123 B2 5/2016 Yamasaki
9,333,035 B2 5/2016 Rudie
9,339,332 B2 5/2016 Srivastava
9,345,530 B2 5/2016 Ballakur et al.
9,375,154 B2 6/2016 Wang
9,427,579 B2 8/2016 Fain et al.
9,439,598 B2 9/2016 Shimada et al.
9,649,064 B2 5/2017 Toth et al.
9,707,034 B2 7/2017 Schaer
9,723,998 B2 8/2017 Wang
9,730,639 B2 8/2017 Toth et al.
9,743,845 B2 8/2017 Wang
9,750,560 B2 9/2017 Ballakur et al.
9,770,291 B2 9/2017 Wang et al.
9,770,593 B2 9/2017 Gross
9,801,684 B2 10/2017 Fain
9,820,811 B2 11/2017 Wang
9,907,983 B2 3/2018 Thapliyal et al.
9,931,047 B2 4/2018 Srivastava
9,943,666 B2 4/2018 Warnking
9,956,034 B2 5/2018 Toth et al.
9,968,790 B2 5/2018 Toth et al.
9,981,108 B2 5/2018 Warnking
9,999,463 B2 6/2018 Puryear et al.
10,004,458 B2 6/2018 Toth et al.
10,004,557 B2 6/2018 Gross et al.
10,010,364 B2 7/2018 Harringtpm
10,016,233 B2 7/2018 Pike
10,016,579 B2 7/2018 Campbell et al.
10,022,085 B2 7/2018 Toth et al.
10,039,901 B2 8/2018 Warnking
10,123,903 B2 11/2018 Warnking et al.
10,143,419 B2 12/2018 Toth et al.
10,179,020 B2 1/2019 Ballakur et al.
10,179,026 B2 1/2019 Ng
10,182,865 B2 1/2019 Naga et al.
10,226,633 B2 3/2019 Toth et al.
10,245,429 B2 4/2019 Deem et al.
10,292,610 B2 5/2019 Srivastava
10,293,190 B2 5/2019 Zarins et al.
10,350,440 B2 7/2019 Taylor et al.
10,363,359 B2 7/2019 Toth et al.
10,368,775 B2 8/2019 Hettrick et al.
10,376,310 B2 8/2019 Fain et al.
10,383,685 B2 8/2019 Gross et al.
10,398,332 B2 9/2019 Min et al.
10,456,605 B2 10/2019 Taylor et al.
10,470,684 B2 11/2019 Toth et al.
10,478,249 B2 11/2019 Gross et al.
10,499,937 B2 12/2019 Warnking
10,543,037 B2 1/2020 Shah
10,850,091 B2 12/2020 Zarins et al.
11,801,085 B2 10/2023 Wu et al.
2001/0023365 A1 9/2001 Medhkour et al.
2002/0042610 A1 4/2002 Sliwa, Jr. et al.
2002/0072741 A1 6/2002 Sliwa, Jr. et al.
2002/0165535 A1 11/2002 Lesh
2002/0173724 A1 11/2002 Dorando et al.
2002/0193681 A1 12/2002 Vitek et al.
2003/0004439 A1 1/2003 Pant et al.
2003/0028111 A1 2/2003 Vaezy et al.
2003/0074039 A1 4/2003 Puskas
2003/0114878 A1 6/2003 Diederich et al.
2003/0125726 A1 7/2003 Maguire et al.
2003/0181963 A1 9/2003 Pellegrino et al.
2003/0216721 A1 11/2003 Diederich et al.
2003/0216792 A1 11/2003 Levin
2004/0019349 A1 1/2004 Fuimaono et al.
2004/0082859 A1 4/2004 Schaer
2004/0097819 A1 5/2004 Duarte
2004/0106880 A1 6/2004 Weng et al.
2004/0122494 A1 6/2004 Eggers et al.
2004/0181178 A1 9/2004 Aldrich et al.

(56) References Cited

U.S. PATENT DOCUMENTS

| | | | |
|---|---|---|---|
| 2004/0242999 | A1 | 12/2004 | Vitek et al. |
| 2005/0038340 | A1 | 2/2005 | Vaezy et al. |
| 2005/0159738 | A1 | 7/2005 | Visram et al. |
| 2005/0203501 | A1 | 9/2005 | Aldrich et al. |
| 2005/0215990 | A1 | 9/2005 | Govari |
| 2005/0228283 | A1 | 10/2005 | Gifford et al. |
| 2005/0228459 | A1 | 10/2005 | Levin et al. |
| 2005/0228460 | A1 | 10/2005 | Levin et al. |
| 2005/0261672 | A1 | 11/2005 | Deem et al. |
| 2005/0288730 | A1 | 12/2005 | Deem |
| 2006/0041277 | A1 | 2/2006 | Deem et al. |
| 2006/0052695 | A1 | 3/2006 | Adam et al. |
| 2006/0058711 | A1 | 3/2006 | Harhen et al. |
| 2006/0064081 | A1 | 3/2006 | Rosinko |
| 2006/0118127 | A1 | 6/2006 | Chinn |
| 2006/0142827 | A1 | 6/2006 | Willard et al. |
| 2006/0184069 | A1 | 8/2006 | Vaitekunas |
| 2006/0217772 | A1 | 9/2006 | Libbus et al. |
| 2006/0235286 | A1 | 10/2006 | Stone et al. |
| 2007/0060921 | A1 | 3/2007 | Janssen et al. |
| 2007/0072741 | A1 | 3/2007 | Robideau |
| 2007/0106292 | A1 | 5/2007 | Kaplan |
| 2007/0135875 | A1 | 6/2007 | Demarais et al. |
| 2008/0039746 | A1 | 2/2008 | Hissong et al. |
| 2008/0215031 | A1 | 9/2008 | Belfort et al. |
| 2009/0234407 | A1 | 9/2009 | Hastings et al. |
| 2009/0248005 | A1 | 10/2009 | Rusin et al. |
| 2011/0118723 | A1 | 5/2011 | Turner et al. |
| 2011/0125206 | A1 | 5/2011 | Bornzin |
| 2011/0208096 | A1 | 8/2011 | Demarais et al. |
| 2012/0004656 | A1 | 1/2012 | Jackson et al. |
| 2012/0265198 | A1 | 10/2012 | Crow et al. |
| 2012/0296232 | A1 | 11/2012 | Ng |
| 2012/0302996 | A1* | 11/2012 | Barash ................ A61M 25/104 604/509 |
| 2013/0023897 | A1 | 1/2013 | Wallace |
| 2013/0085489 | A1 | 4/2013 | Fain et al. |
| 2013/0096550 | A1 | 4/2013 | Hill |
| 2013/0116737 | A1 | 5/2013 | Edwards et al. |
| 2013/0123770 | A1 | 5/2013 | Smith |
| 2013/0131743 | A1 | 5/2013 | Yamasaki et al. |
| 2013/0150749 | A1 | 6/2013 | McLean et al. |
| 2013/0165925 | A1 | 6/2013 | Mathur et al. |
| 2013/0172872 | A1 | 7/2013 | Subramaniam |
| 2013/0274614 | A1 | 10/2013 | Shimada et al. |
| 2013/0289369 | A1 | 10/2013 | Margolis |
| 2013/0289682 | A1 | 10/2013 | Barman et al. |
| 2014/0018788 | A1 | 1/2014 | Engelman et al. |
| 2014/0058294 | A1 | 2/2014 | Gross et al. |
| 2014/0257271 | A1 | 9/2014 | Mayse et al. |
| 2014/0274614 | A1 | 9/2014 | Min et al. |
| 2014/0275924 | A1 | 9/2014 | Min et al. |
| 2014/0288551 | A1 | 9/2014 | Bharmi et al. |
| 2014/0288616 | A1 | 9/2014 | Rawat et al. |
| 2014/0303617 | A1 | 10/2014 | Shimada |
| 2014/0378967 | A1 | 12/2014 | Willard et al. |
| 2015/0265329 | A1* | 9/2015 | Lalonde ................ A61B 18/02 606/21 |
| 2015/0289931 | A1 | 10/2015 | Puryear et al. |
| 2016/0000345 | A1 | 1/2016 | Kobayashi et al. |
| 2016/0045121 | A1 | 2/2016 | Akingba et al. |
| 2016/0262833 | A1 | 9/2016 | Rudie |
| 2016/0324569 | A1 | 11/2016 | Hoitink et al. |
| 2017/0027460 | A1 | 2/2017 | Shimada et al. |
| 2017/0035310 | A1 | 2/2017 | Shimada et al. |
| 2017/0296264 | A1 | 10/2017 | Wang |
| 2017/0319853 | A1 | 11/2017 | Yamasaki et al. |
| 2017/0354461 | A1* | 12/2017 | Rothman ........... A61B 18/0206 |
| 2018/0022108 | A1 | 1/2018 | Mori et al. |
| 2018/0042670 | A1 | 2/2018 | Wang et al. |
| 2018/0064359 | A1 | 3/2018 | Pranaitis |
| 2018/0078307 | A1 | 3/2018 | Wang et al. |
| 2018/0185091 | A1 | 7/2018 | Toth et al. |
| 2018/0221087 | A1 | 8/2018 | Puryear et al. |
| 2018/0249958 | A1 | 9/2018 | Toth et al. |
| 2018/0250054 | A1 | 9/2018 | Gross et al. |
| 2018/0280082 | A1 | 10/2018 | Puryear et al. |
| 2018/0289320 | A1 | 10/2018 | Toth et al. |
| 2018/0310991 | A1 | 11/2018 | Pike |
| 2018/0333204 | A1 | 11/2018 | Ng |
| 2019/0046111 | A1 | 2/2019 | Toth et al. |
| 2019/0046264 | A1 | 2/2019 | Toth et al. |
| 2019/0076191 | A1 | 3/2019 | Wang |
| 2019/0110704 | A1 | 4/2019 | Wang |
| 2019/0134396 | A1 | 5/2019 | Toth et al. |
| 2019/0151670 | A1 | 5/2019 | Toth et al. |
| 2019/0183560 | A1 | 6/2019 | Ballakur et al. |
| 2019/0307361 | A1 | 10/2019 | Hettrick et al. |
| 2019/0366130 | A1 | 12/2019 | Sverdlik et al. |
| 2020/0046248 | A1 | 2/2020 | Toth et al. |
| 2020/0077907 | A1 | 3/2020 | Shimada et al. |

FOREIGN PATENT DOCUMENTS

| | | |
|---|---|---|
| EP | 1579889 | 9/2005 |
| EP | 2359764 | 8/2011 |
| EP | 2430996 | 3/2012 |
| EP | 2968984 | 1/2016 |
| EP | 2995250 | 3/2016 |
| EP | 3799931 | 4/2021 |
| WO | WO1999/002096 | 1/1999 |
| WO | WO2001/095820 | 12/2001 |
| WO | WO2002/005897 | 1/2002 |
| WO | WO 2002/019934 | 3/2002 |
| WO | WO2003/022167 | 3/2003 |
| WO | WO2003/051450 | 6/2003 |
| WO | WO2006/041881 | 4/2006 |
| WO | WO2006/060053 | 6/2006 |
| WO | WO2007/014003 | 2/2007 |
| WO | WO2010/080678 | 7/2010 |
| WO | WO2012/112165 | 8/2012 |
| WO | WO2014/062160 | 4/2014 |

OTHER PUBLICATIONS

Calkins, Hugh et al., "Temperature Monitoring During Radiofrequency Catheter Ablation Procedures Using Closed Loop Control," Circulation vol. 90, No. 3, p. 1279-1286, Sep. 1994.

Deardorff, Dana L. et al., "Control of interstitial thermal coagulation: Comparative evaluation of microwave and ultrasound applicators," Medical Physics vol. 28, No. 1, p. 104-117, Jan. 2001.

Dinerman, Jay L. et al., "Temperature Monitoring During Radiofrequency Ablation," Journal of Cardiovascular Electrophysiology, vol. 7 No. 2, p. 163-173, Feb. 1996.

Esler, Murray et al., "The future of renal denervation," Autonomic Neuroscience: Basic and Clinical, vol. 204, p. 131-138, May 2017.

Filonenko, E.A. et al., "Heating of Biological Tissues by Two-Dimensional Phased Arrays with Random and Regular Element Distributions," Acoustical Physics, vol. 50 No. 2, p. 222-231, 2004.

Fry, William J., "Action of Ultrasound on Nerve Tissue—A review," The Journal of the Acoustical Society of America, vol. 25 No. 1, p. 1-5, Jan. 1953.

Fry, Frank J., "Precision High Intensity Focusing Ultrasonic Machines for Surgery," High Intensity Focused U.S., 152-156, Sep. 6-7, 1957.

Haines, David, "Biophysics of Ablation: Application to Technology," Journal of Cardiovascular Electrophysiology, vol. 15, No. 10, p. S2-S11, Oct. 2004.

Hynynen, K. et al., "Design of Ultrasonic Transducers for Local Hyperthermia," Ultrasound in Med. & Biol., vol. 7, No. 4, p. 397-402, Feb. 1981.

Hynynen, K. et al., "Temperature measurements during ultrasound hyperthermia," Medical Physics vol. 16, No. 4, p. 618-626, Jul./Aug. 1989.

Jolesz, Ferenc A. et al., "MR Imaging—Controlled Focused Ultrasound Ablation: A Noninvasive Image-Guided Surgery," Magnetic Resonance Imaging Clinics of North America, vol. 13, Issue 3, p. 545-560, 2005.

Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.

(56) References Cited

OTHER PUBLICATIONS

Lafon, C. et al., "Design and Preliminary Results of an Ultrasound Applicator for Interstitial Thermal Coagulation," Ultrasound in Medicine & Biology, vol. 24, No. 1, p. 113-122, 1998.
Lewis, Matthew A. et al., "Thermometry and Ablation Monitoring with Ultrasound," Int. J. Hyperthermia vol. 31, Issue 2, p. 163-181, Mar. 2015.
Liu, Xinmeng et al., "Visualization and mapping of the right phrenic nerve by intracardiac echocardiography during atrial fibrillation ablation," Europace vol. 25, p. 1352-1360, 2023.
Mendelsohn, Farrell O., "Microanatomy of the Renal Sympathetic Nervous System," Endovascular Today, p. 59- 62, Oct. 2013.
Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.
Quadri, Syed A. et al., "High-intensity focused ultrasound: past, present, and future in neurosurgery," Neurosurgical Focus, vol. 44, No. 2, p. 1-9, Feb. 2018.
Ross, Anthony B. et al., "Highly directional transurethral ultrasound applicators with rotational control for MRI-guided prostatic thermal therapy," Physics in Medicine & Biology, vol. 49, p. 189-204, Jan. 2004.
Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.
Sanghvi, Kintur et al., "Rationale and design for studies of renal denervation in the absence (Spyral HTN Off-Med) and presence (Spyral HTN On-Med) of antihypertensive medications," American Heart Journal, vol. 180, p. e1-e2. Oct. 2016.
Satou, Shunsuke et al., "Observation of renal sympathetic nerves by intravascular ultrasound," Hypertension Research vol. 42, p. 1092-1094, 2019.
Schmidt, Boris et al., "Balloon Catheters for Pulmonary Vein Isolation," Herz vol. 33, p. 580-584, 2008.
Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.
Stauffer, P.R. et al., "13 Interstitial Heating Technologies," Thermoradiotherapy and Thermochemotherapy, p. 279-320, 1995.
Swanson, David K. et al., "Tissue temperature Feedback Control of Power, The Key to Successful Ablation," Innovations, vol. 6 No. 4, p. 276-282, Jul./Aug. 2011.
Tabei, Makoto et al., "A k-space method for coupled first-order acoustic propagation equations," J. Acoust. Soc. Am., vol. 111, No. 1, pt. 1, p. 53-63, Jan. 2002.
Tzafriri, Abraham R. et al., "Innervation Patterns May Limit Response to Endovascular Renal Denervation," Journal of the American College of Cardiology, vol. 64, No. 11, p. 1079-1087, Sep. 2014.
Umemura, Shin-ichiro, "Focused ultrasound transducer for thermal treatment," International Journal of Hyperthermia, vol. 31, No. 2, p. 216-221, 2015.
Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.
Zivin, Adam, et al., "Temperature Monitoring versus Impedance Monitoring during RF Catheter Ablation," Radiofrequency Catheter Ablation of Cardiac Arrhythmias, Basic Concepts and Clinical Applications, Second Edition, Edited by Shoei K. Stephen Huang, MD & David J. Wilber, MD, p. 103-112, 2000.
Accornero, Neri et al., "Selective Activation of Peripheral Nerve Fibre Groups of Different Diameter by Triangular Shaped Stimulus Pulses", J. Physiol. (1977), 273, 539-560, 22 Q9S.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).
American Heart Association—Pulmonary Hypertension: High Blood Pressure in the Heart-to-Lung System, (last reviewed Oct. 31, 2016).
Appeal Brief of Patent Owner from Reexamination 95-002, 110.
Aytac, et al., "Correlation Between the Diameter of the Main Renal Artery and the Presence of an Accessory Renal Artery", J Ultrasound Med 22:433-439, 2003 (.
Azizi, Michel et al., Ultrasound renal denervation for hypertension resistant to a triple medication pill (Radiance-HTN Trio): a randomised, multicentre, single-blind, sham-controlled trial, 397 Lancet 2476 (2021).
Bailey, M.R. et al., Physical Mechanisms of the Therapeutic Effect of Ultrasound (A Review), Acoustical Physics, vol. 49, No. 4, 2003, pp. 369-388.
Bengel, et al., Serial Assessment of Sympathetic Reinnervation After Orthotopic Heart Transplantation; A Longitudinal Study Using PET and C-11 Hydroxyephedrine, Circulation. 1999;99: 1866-1871.
Berjano, E. et al., "A Cooled Intraesophageal Balloom to Prevent Thermal Injury during Endocardial Surgical Radiofrequency Ablation of the left Atrium: a finite element study." Physics in Medicine and Biology, 50(20): 269-279, 2015.
Bhatt, D.L., et al., A Controlled Trial of Renal Denervation for Resistant Hypertension, New England J. Med., 370:1393-1401 (2014).
Bhatt, Deepak L. et al., Long-term outcomes after catheter-based renal artery denervation for resistant hypertension: final follow-up of the randomised Symplicity HTN-3 Trial, 400 Lancet 1405 (2022).
Billard, B.E. et al., Effects of Physical Parameters on High Temperature Ultrasound Hyperthermia, Ultrasound in Med. & Biol. vol. 16, No. 4, pp. 409-420, 1990.
Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).
Blanketjin, Peter, Sympathetic Hyperactivity in Chronic Kidney Disease, Neprhrol Dial Transplant, vol. 19, No. 6, 1354-1357 (2004).
Blum et al., Treatment of Ostial Renal-Artery Stenoses with Vascular Endoprostheses after Unsuccessful Balloon Angioplasty, N. Engl. J. Med. 336 459-65 (1997).
Bonsignore, C., "A Decade of Evolution in Stent Design", Proceedings of the International Conference on Shape Memory and Superelastic Technologies, (2003).
Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).
Bush, et al., "Endovascular revascularization of renal artery stenosis: Technical and clinical results", Journal of Vascular Surgery, May 2001, 1041-1049 (2001).
Camasao, D. B. et al., The mechanical characterization of blood vessels and their substitutes in the continuous quest for physiological-relevant performances: A critical review, Materials Today Bio, vol. 10 (2021).
Carter, J., "Microneurography and Sympathetic Nerve Activity: A Decade-By-Decade Journey across 50 Years," Journal of Neurophysiology, vol. 121, No. 4. doi: 10.1 152/jn.00570.2018.
Carter, Stefan et al., Measurement of Renal Artery Pressures by Catheterization in Patients with and without Renal Artery Stenosis, Circulation, vol. XXXIII, 443-449 (1966).
Chapelon, J.Y., "Treatment of Localised Prostate Cancer with Transrectal High Intensity Focused Ultrasound," European Journal of Ultrasound 9, 31-38, 1999.
Charlesworth, Peter et al., Renal Artery Injury from a Fogarty Balloon Catheter, Journal of Vascular Surgery, vol. 1, No. 4, 573-576 (1984).
Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Chiesa et al., Endovascular Stenting for the Nutcracker Phenomenon, J. Endovasc. Ther., 8:652-655 (2001).

(56) References Cited

OTHER PUBLICATIONS

Corrected Patent Owner's Response to Office Action, dated May 10, 2013, from File History of Inter Partes Reexamination U.S. Appl. No. 95/002,110.
Dangas, G., et al., Intravascular Ultrasound—Guided Renal Artery Stenting, J Endovasc Ther, 2001;8:238-247 (2001).
Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).
Deardorff, Dana et al., Ultrasound Applicators with Internal Cooling for Interstitial Thermal Therapy, SPIE vol. 3594, 36-46, Jan. 1999.
Declaration of Chris Daft dated Jan. 11, 2022, in the Patent Trial and Appeal Board, United States Patent and Trademark Office, Petition No. PTAB-IPR2022-00431.
Second Declaration of Chris Daft. Dated Jan. 10, 2023, in the Patent Trial and Appeal Board, United States Patent and Trademark Office, Petition No. PTAB-IPR2022-00431.
Declaration of Dr. Daniel van der Weide, dated Oct. 26, 2022, in the Patent Trial and Appeal Board, United States Patent and Trademark Office, Petition No. PTAB-IPR2022-00431.
Declaration of Dr. Dieter Haemmerich, dated Aug. 29, 2012, in the Patent Trial and Appeal Board, United States Patent and Trademark Office, In re U.S. Pat. No. 7,717,948.
Declaration of Dr. John M. Moriarty in German Nullity proceedings for EP2261905 dated Jul. 13, 2022.
Declaration of Dr. John Moriarty, dated Jan. 19, 2023, in the Patent Trial and Appeal Board, United States Patent and Trademark Office, Petition No. PTAB-IPR2022-00431.
Declaration of Jonathan Bradford in Support of Patent Owner's Response, dated Oct. 27, 2022.
Declaration of Jonathan Bradford dated May 10, 2022, in the Patent Trial and Appeal Board, United States Patent and Trademark Office, Petition No. PTAB-IPR2022-00431.
Declaration of Dr. Michael Bohm dated Sep. 29, 2022 on behalf of Medtronic Inc.
Declaration of Dr. Robert Tucker, dated Oct. 27, 2022, in the Patent Trial and Appeal Board, United States Patent and Trademark Office, Petition No. PTAB-IPR2022-00431.
Declaration of Farrell Mendelsohn dated Jan. 10, 2022, in the Patent Trial and Appeal Board, United States Patent and Trademark Office, Petition No. PTAB-IPR2022-00431.
Defendant's Reply to Court Order of Oct. 4, 2022 and Plaintiff's Surrejoinder of Sep. 29, 2022 in the Mannheim District Court, case No. 7 O 14/21, dated Oct. 31, 2022.
Defendant's Response dated May 11, 2022 in the Munich Federal Patent Court, Nullity Suit 6 Ni 32/22.
Dibona, Gerald F., "Neural Control of the Kidney, Past, Present and Future," 41 [Part II] Hypertension 621 24 (2003).
Dibona, Gerald, Sympathetic Nervous System and Kidney in Hypertension, Current Opinion in Nephrology and Hypertension, vol. 11, 197-200 (2002).
Dibona, Gerald F. et al., "Neural Control of Renal Function", 77 Physiological Reviews No. 1, 75 (1997).
Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.
Diederich, et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.
Diedrich, A. et al., "Analysis of Raw Microneurographic Recordings Based on Wavelet De-Noising Technique and 1 Classification Algorithm: Wavelet Analysis in Microneurography," IEEE Trans Biomed Eng. Jan. 2003; 50(1): 41-50_doi:10.1109fTBME.2002.807323.
Draney, Mary et al., Three-Dimensional Analysis of Renal Artery Bending Motion During Respiration, International Society of Endovascular Specialists, vol. 12, 380-386 (2005).
Erikson, Kenneth et al., Ultrasound in Medicine: A Review, IEEE Transactions on Sonics and Ultrasonics, vol. 21, No. 3 (1974).
EP Board of Appeals Communication dated Dec. 17, 2019—Preliminary Remarks for EP appeal No. T2680/16-3.3.4.01.
European Search Report in Application No. 12180431.4 dated Jan. 17, 2013.
European Communication in Application No. 12180431.4 dated Oct. 23, 2013.
European Patent No. 12167931, Claims of the Main Request dated Sep. 30, 2016.
European Search Report (Supplementary) in Application No. 14775754.6 dated Feb. 17, 2016.
European Search Report in Application No. 218186547 dated Nov. 19, 2018.
European Search Report in Application No. 20202272.9 dated Mar. 1, 2021.
Fan, Xiaobing et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.
Fengler, Karl et al., A Three-Arm Randomized Trial of Different Renal Denervation Devices and Techniques in Patients with Resistant Hypertension (RADIOSOUND-HTN), 139 Circulation 590 (2019).
Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.
Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).
Gervais, Debra A. et al., Radiofrequency ablation of renal cell carcinoma: Part 2, Lessons learned with ablation of 100 tumors, 185 AJR Am. J. Roentgenol. 72 (2005).
Goldberg, S. Nahum et al., EUS-guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Gorsich, W., et al., Heat-Induced Contraction of Blood Vessels, Lasers in Surgery and Medicine, 2:1-13 (1982).
Gray, Henry, Gray's Anatomy: The Anatomical Basis of Medicine and Surgery, Churchill Livingstone, New York, NY (1995).
Habict, Antje et al., Sympathetic Overactivity and Kidneys, The Middle European Journal of Medicine, vol. 115, 634-640 (2003).
Hansen et al., The Transplanted Human Kidney Does Not Achieve Functional Reinnervation, 87 Clinical Science 13 (1994).
Harrison, R. R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.
He, D. S. et al., Application of Ultrasound Energy for Intracardiac Ablation of Arrhythmias, European Heart Journal, vol. 16, 961-966 (1995).
Heffner, H. et al., "Gain, Band Width, and Noise Characteristics of the Variable-Parameter Amplifier," Journal of Applied Physics, vol. 29, No. 9, Sep. 1958, 1 1 pages.
Holmes, David R. et al., Pulmonary vein stenosis complicating ablation for atrial fibrillation: clinical spectrum and interventional considerations, 2 JACC Cardiovasc. Interv. 267 (2009).
Hsu, Thomas H. S. et al., Radiofrequency ablation of the kidney: acute and chronic histology in porcine model, 56 Urology 872 (2000).
Huang, S.K.S. and Wilbur, D. Eds, Radiofrequency Catheter Ablation of Cardiac Arrhythmias, Basic Concepts and Clinical Applications, Futura Publishing Company, Inc., Armonk, New York (2000).
Huang, et al., Renal Denervation Prevents and Reverses Hyperinsulinemia-Induced Hypertension in Rats, Hypertension 32 (1998) pp. 249-254.

(56) References Cited

OTHER PUBLICATIONS

Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.
Isles et al., Management of Renovascular Disease: A Review of Renal Artery Stenting in Ten Studies, QJM 92, 159-67 (1999).
Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.
Janssen, B. J. A., et al. "Renal nerves in hypertension." Miner Electrolyte Metab., 15:74-82 (1989).
Janzen, Nicolette et al., Minimally Invasive Ablative Approaches in the Treatment of Renal Cell Carcinoma, Current Urology Reports, vol. 3 (2002).
Kaltenbach, Benjamin et al., Renal Artery Stenosis After Renal Sympathetic Denervation, Journal of the American College of Cardiology, vol. 60, No. 25 (2012).
Kapural, Leonardo, et al., "Radiofrequency Ablation for Chronic Pain Control," Anesthetic Techniques in Pain Management, pp. 517-525, 2001.
Katholi, R.E., et al., Importance of Renal Sympathetic Tone in the Development of DOCA-Salt Hypertension in The Rat, Hypertension, 2:266-273 (1980).
Kim, Yun-Hyeon et al., Pulmonary vein diameter, cross-sectional area, and shape: CT analysis, Radiology Society of North America, vol. 235, No. 1, 49-50 (2005).
Kirsh, Danielle, Balloon Catheters: What are some key design considerations?, Massdevice (Dec. 6, 2016).
Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).
Koomans, Hein et al., Sympathetic Hyperactivity in Chronic Renal Failure: A wake-up call, Frontiers in Nephrology, vol. 15, 524-537 (2004).
Kuo, et al., "Atrial Fibrillation: New Horizons", Chang Gung Med J vol. 26 No. 10 Oct. 2003.
Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).
Lee, Jong Deok et al., MR imaging-histopathologic correlation of radiofrequency thermal ablation lesion in a rabbit liver model: observation during acute and chronic stages, 2 Korean J. Radiol. 151 (2001).
Levin, S., et al., ARDIAN: Succeeding Where Drugs Fail—Treating Hypertension in the Cath Lab, In Vivo, 27:23 (2009).
Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).
Marine, Joseph E., Catheter ablation therapy for supraventricular arrhythmias, 298 JAMA 2768 (2007).
Martin, Louis K. et al., Long-term Results of Angioplasty in 110 Patients with Renal Artery Stenosis, Journal of Vascular and Interventional Radiology, vol. 3, No. 4, 619-626 (1992).
Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.
Matsumoto, Edward D. et al., Short-term efficacy of temperature-based radiofrequency ablation of small renal tumors, 65 Urology 877 (2005).
Medtronic Press Release, Medtronic Announces U.S. Renal Denervation Pivotal Trial Fails to Meet Primary Efficacy Endpoint While Meeting Primary Safety Endpoint (Jan. 9, 2014).
Medtronic Inc., Renal Denervation (RDN): Novel Catheter-Based Treatment for Hypertension, Scientific Background, 2011.
Medtronic Inc., The Symplicity RDN System, 2012.
Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).
Millard, et al., Renal Embolization for Ablation of Function In Renal Failure And Hypertension, Postgraduate Med. J. 65, 729-734 (1989).
Mitchell, et al., "The Renal Nerves" British Journal of Urology, Read by invitation at the Sixth Annual Meeting of the British Association of Urological Surgeons on Jun. 30, 1950.
Morrissey, D. M. "Sympathectomy in the treatment of hypertension." Lancet, CCLXIV:403-408 (1953).
Nair et al., "The Need for and the Challenges of Measuring Renal Sympathetic Nerve Activity," Heart Rhythm 2016; 13:1166-1171.
Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).
Netter, Frank, Atlas of Human Anatomy, Icon Learning Systems, Rochester, NY (2002).
Neumann, Jutta, Sympathetic hyperactivity in chronic kidney disease: Pathogenesis, clinical relevance, and treatment, International Society of Nephrology, vol. 65, 1568-1576 (2004).
News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.
Notice of Deposition of Tucker, filed Dec. 30, 2022 in the Patent Trial and Appeal Board, United States Patent and Trademark Office, Petition No. PTAB-IPR2022-00431.
Notice of Deposition of van der Weide, filed Dec. 30, 2022 in the Patent Trial and Appeal Board, United States Patent and Trademark Office, Petition No. PTAB-IPR2022-00431.
Notice re filing date accorded, dated Feb. 10, 2022 in the Patent Trial and Appeal Board, United States Patent and Trademark Office, Petition No. PTAB-IPR2022-00431.
Nozawa, T., et al. "Effects of long-term renal sympathetic denervation on heart failure after myocardial infarction in rats." Heart Vessels, 16:51-56 (2002).
Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").
Olsson, R. et al., "A Three-Dimensional Neural Recording Microsystem with Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.
Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.
Order Setting Oral Hearing 37 C.F.R. § 42.70, dated Mar. 24, 2023 in the Patent Trial and Appeal Board, United States Patent and Trademark Office, Petition No. PTAB-IPR2022-00431.
Page, Irvine H. & George J. Heuer, The Effect of Renal Denervation on the Level of Arterial Blood Pressure and Renal Function in Essential Hypertension, 14 J. Clinical Investigation 27 (1935) (received for publication in 1934).
Page, Irvine H. & George J. Heuer, The Effect of Renal Denervation on Patients Suffering from Nephritis, 14 J. Clinical Investigation 443 (1935) (received for publication in 1935).
Papademetriou, Vasilios et al., Renal Sympathetic Denervation for the Treatment of Difficult-to-Control or Resistant Hypertension, 2011 Int. J. Hypertension, Article 196518 (2011).
Papademetriou, et al., "Renal Sympathetic Denervation: Hibernation or Resurrection?", Cardiology 2016; 135, 11 pgs.
Papadopoulos, N., "Evaluation of a Small Flat Rectangular Therapeutic Ultrasonic Transducer Intended for Intravascular Use," Ultrasonics 74, 196-203, 2017.

(56) References Cited

OTHER PUBLICATIONS

Pappone C, et al., "Circumferential radiofrequency ablation of pulmonary vein ostia: a new anatomic approach for curing atrial fibrillation", Circulation. 2000; 102(21):2619-2628. (2000).
Patent Owner's Mandatory Notice, filed Feb. 3, 2022 in the Patent Trial and Appeal Board, United States Patent and Trademark Office, Petition No. PTAB-IPR2022-00431.
Patent Owner's Notice of Deposition of Dr. Chris Daft, filed Sep. 20, 2022 in the Patent Trial and Appeal Board, United States Patent and Trademark Office, Petition No. PTAB-IPR2022-00431.
Patent Owner's Notice of Deposition of Dr. Chris Daft filed Feb. 21, 2023 in the Patent Trial and Appeal Board, United States Patent and Trademark Office, Petition No. PTAB-IPR2022-00431.
Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.
Patent Owner's Notice of Deposition of Dr. John Moriarty, filed Feb. 21, 2023 in the Patent Trial and Appeal Board, United States Patent and Trademark Office, Petition No. PTAB-IPR2022-00431.
Patent Owner's Objections to Evidence, filed Aug. 18, 2022 in the Patent Trial and Appeal Board, United States Patent and Trademark Office, Petition No. PTAB-IPR2022-00431.
Patent Owner's Power of Attorney, filed Feb. 3, 2022 in the Patent Trial and Appeal Board, United States Patent and Trademark Office, Petition No. PTAB-IPR2022-00431.
Patent Owner Medtronic Ireland Power of Attorney, filed May 10, 2022 in the Patent Trial and Appeal Board, United States Patent and Trademark Office, Petition No. PTAB-IPR2022-00431.
Patent Owner's Preliminary Response, filed May 10, 2022 in the Patent Trial and Appeal Board, United States Patent and Trademark Office, Petition No. PTAB-IPR2022-00431.
Patent Owner's Request for Oral Hearing, filed Mar. 23, 2023 in the Patent Trial and Appeal Board, United States Patent and Trademark Office, Petition No. PTAB-IPR2022-00431.
Patent Owner's Response, filed Oct. 27, 2022 in the Patent Trial and Appeal Board, United States Patent and Trademark Office, Petition No. PTAB-IPR2022-00431.
Patent Owner's Sur-Reply, filed Mar. 9, 2023 in the Patent Trial and Appeal Board, United States Patent and Trademark Office, Petition No. PTAB-IPR2022-00431.
Patent Owner's Updated Mandatory Notice, filed May 10, 2022 in the Patent Trial and Appeal Board, United States Patent and Trademark Office, Petition No. PTAB-IPR2022-00431.
Peet, M.M., Hypertension and Its Surgical Treatment by Bilateral Supradiaphragmatic Splanchnicectomy, Am. J. Surgery, LXXV:48-68 (1948).
Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.
Petitioner's Power of Attorney for Otsuka Medical Devices Co., Ltd., filed Jan. 13, 2022 in the Patent Trial and Appeal Board, United States Patent and Trademark Office, Petition No. PTAB-IPR2022-00431.
Petitioner's Power of Attorney for Recor Medical, Inc., filed Jan. 13, 2022 in the Patent Trial and Appeal Board, United States Patent and Trademark Office, Petition No. PTAB-IPR2022-00431.
Petitioner Reply, filed Jan. 23, 2023 in the Patent Trial and Appeal Board, United States Patent and Trademark Office, Petition No. PTAB-IPR2022-00431.
Petitioners' Request for Oral Argument, filed Mar. 21, 2023 in the Patent Trial and Appeal Board, United States Patent and Trademark Office, Petition No. PTAB-IPR2022-00431.
Petitioners' Updated Mandatory Notices, dated Jan. 18, 2022 in the Patent Trial and Appeal Board, United States Patent and Trademark Office, Petition No. PTAB-IPR2022-00431.
Plaintiff's Nullity Brief, dated Jan. 14, 2022, in the Munich Federal Patent Court, Nullity Suit 6 Ni 32/22.
Plaintiff's Reply to the May 11, 2022 Response, dated Jul. 18, 2022, in the Munich Federal Patent Court, Nullity Suit 6 Ni 32/22.
Plaintiff's Response to Court Order disagreeing with Stay of Proceedings dated Oct. 28, 2022 in Mannheim District Court, Infringement suit 7 O 147/21.
Plaintiff's Technical Brief dated Sep. 29, 2022 in the Mannheim District Court, Infringement suit 7 O 147/21.
Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).
Prochnau, Dirk et al., Catheter-based renal denervation for drug-resistant hypertension by using a standard electrophysiology catheter, EuroIntervention, vol. 7, 1077-1080 (2012).
Pugsley, et al., The vascular system: An overview of structure and function, Journal of Pharmacological and Toxicological Methods 44 (2000) 333-340.
Pürerfellner, Helmut et al., Incidence, Management and Outcome in Significant Pulmonary Vein Stenosis Complicating Ablation for Atrial Fibrillation, 93 Am. J. Cardiol. 1428 (2004).
Pürerfellner, Helmut & Martinek, Martin, Pulmonary vein stenosis following catheter ablation of atrial fibrillation, 20 Curr. Opin. Cardiol. 484 (2005).
Reaz, M.B.I., et al., "Techniques of EMG signal analysis: detection, processing, classification and applications," Biological Procedures Online, Jan. 2006, 25 pages.
Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.
Romanes, G.J., Cunningham's Textbook of Anatomy (11th ed. 1972).
Ryan, Steve, What are the Risks Associated with a Pulmonary Vein Ablation Procedure?, Atrial Fibrillation: Resources for Patients (last accessed Oct. 18, 2022).
Ryan, Thomas et al., Proceedings of Thermal Treatment of Tissue with Image Guidance, Progress in Biomedical Optics, vol. 3594 (1999).
Ryan, Thomas P., Thermal Treatment of Tissue with Image Guidance; Ultrasound Catheters For Circumferential Cardiac Ablation 1999.
Sakakura, Kenichi et al., Anatomic Assessment of Sympathetic Peri-Arterial Renal Nerves in Man, Journal of the American College of Cardiology, vol. 64, No. 7, 635-643 (2014).
Salmanpour, A., L. J. Brown and J. K. Shoemaker, "Detection of Single Action Potential in Multi-Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP. 2010.5495604.
Sánchez-Quintana, Damian et al., How close are the phrenic nerves to cardiac structures? Implications for cardiac interventionalists, 16 J. Cardiovasc. Electrophysiol 309 (2005) ("Sánchez-Quintana").
Schlaich, M.P. et al., "Renal Denervation: A Potential New Treatment Modality for Polycystic Ovary Syndrome," Journal of Hypertension, vol. 29, No. 5, pp. 991-996 201 1 . doi:10.1097/HJH. 0b013e328344db3a.
Schmieder, Ronald E., Renal denervation in patients with chronic kidney disease: current evidence and future perspectives, Nephrol. Dial. Transplant. gfac189 (2022).
Schneider, Peter, Endovascular Skills: Guidewire and Catheter Skills for Endovascular Surgery, 2nd ed., Marcel Dekker, Inc., New York, NY (2003).
Schneider, Peter A., Endovascular Skills, Quality Medical Publishing, Inc., 1998 ("Schneider").
Schmidt, Boris, et al., "Pulmonary Vein Isolation by High Intensity Focused Ultrasound," Indian Pacing and Electrophysiology Journal, pp. 126-133 (2006).
Selected documents from the File History of Inter Partes Reexamination U.S. Appl. No. 95/002,110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.

(56) References Cited

OTHER PUBLICATIONS

Shimizu, Kazumasa et al., Sympathetic Dysfunction in Heart Failure, Bailliere's Clinical Endocrinology and Metabolism, vol. 7, No. 2 (1993).
Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").
Slide deck from Medtronic Circulatory System Devices Panel Meeting, General Issues Panel: Clinical Evaluation of Anti-Hyperintensive Devices (Dec. 5, 2018).
Smithwick, R. H., et al., "Splanchnicectomy for essential hypertension." J. Am. Med. Assoc., 152:1501-1504 (1953).
Stella, A., et al. "Effects of reversible renal denervation on haemodynamic and excretory functions of the ipsilateral and contralateral kidney in the cat." J Hypertension, 4: 181-188 (1986)("Stella").
Stipulation Modifying Schedule, dated Dec. 30, 2022 in the Patent Trial and Appeal Board, United States Patent and Trademark Office, Petition No. PTAB-IPR2022-00431.
Stipulation Modifying Schedule, dated Feb. 16, 2023 in the Patent Trial and Appeal Board, United States Patent and Trademark Office, Petition No. PTAB-IPR2022-00431.
Stoeckel, D. et al., A Survey of Stent Designs, Min Invas Ther & Allied Technol 2002: 11(4) 137-147 (2002).
Swartz, John F. et al., Radiofrequency Endocardial Catheter Ablation of Accessory Atrioventricular Pathway Atrial Insertion Sites, 87 Circulation 487 (1993).
Tank, J. et al., "Spike Rate of Multi-Unit Muscle Sympathetic Nerve Fibers Following Catheter-Based Renal Nerve Ablation," J Am. Soc Hypertens, Oct. 2015; 9(10): 794-801. doi:10.1016/j.jash.2015.07.012.
Tanaka, Kazushi et al., "A New Radiofrequency Thermal Balloon Catheter for Pulmonary Vein Isolation," Journal of the American College of Cardiology vol. 38, No. 7, 2001.
Teigen et al., Segmental Renal Artery Embolization for Treatment of Pediatric Renovascular Hypertension, J. Vasco Interv. Radiol. 3, 111-7 (1992).
Thatipelli, Mallik R., et al., CT angiography of renal artery anatomy for evaluating embolic protection devices, 18 J. Vasc. Interv. Radiol. 842 (2007).
The Doctors and Experts at WebMD, Webster's New World Medical Dictionary (3rd ed. 2008) ("WebsterMD").
Transcript of the Mar. 2, 2023 deposition of Dr. John Moriarty.
Transcript of the Mar. 3, 2023 deposition of Dr. Chris Daft.
Transcript of deposition of the Jan. 1, 2023 deposition of Dr. Robert Tucker.
Transcript of the Jan. 14, 2023 deposition of Dr. Daniel van der Weide.
Transcript of the Sep. 30, 2022 deposition of Dr. Chris Daft.
Transcript of the Oct. 1, 2022 deposition of Dr. Farrell Mendelsohn.
Tsao, Hsuan-Ming et al., Evaluation of Pulmonary Vein Stenosis after Catheter Ablation of Atrial Fibrillation, 6 Card. Electrophysiol. Rev. 397 (2002).
Turner, et al., "Initial Experience Using the Palmaz Corinthian Stent for Right Ventricular Outflow Obstruction in Infants and Small Children", Catheterization and Cardiovascular Interventions 51:444-449 (2000).
Uchida, et al., "Effect of radiofrequency catheter ablation on parasympathetic denervation: A comparison of three different ablation sites." Pace, 21 :2517-2521 (1998).
Ulmsten, Ulf et al., "The Safety and Efficacy of MenoTreatTM, a new balloon device for thermal endometrial ablation," Acta Obstet Gynecol Scand 2001; 80: 52-57.
Vaezy, Shahram et al., Image-Guided Acoustic Therapy, Annual Review Biomedical Engineering, vol. 3, 375-390 (2001).
Valente, John F. et al., Laparoscopic renal denervation for intractable ADPKD-related pain, 16 Nephrol. Dial. Transplant. 160 (2001).
Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").
Wanchoo, Nishey, Medtronic Gets European and Australian Approval for Symplicity Spyral Multi-Electrode Renal Denervation Catheter, Medgadget (2013).
Weinstock, Marta et al., "Renal Denervation Prevents Sodium Retention and Hypertension in Salt-Sensitive Rabbits with Genetic Baroreflex Impairment", 90 Clinical Science 287 (1996).
Xu, J. et al., "A Bidirectional Neuromodulation Technology for Nerve Recording and Stimulation, Micromachines," vol. 9, 1 1 538. Oct. 23, 2018. doi:10.3390/mi9110538.
Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.
Zazgornik, "Bilateral Nephrectomy: The best, but often overlooked, treatment for refractory hypertension in hemodialysis patients," Am. J. Hypertension, 11:1364-1370 (1998).
Ziegler et al., Sources of Urinary Catecholamines in Renal Denervated Transplant Recipients, 8 J. Hypertension No. 10, 927 (1990).
U.S. Appl. No. 17/453,636, filed Nov. 4, 2021, File History.
U.S. Appl. No. 11/532,814, Non-Final Office Action mailed Mar. 29, 2012.
U.S. Appl. No. 14/683,966, Non-Final Office Action mailed Jun. 12, 2017, 14 pgs.
U.S. Appl. No. 14/683,966, Response filed Nov. 10, 2017 to Non-Final Office Action mailed Jun. 12, 2017, 13 pgs.
U.S. Appl. No. 14/683,966, Notice of Allowance mailed Jan. 31, 2018, 8 pgs.
U.S. Appl. No. 14/683,966, PTO Response to Rule 312 Communication mailed Mar. 29, 2018, 2 pgs.
U.S. Appl. No. 14/683,966, 312 Amendment filed Mar. 13, 2018, 10 pgs.
U.S. Appl. No. 14/683,966, Corrected Notice of Allowance mailed May 22, 2018, 4 pgs.
U.S. Appl. No. 15/204,349, Preliminary Amendment filed Nov. 30, 2016, 3 pgs.
U.S. Appl. No. 15/204,349, Restriction Requirement mailed May 17, 2018, 7 pgs.
U.S. Appl. No. 15/204,349, Response filed Jun. 5, 2018 to Restriction Requirement mailed May 17, 2018, 7 pgs.
U.S. Appl. No. 15/204,349, Non-Final Office Action mailed Nov. 27, 2018, 14 pgs.
U.S. Appl. No. 15/204,349, Response filed Feb. 27, 2019 to Non-Final Office Action mailed Nov. 27, 2018, 10 pgs.
U.S. Appl. No. 15/204,349, Final Office Action mailed Apr. 22, 2019, 16 pgs.
U.S. Appl. No. 15/204,349, Response filed Jun. 24, 2019 to Final Office Action mailed Apr. 22, 2019, 12 pgs.
U.S. Appl. No. 15/204,349, Advisory Action mailed Jul. 9, 2019, 5 pgs.
U.S. Appl. No. 15/261,732, Notice of Allowance dated Sep. 25, 2018.
U.S. Appl. No. 15/299,694, Restriction Requirement mailed Aug. 6, 2018, 6 pgs.
U.S. Appl. No. 15/299,694, Response filed Oct. 8, 2018 to Restriction Requirement mailed Aug. 6, 2018, 7 pgs.
U.S. Appl. No. 15/299,694, Non-Final Office Action mailed Nov. 27, 2018, 15 pgs.
U.S. Appl. No. 15/299,694, Response filed Feb. 27, 2019 to Non-Final Office Action mailed Nov. 27, 2018, 10 pgs.
U.S. Appl. No. 15/299,694, Final Office Action mailed Apr. 22, 2019, 16 pgs.
U.S. Appl. No. 15/299,694, Response filed Jun. 24, 2019 to Final Office Action mailed Apr. 22, 2019, 11 pgs.
U.S. Appl. No. 15/299,694, Advisory Action mailed Jul. 9, 2019, 5 pgs.
U.S. Appl. No. 15/943,354, Preliminary Amendment filed Apr. 3, 2018, 9 pgs.
U.S. Appl. No. 15/943,354, Restriction Requirement mailed Nov. 20, 2019, 8 pages.

(56) References Cited

OTHER PUBLICATIONS

U.S. Appl. No. 15/943,354, Response filed Dec. 19, 2019 to Restriction Requirement mailed Nov. 20, 2019, 8 pages.
U.S. Appl. No. 15/943,354, Non-Final Office Action mailed Jan. 13, 2020, 6 pages.
U.S. Appl. No. 15/943,354, Non-Final Office Action mailed Apr. 20, 2020, 7 pages.
U.S. Appl. No. 15/996,978, Preliminary Amendment filed Jun. 5, 2018, 11 pgs.
U.S. Appl. No. 15/996,978, Restriction Requirement mailed Feb. 7, 2020, 7 pages.
U.S. Appl. No. 15/996,978, Response filed Apr. 6, 2020 to Restriction Requirement mailed Feb. 7, 2020, 8 pages.
U.S. Appl. No. 15/996,978, Restriction Requirement mailed Apr. 16, 2020, 8 pages.
U.S. Appl. No. 15/996,978, Response filed May 1, 2020 to Restriction Requirement mailed Apr. 16, 2020, 8 pgs.
U.S. Appl. No. 15/996,978, Non-Final Office Action mailed Jun. 11, 2020, 8 pages.
U.S. Appl. No. 16/219,874, Final Office Action mailed Dec. 21, 2020, 7 pages.
U.S. Appl. No. 16/517,180, Preliminary Amendment filed Jul. 19, 2019, 12 pgs.
U.S. Appl. No. 17/453,636, filed Nov. 4, 2021.
Final Office Action dated Feb. 19, 2021, U.S. Appl. No. 15/996,978, filed Jun. 4, 2018.
Final Office Action dated Jun. 16, 2021, U.S. Appl. No. 15/996,978, filed Jun. 4, 2018.
Non-Final Office Action dated Sep. 2, 2021, U.S. Appl. No. 15/996,978, filed Jun. 4, 2018.
Notice of Allowance dated Oct. 6, 2021, U.S. Appl. No. 15/996,978, filed Jun. 4, 2018.
Response to Office Action dated May 18, 2021, U.S. Appl. No. 15/996,978, filed Jun. 4, 2018.
Response to Office Action dated Jul. 20, 2021, U.S. Appl. No. 15/996,978, filed Jun. 4, 2018.
Response to Office Action dated Sep. 22, 2021, U.S. Appl. No. 15/996,978, filed Jun. 4, 2018.
Ahmed, Muneeb et al., "Thermal Ablation Therapy for Hepatocellular Carcinoma," J. Vasc. Interv, Radiol., vol. 13, No. 9 pt. 2, 2002.
Benito, Fernando et al., "Radiofrequency catheter ablation of accessory pathways in infants," Heart, vol. 78, p. 160-162, 1997.
Chang, Isaac A. et al., "Thermal Modeling of Lesion Growth with Radiofrequency Ablation Devices," Biomedical Engineering Online vol. 3, p. 27, 2004.
Chung, Andrew et al., "Thermal dosimetry of a focused ultrasound beam in vivo by magnetic resonance imaging," Medical Physics, vol. 26, No. 9, p. 2017-2026, Sep. 1999.
Damianou, Christakis et al., "High Intensity Focused Ultrasound Ablation of Kidney Guided MRI," Ultrasound in Med. & Biol., vol. 30, No. 3, p. 397-404, 2004.
Deardorff, Dana L. et al., "Axial Control of Thermal Coagulation Using a Multi-Element Interstitial Ultrasound Applicator with Internal Cooling," IEE Transactions on Ultrasonics, Ferroelectrics, and Frequency Control, vol. 47, No. 1, p. 170-178, Jan. 2000.
Dewhirst, M.W. et al., "Basic Principles of Thermal Dosimetry and Thermal Thresholds for Tissue Damage from Hyperthermia," International Journal of Hyperthermia vol. 19, No. 3, p. 267-294, May-Jun. 2003.
Diederich, Chris J. et al., "Ultrasound Technology for Hyperthermia," Ultrasound in Med. & Biol., vol. 25, No. 6, p. 871-887, 1999.
Fry, F.J. et al., "Production of Reversible Changes in the Central Nervous System by Ultrasound," Science, vol. 127, p. 83-84, Jan. 1958.
Gavrilov, L.R., "Use of Focused Ultrasound for Stimulation of Nerve Structures," Ultrasonics, p. 132-138, May 1984.
Graham, S.J. et al., "Quantifying Tissue Damage Due to Focused Ultrasound Heating Observed by MRI" Magnetic Resonance in Medicine vol. 41, p. 321-328, 1999.
Goldberg, S. Nahum et al., "Radiofrequency Tissue Ablation: Increased Lesion Diameter with a Perfusion Electrode," Acad. Radiol. vol. 3, No. 8, p. 636-644, Aug. 1996.
Häcker, Axel et al., "Extracorporeal Organotripsy for Renal Tumours," Current Opinion in Urology, vol. 13, p. 221-225, 2003.
Hausberg, Martin et al., "Sympathetic Nerve Activity in End-Stage Renal Disease," Circulation, vol. 106, p. 1974-1979, 2002.
Ho, Siew Yen et al., "Anatomy of the Left Atrium: Implications for Radiofrequency Ablation of Atrial Fibrillation," J Cardiovasc Electrophysiol, vol. 10, p. 1525-1533, Nov. 1999.
Israel, Gary M. et al., "MRI of the Kidney and Urinary Tract," Journal of Magnetic Resonance Imaging, vol. 24, p. 725-734, 2006.
Jiang, S.C. et al., "Effects of Thermal Properties and Geometrical Dimensions on Skin Burn Injuries," Burns, vol. 28, p. 713-717, 2002.
Kaye, David M. et al., "Functional and Neurochemical Evidence for Partial Cardiac Sympathetic Reinnervation After Cardiac Transplantation in Humans," Circulation, vol. 88, No. 3, Sep. 1993.
Keane, David, "New Catheter Ablation Techniques for the Treatment of Cardiac Arrhythmias," Cardiac Electrophysiology Review vol. 6, No. 4, p. 341-348, 2002.
Kennedy, J.E. et al., "High Intensity Focused Ultrasound: Surgery of the Future?", The British Journal of Radiology, vol. 76, p. 590-599, Sep. 2003.
Lai, Yu-Chi et al., "Lesion Size Estimator of Cardiac Radiofrequency Ablation at Different Common Locations with Different Tip Temperatures," IEEE Transactions on Biomedical Engineering vol. 51, No. 10, p. 1859-1864, Oct. 2004.
Lauder, Lucas et al., "Renal Denervation in the Management of Hypertension," EuroIntervention, vol. 20, p. e467-e478, 2024.
Lele, P. P., "Effects of Focused Ultrasonic Radiation on Peripheral Nerve, with Observations on Local Heating," Experimental Neurology, vol. 8, p. 47-83, 1963.
Liao, Qingyao et al., "Optimal Strategy for HIFU-Based Renal Sympathetic Denervation in Canines," Frontiers in Cardiovascular Medicine vol. 8, p. 1-11, Oct. 2021.
Liem, L. Bing, "Progress in Cardiac Arrhythmia Ablation: Potential for Broader Application and Shorter Procedure Time," Journal of Cardiothoracic and Vascular Anesthesia, vol. 11, No. 7, p. 895-900, Dec. 1997.
Lin, James C., "Physical Aspects of Radiofrequency Ablation," Radiofrequency Catheter Ablation of Cardiac Arrhythmias, Basical Concepts and Clinical Applications, Second Edition, Edited by Shoei K. Stephen Huang & David K. Wilber, 2000.
Mahfoud, Felix et al., "Device Therapy of Hypertension," Circulation Research nol. 128, p. 1080-1099, Apr. 2021.
Makin, Inder Raj. S. et al., "Miniaturized Ultrasound Arrays for Interstitial Ablation and Imaging," Ultrasound in Med. & Biol. vol. 31, No. 11, p. 1539-1550, 2005.
Malcolm, A.L. et al., "Ablation of Tissue Volumes Using High Intensity Focused Ultrasound" Ultrasound in Med. & Biol. vol. 22 No. 5 p. 659-669, 1996.
Manolis, Antonis S. et al., "Radiofrequency Catheter Ablation for Cardiac Tachyarrhythmias," Annals of Internal Medicine, vol. 131, No. 6, p. 452-461, Sep. 1994.
Mompeo, Blanca et al., "The Gross Anatomy of the Renal Sympathetic Nerves Revisited," Clinical Anatomy vol. 29, p. 660-664, Apr. 2016.
Moore, J.H. et al., "The Biophysical Effects of Ultrasound on Median Nerve Distal Latencies," Electromyogr. Clin. Neurophysiol., vol. 40, p. 169-190, 2000.
Nath, Sunil et al., "Basic Aspects of Radiofrequency Catheter Ablation," Journal of Cardiovascular Electrophysiology vol. 5, No. 10, p. 863-876, Oct. 1994.
Nath, Sunil et al., "Biophysics and Pathology of Catheter Energy Delivery Systems," Progress in Cardiovascular Diseases, vol. XXXVII, No. 4, p. 185-204, Jan./Feb. 1995.
Nau, William H. et al., "MRI-Guided Interstitial Ultrasound Thermal Therapy of the Prostate: A Feasibility Study in the Canine Model," Medical Physics vol. 32, No. 3, p. 733-743, Mar. 2005.
Nikfarjam, Mehrdad et al., "Mechanisms of Focal Heat Destruction of Liver Tumors," Journal of Surgical Research, vol. 127, No. 2, p. 208-223, Aug. 2005.

(56) References Cited

OTHER PUBLICATIONS

Ninet, Jean et al., "Surgical Ablation of Atrial Fibrillation With Off-Pump, Epicardial, High-Intensity Focused Ultrasound: Results of A Multicenter Trial," The Journal of Thoracic and Cardiovascular Surgery, vol. 130, No. 3, p. 803.e1-803e.8, Sep. 2005.
Ohkubo, Toyoyuki et al., "Experimental Study of Catheter Ablation Using Ultrasound Energy in Canine and Porcine Hearts," Jpn. Heart J. vol. 39, No. 3, p. 399-409, May 1998.
Papademetriou, Vasilios et al., "Renal Nerve Ablation for Resistant Hypertension, How Did We Get Here, Present Status, and Future Directions," Circulation, No. 129, p. 1440-1451, 2014.
Pozzoli, Alberto et al., "Electrophysiological Efficacy of Epicor High-Intensity Focused Ultrasound," European Journal of Cardio-Thoracic surgery, vol. 42, p. 129-134, 2012.
Riis, Thomas et al., "Effective Ultrasonic Stimulation in Human Peripheral Nervous System," IEE Transactions on Biomedical Engineering, vol. XX, No. XX, p. 1-8, XXXX 2021.
Roux, N. et al., "The Myocardial Sleeves of the Pulmonary Veins: Potential Implications for Atrial Fibrillation," Surg. Radiol. Anat., vol. 26, p. 285-289, Feb. 2004.
Schuarte, Patrick et al., "Catheter Ablation of Cardiac Autonomic Nerves for Prevention of Vagal Atrial Fibrillation," Circulation vol. 102, p. 2774-2780, 2000.
Tellez, Armando et al., "Renal Artery Nerve Distribution and Density in the Porcine Model: Biologic Implications for the Development of Radiofrequency Ablation Therapies," Translational Research vol. 162 No. 6, p. 381-389, Dec. 2013.
Ter Haar, G., "Ultrasound Focal Beam Surgery," Ultrasound in Med. & Biol., vol. 21, No. 9, p. 1089-1100, 1995.
Ter Haar, G.R. et al., "Ultrasonic Heating of Mammalian Tissues In vivo," Br. J. Cancer vol. 45, Supp. V., p. 65-67, 1982.
Ter Haar, Gail R. "Therapeutic and Surgical Applications," Physical Principles of Medical Ultrasonics, Second Edition, Edited by C.R. Hill, J.C. Bamber, and G.R. Ter Haar, p. 407-456, 2004.
Trippodo, Nick C. et al., "Similarities of Genetic (Spontaneous) Hypertension," Circulation Research vol. 48, No. 3, p. 309-319, Mar. 1981.
Urban, Bruce A. et al., "Three-dimensional Volume-rendered CT Angiography of the Renal Arteries and Veins: Normal Anatomy, Variants, and Clinical Applications," RG vol. 21 No. 2, p. 373-386, Mar.-Apr. 2001.
Wang, Shyh-Hau et al., "Effects of Low Intensity Ultrasound on the Conduction Property of Neural Tissues," IEEE International Ultrasonics, Ferroelectrics, and Frequency Control Joint 50$^{th}$ Anniversary Conference, p. 1824-1827, 2004.
Weld, Kyle J. et al., "Comparison of Cryoablation, Radiofrequency Ablation and High-Intensity Focused Ultrasound for Treating Small Renal Tumours" BJU International vol. 96, p. 1224-1229, 2005.
Wells, P.N.T., "Functional Modification: Clinical Applications," Biomedical Ultrasonics, p. 470-504, 1977.
Winternitz, Sherry R. et al., "Importance of the Renal Nerves in the Pathogenesis of Experimental Hypertension," Hypertension (supp. III), vol. 4, No. 5, p. III-08-III-115, Sep.-Oct. 1982.
Wulff, V.J. et al., "Effects of Ultrasonic Vibrations on Nerve Tissues," P.S.E.B.M., vol. 76, p. 361-366, 1951.
Yarmolenko, Pavel S. et al., "Thresholds for thermal damage to normal tissues: An update," Int. J. Hyperthermia, vol. 27 No. 4, p. 320-343, Jun. 2011.
Young, Robert R. et al., "Functional Effects of Focused Ultrasound on Mammalian Nerves," Science, vol. 134, p. 1521-1522, Nov. 1961.
Zimmer, J.E. et al., "The Feasibility of Using Ultrasound for Cardiac Ablation," IEEE Transactions on Biomedical Engineering, vol. 42, No. 9, p. 891-897, Sep. 1995.

* cited by examiner

CATHETERS WITH BALLOONS ON WHICH ARE LOCATED ELECTRODES

PRIORITY CLAIM

This application claims priority to U.S. Provisional Application No. 63/480,208, filed Jan. 17, 2023, titled CATHETERS WITH BALLOONS ON WHICH ARE LOCATED ELECTRODES, which is incorporated herein by reference.

FIELD OF THE TECHNOLOGY

Certain embodiments of the present technology generally relate to catheters (also known as probes) configured to be inserted into a biological lumen (e.g., a renal artery) and used for obtaining neural measurements, and related apparatuses, systems and methods. Certain embodiments generally related to minimally invasive apparatuses, systems and methods that provide energy delivery to a targeted anatomical location of a subject, and more specifically, to catheter-based, intraluminal apparatuses, systems and methods including or utilizing an ultrasound transducer configured to emit ultrasonic energy for the treatment of tissue, such as nerve tissue.

BACKGROUND

Proper operation of the nervous system is an important part of proper organ function. It is desired to be able to monitor and change nervous system function in the human body to characterize and correct nervous system regulation of internal human organs. New medical therapies have been practiced whereby a probe such as a needle, catheter, wire, etc. is inserted into the body to a specified anatomical location and destructive means are conveyed to nerves by means of the probe to irreversibly damage tissue in the nearby regions. The objective is to modulate (e.g., abolish) nerve function in the specified anatomic location. The result is that abnormally functioning physiological processes can be terminated or modulated back into a normal range. An alternative objective can be to increase a physiologic process or modulate it to an abnormal range.

An example is renal nerve ablation to relieve hypertension. Various studies have confirmed the relationship of renal nerve activity with blood pressure regulation. In various renal ablation procedures, a catheter is introduced into a hypertensive patient's arterial vascular system and advanced into the renal artery. Destructive means are delivered proximate to the renal artery wall to an extent intended to cause destruction of nerve activity. Destructive means include energy such as radio frequency (RF), microwave, cryotherapy, ultrasound, laser or chemical agents. The objective is to abolish the renal nerve activity. Such nerve activity is an important factor in the creation and/or maintenance of hypertension and abolishment of the nerve activity reduces blood pressure and/or medication burden.

SUMMARY

The present technology is defined in the independent claims. Further embodiments of the technology are defined in the dependent claims.

A catheter for use in analyzing neural activity of nerves that surround a biological lumen includes a handle and a shaft extending from the handle. The shaft configured to be inserted into the biological lumen. The selectively inflatable balloon is located on the shaft. The distal electrode and the proximal electrode are longitudinally spaced apart from one another on the shaft. Each of the distal electrode and the proximal electrode is configured to be selectively transitioned between a non-intussuscepted position and an intussuscepted position.

A catheter for use in analyzing neural activity of nerves that surround a biological lumen includes a handle and a shaft extending from the handle. The shaft configured to be inserted into the biological lumen. The selectively inflatable balloon is located on the shaft. The distal spiral electrode is at least partially encircling a distal portion of the balloon. The proximal spiral electrode is at least partially encircling a proximal portion of the balloon. Each of the distal and proximal spiral electrodes is configured to be selectively transitioned between a non-deployed and a deployed position in response to the balloon being at least partially inflated.

A catheter for use in analyzing neural activity of nerves that surround a biological lumen includes a handle and a shaft extending from the handle. The shaft configured to be inserted into the biological lumen. The selectively inflatable balloon is located on the shaft and made for a non-electrically conductive material. The distal coated electrode is formed on and encircling the circumference of a distal portion of the balloon. The proximal coated electrode is formed on and encircling a circumference of a proximal portion of the balloon.

A method for use with a catheter including a handle, a shaft extending from the handle, a selectively inflatable balloon located on the shaft, and a distal electrode and a proximal electrode longitudinally spaced apart from one another. The method includes inserting at least a portion of the shaft into a biological lumen while the balloon is not inflated. At least partially inflating the balloon while the at least the portion of the shaft is inserted into the biological lumen. Causing the distal and proximal electrodes to come into contact respectively with first and second longitudinally spaced apart portions of the biological lumen while the distal and proximal electrodes respectively surround distal and proximal portions of the balloon. Sensing neural activity of nerves within the tissue surrounding the biological lumen using at least one of the distal and proximal electrodes that respectively surround the distal and proximal portions of the balloon and are in contact respectively with the first and second longitudinally spaced apart portions of the biological lumen.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

The various features of the present disclosure and the manner of attaining them will be described in greater detail with reference to the following description, claims, and drawings, wherein reference numerals are reused, where appropriate, to indicate a correspondence between the referenced items, and wherein:

FIG. 3A1 illustrates a cross-sectional view of a catheter shaft, along the line A-A in FIG. 2C, in accordance with an embodiment.

FIG. 3A2 illustrates a cross-sectional view of the catheter shaft, along the line A-A in FIG. 2C, in accordance with an alternative embodiment.

DETAILED DESCRIPTION

Figure 1:
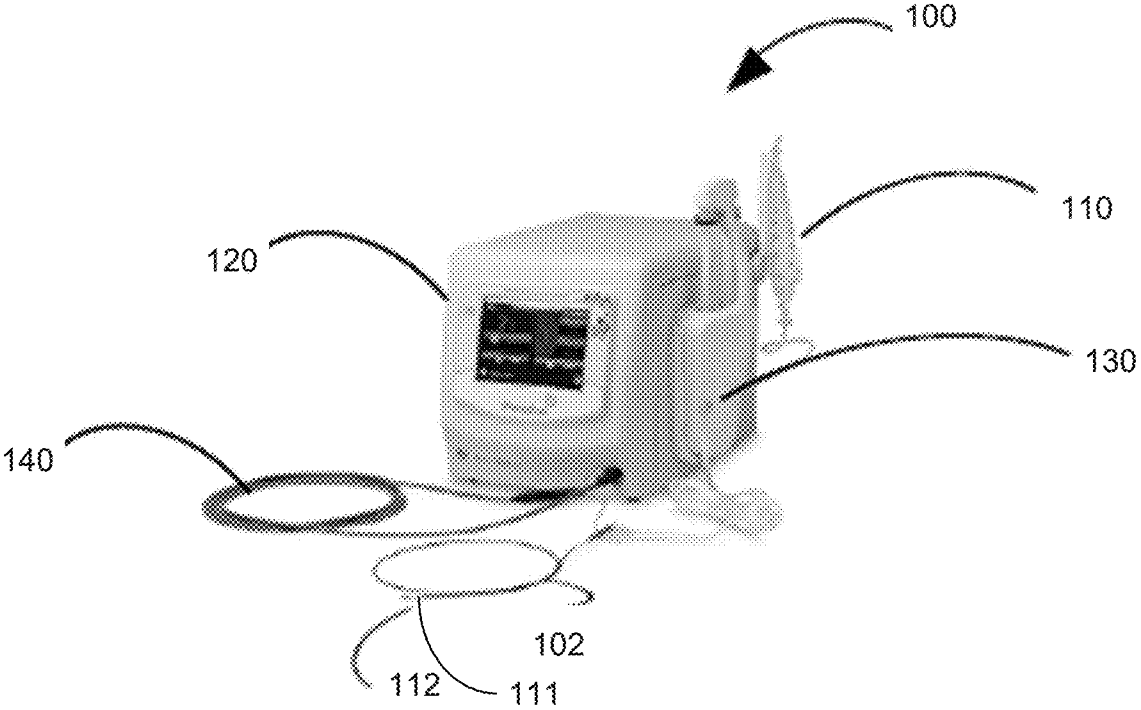
FIG. 1 illustrates selected components of an ultrasound-based tissue treatment system in accordance with certain embodiments of the present technology.

In the following detailed description of example embodiments, reference is made to specific example embodiments by way of drawings and illustrations. These examples are described in sufficient detail to enable those skilled in the art to practice what is described, and serve to illustrate how elements of these examples may be applied to various purposes or embodiments. Other embodiments exist, and logical, mechanical, electrical, and other changes may be made. Features or limitations of various embodiments described herein, however important to the example embodiments in which they are incorporated, do not limit other embodiments, and any reference to the elements, operation, and application of the examples serve only to define these example embodiments. Features or elements shown in various examples described herein can be combined in ways other than shown in the examples, and any such combination is explicitly contemplated to be within the scope of the examples presented here. The following detailed description does not, therefore, limit the scope of what is claimed.

Regulating operation of the nervous system to characterize nerve signaling and modulate organ function includes in some examples introduction of a probe such as a needle, catheter, wire, or the like into the body to a specified anatomical location, and partially destroying or ablating nerves using the probe to destroy nerve tissue in the region near the probe. By reducing nerve function in the selected location, an abnormally functioning physiological process can often be regulated back into a normal range. It would also be possible to modulate nerve function to purposely cause an abnormally functioning physiological process that is beneficial to the patient.

Unfortunately, not all patients respond to this therapy. One reason is that the delivery of destructive means towards the arterial wall does not have a feedback mechanism to assess the destruction of the nerve activity. As a consequence, an insufficient quantity of destructive means may be delivered, and nervous activity may not be abolished. Clinicians, therefore, require a means of improving the probe/tissue interface and better targeting of nerves, and an improved technology to monitor the integrity of the nerve fibers in order to confirm destruction of nerve activity prior to terminating therapy. Currently, nerve destructive means are applied empirically, without knowledge of whether the desired effect has been achieved.

Current autonomic nerve ablation procedures are performed in a ‘blind’ fashion; the clinician performing the procedure does not know where the nerves are located; and further, whether the nerves have truly been ablated. Instead, surrogates such as calf muscle sympathetic activity (MSNA) or catecholamine spillover into the circulating blood have been used to attempt to evaluate the reduction in organ specific autonomic activity such as renal nerve activity. It is entirely likely that this deficiency could at least partly be responsible for the current variability in clinical responses coming from clinical trials.

Unfortunately, it is typically very difficult to estimate the degree to which nerve activity has been reduced, which makes it difficult to perform a procedure where it is desired to ablate all nerves, or to ablate some, but not all, nerves to bring the nervous system response back into a desired range without destroying the nervous system response entirely.

One such example is renal nerve ablation to treat hypertension. Various studies have confirmed that renal nerve activity has been associated with hypertension, and that ablation of the nerve can improve renal function and reduce hypertension. In a typical procedure, a catheter is introduced into a hypertensive patient’s arterial vascular system and advanced into the renal artery. Renal nerves located in the arterial wall and in regions adjacent to the artery are ablated by destructive means such as radio frequency waves, microwave, cryotherapy, ultrasound, laser or chemical agents to limit the renal nerve activity, thereby reducing hypertension in the patient.

Unfortunately, renal nerve ablation procedures are sometimes ineffective, such as due to either insufficiently ablating the nerve or destroying more nerve tissue than is desired. Also, it may be desirable to avoid ablating other off-target tissues. Clinicians often estimate based on provided guideline estimates or past experience the degree to which application of a particular ablative method will reduce nerve activity, and it can take a significant period of time (e.g., 3-12 months) before the clinical effects of the ablation procedure are fully known.

Some attempt has been made to monitor nerve activity in such procedures by inserting very small electrodes into or adjacent to the nerve body, which are then used to electrically monitor the nerve activity. Such microneurography practices are not practical in the case of renal ablation because the renal arteries and nerves are located within the abdomen and cannot be readily accessed, making monitoring and characterization of nerve activity in a renal nerve ablation procedure a challenge.

Prior methods such as inserting electrodes into the arteries of a patient’s heart and analyzing received electrical signals are not readily adaptable to renal procedures. In the heart, the ablated tissue is heart muscle which itself is electrically conductive. Further, the cardiac electrical signals emitted from the heart are generally large and slow-moving relative to electrical signals near the renal arteries, which tend to be smaller in size and produce smaller signals that propagate more quickly through the nerves. In the case of renal denervation, the target of the ablation is renal nerves which lie outside the lumen of the blood vessel, and the blood vessel tissue is different from myocardium and acts as a barrier to adequately sense nerve firing. As such, intracardiac techniques used in heart measurements are not readily adaptable to similar renal procedures.

Because nerve activity during procedures to ablate or neuromodulate enervation of organs such as renal nerve ablation cannot be readily measured, it is also difficult to ensure that an ablation probe is located at the most appropriate sites along the renal artery, or to measure the efficiency of the nerve ablation process in a particular patient.

Acoustic-based tissue treatment transducers, apparatuses, systems, and portions thereof, are provided herein. Preferably, the systems are catheter-based and may be delivered intraluminally (e.g., intravascularly) so as to place a transducer within a target anatomical region of the subject, for example, within a suitable body lumen such as a blood vessel. Once properly positioned within the target anatomical region, the transducer can be activated to deliver unfocused ultrasonic energy radially outwardly so as to suitably heat, and thus treat, tissue within the target anatomical region. The transducer can be activated at a frequency, duration, and energy level suitable for treating the targeted tissue. In one nonlimiting example, the unfocused ultrasonic energy generated by the transducer may target select nerve tissue of the subject, and may heat such tissue in such a manner as to neuromodulate (e.g., fully or partially ablate, necrose, or stimulate) the nerve tissue. Neuromodulating renal nerves may be used to treat various conditions, e.g., hypertension, chronic kidney disease, atrial fibrillation, etc. However, it should be appreciated that the transducers suitably may be used to treat other nerves and conditions, e.g., sympathetic nerves of the hepatic plexus within a hepatic artery responsible for blood glucose levels important to treating diabetes, or any suitable tissue, e.g., heart tissue triggering an abnormal heart rhythm, and is not limited to use in treating (e.g., neuromodulating) renal nerve tissue.

In an intraluminal system, an ultrasound transducer may be disposed within a balloon that is filled with a cooling fluid before and during treatment. In certain embodiments, a balloon may surround the transducer, and the balloon may contact the interior surface (e.g., intima) of the body lumen BL. In certain embodiments, the transducer may be used to output an acoustic signal when the balloon fully occludes a body lumen BL, and the cooling fluid within the balloon may be used to cool both the body lumen and the transducer. In certain embodiments, the balloon may surround the transducer in order to cool the transducer during sonications, but the balloon may not contact or occlude the body lumen, and the blood within the body lumen may be relied upon to cool the body lumen instead of the cooling fluid. The term body lumen is also referred to herein interchangeably as the term biological lumen.

Overview of System Components and Features

Figure 2A:
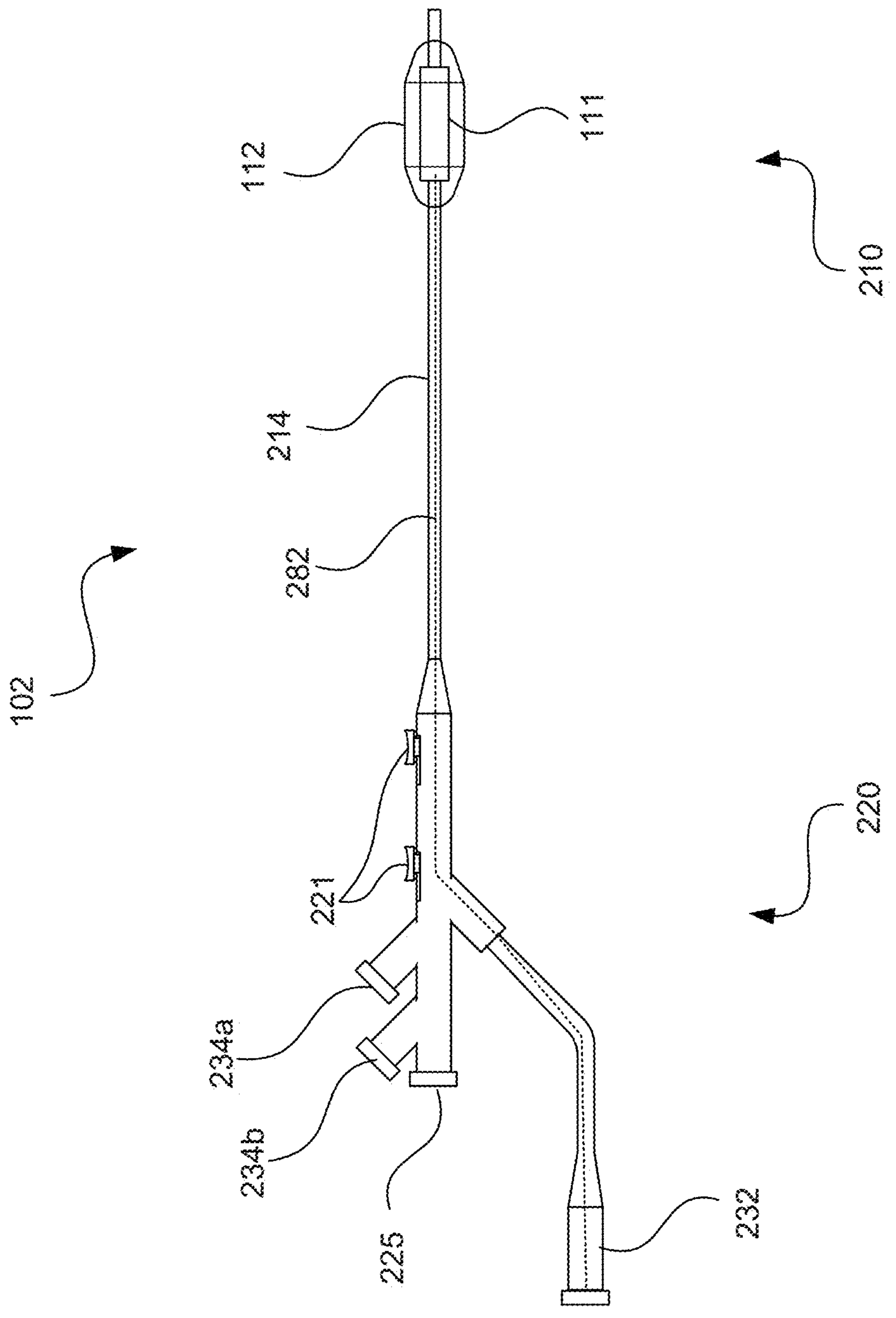
FIG. 2A illustrates a side view of selected components of the ultrasound-based tissue treatment system introduced in FIG. 1, in accordance with certain embodiments.
Figure 2B:
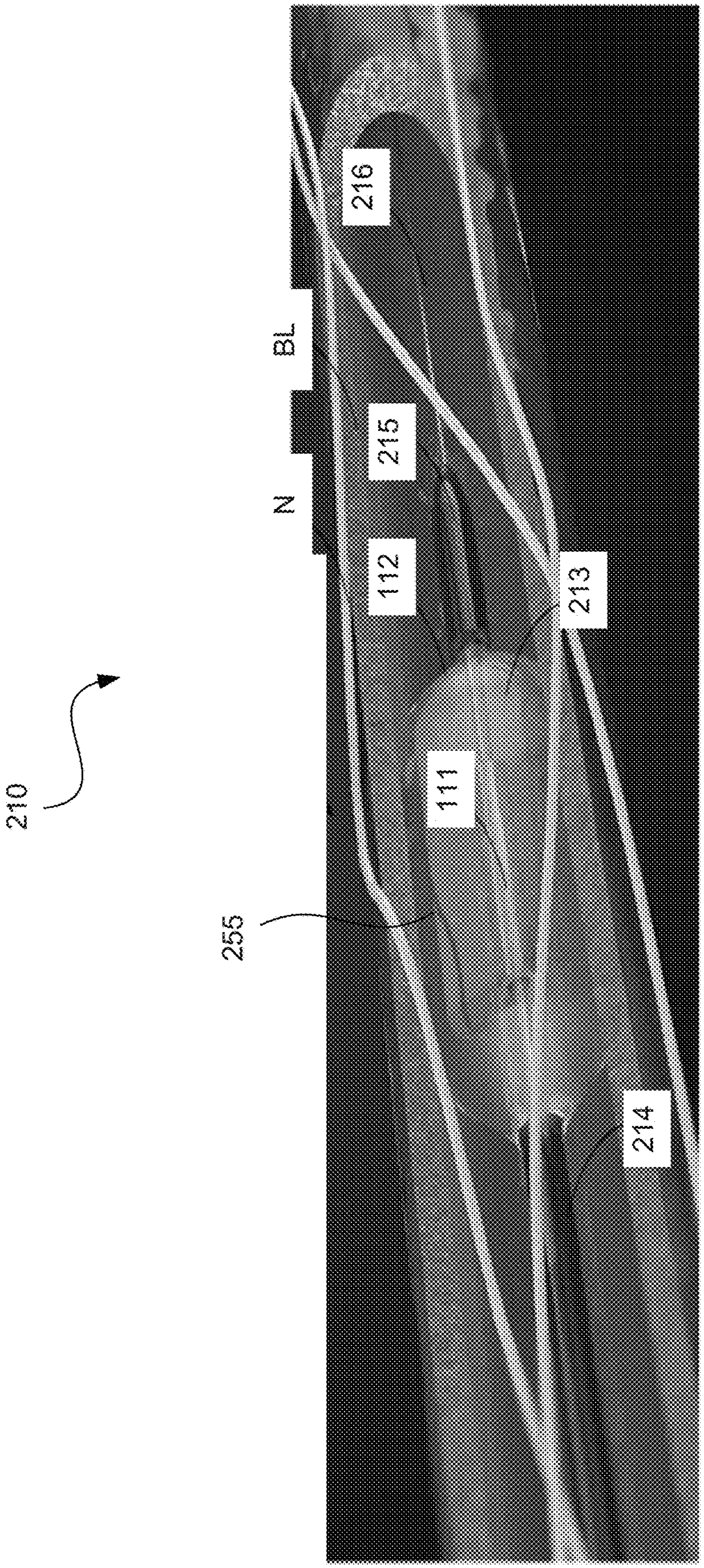
FIG. 2B illustrates a perspective view of additional selected components of the ultrasound-based tissue treatment system inserted into a body lumen (aka biological lumen) in accordance to various configurations provided herein.

FIGS. 1, 2A, and 2B illustrate features of an ultrasound-based tissue treatment system 100, according to various configurations provided herein. Referring initially to FIG. 1, the system 100 is shown as including a catheter 102, a controller 120, and a connection cable 140. In certain embodiments, the system 100 further includes an ultrasound transducer 111 within a balloon 112, a reservoir 110, a cartridge 130, and a control mechanism, such as a handheld remote control.

In the embodiment shown in FIG. 1, the controller 120 is shown as being connected to the catheter 102 through the cartridge 130 and the connection cable 140. In certain embodiments, the controller 120 interfaces with the cartridge 130 to provide a cooling fluid to the catheter 102 for selectively inflating and deflating the balloon 112. The balloon 112 can be made, e.g., from nylon, a polyimide film, a thermoplastic elastomer (such as those marked under the trademark PEBAX™), a medical-grade thermoplastic polyurethane elastomers (such as those marketed under the trademark PELLETHANE™), pellethane, isothane, or other suitable polymers or any combination thereof, but is not limited thereto.

Referring now to FIG. 2A, the catheter 102 includes a distal portion 210 and a proximal portion 220. The catheter 102 includes a catheter shaft 214, which can include one or more lumens extending therethrough. For an example, the catheter shaft 214 includes a guidewire lumen 225 that is shaped, sized and otherwise configured to receive a guidewire. In certain embodiments suitable, e.g., for renal denervation, the catheter 102 may be about 6 French or 5 French in diameter and about 85 cm to about 155 cm in length, but is not limited thereto. In certain embodiments, e.g., the catheter 102 can be about 4 French in diameter. The proximal portion 220 of the catheter 102 may include one or more connectors or couplings. For example, the proximal portion 220 may include one or more electrical coupling(s) 232. Since the proximal portion 220 of the catheter 102 is configured to be held by a person, the proximal portion may also be referred to as the handle 220. As shown in FIG. 2A, the handle 220 can include one or more actuators 221 (e.g., slidable actuators) that can be used to selectively deploy one or more electrodes (discussed below) positioned on the catheter shaft 214.

The catheter 102 may be coupled to the controller 120 by connecting the electrical coupling(s) 232 to the connection cable 140. The connection cable 140 may be removably connected to the controller 120 and/or the catheter 102 via a port on the controller 120 and/or the catheter 102, in order to permit use of multiple catheters during a procedure. In certain embodiments, e.g., where only one catheter 102 needs to be used during a procedure, the connection cable 140 may be permanently connected to the controller 120. As will be described in additional detail below, electrical cabling (represented by the dashed line 282 in FIG. 2A) that extends through at least one lumen of the catheter 102 electrically couples the transducer 111 to the electrical coupling(s) 232.

In certain embodiments, the proximal portion 220 of the catheter 102 may further include one or more fluidic ports, e.g., a fluidic inlet port 234*a* and a fluidic outlet port 234*b*, via which the balloon 112 may be fluidly coupled to the cartridge 130 (shown in FIG. 1), which supplies cooling fluid. The cartridge 130 optionally may be included within controller 120, attached to the outer housing of controller 120 as shown in FIG. 1, or may be provided separately. Example details of the cartridge 130 and the reservoir 110 are described below with reference to FIG. 5.

FIG. 2B illustrates a perspective view of selected components of the catheter 102, e.g., components of the distal portion 210 as may be inserted into a body lumen BL of a subject. In FIG. 2B, the body lumen BL is a blood vessel (e.g., a renal artery) that has a plurality of nerves N in an outer layer (e.g., adventitia layer) of the blood vessel. As illustrated in FIG. 2B, the distal portion 210 may include the ultrasound transducer 111, the balloon 112 filled with a cooling fluid 213, the catheter shaft 214, and/or a guidewire support tip 215 configured to receive a guidewire 216.

The transducer 111 may be disposed partially or completely within the balloon 112, which may be inflated with a cooling fluid 213 so as to contact the interior surface (e.g., intima) of the body lumen BL. In certain embodiments, the transducer 111 may be used to output an acoustic signal when the balloon 112 fully occludes a body lumen BL. The balloon 112 may center the transducer 111 within the body lumen BL. In certain embodiments, e.g., suitable for renal denervation, the balloon 112 is inflated while inserted in the body lumen BL of the patient during a procedure at a working pressure of about 1.4 to 2 atm using the cooling fluid 213. The balloon 112 may be or include a compliant, semi-compliant or non-compliant medical balloon. The balloon 112 is sized for insertion in the body lumen BL and, in the case of insertion into the renal artery, for example, the balloon 112 may be selected from available sizes including outer diameters of 3.5, 4.2, 5, 6, 7, or 8 mm, but not limited thereto. In some embodiments, as shown in FIG. 2B, when inflated by being filled with the cooling fluid 213 under the control of the controller 120, the outer wall of the balloon 112 may be generally parallel with the outer surface of the transducer 111. Optionally, the balloon 112 may be inflated sufficiently as to be in apposition with the body lumen BL. For example, when inflated, the balloon 112 may at least partially contact, and thus be in apposition with, the inner wall of the body lumen BL.

Figure 2C:
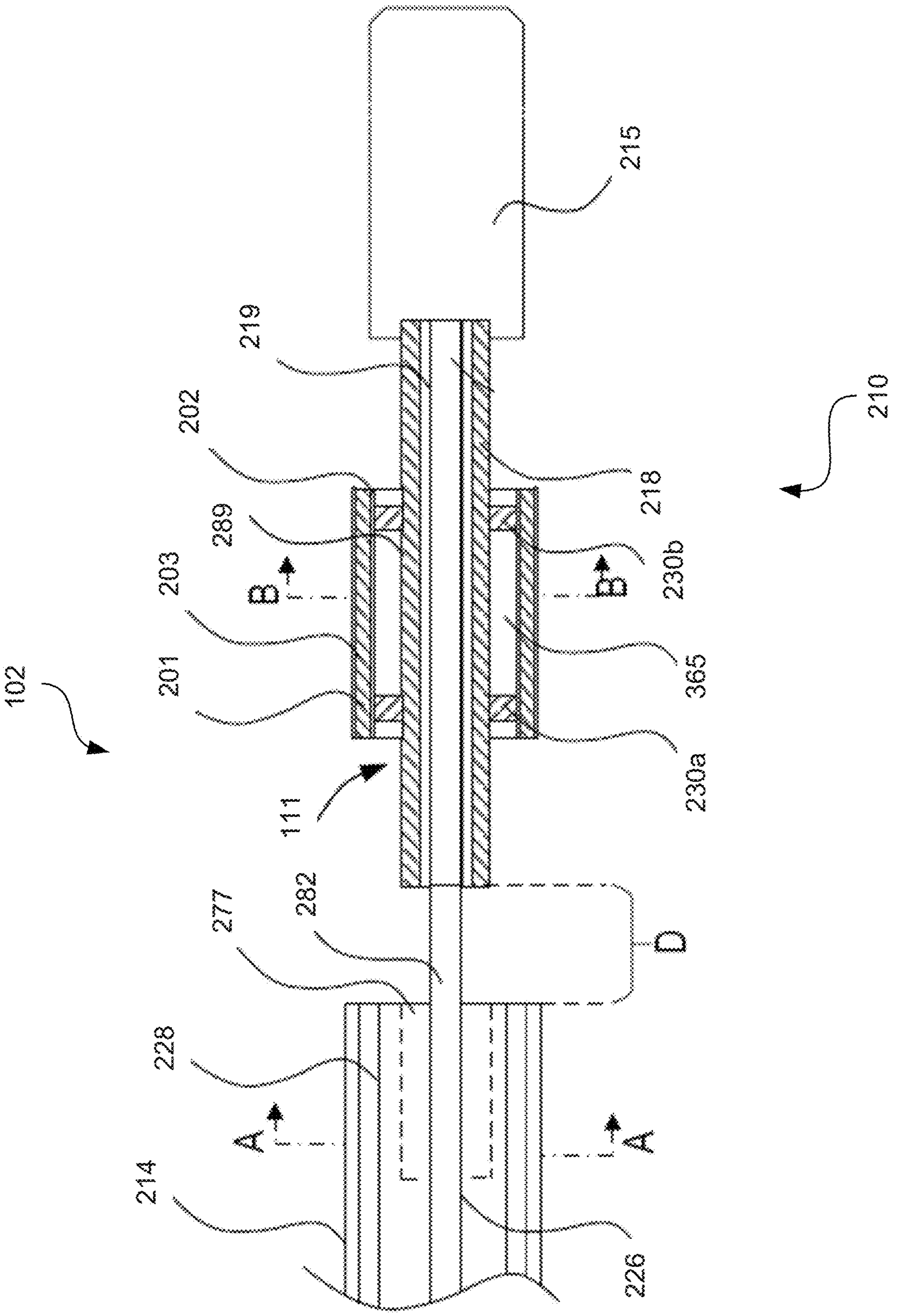
FIG. 2C illustrates a longitudinal cross-sectional view of a distal portion of a catheter of the ultrasound-based tissue treatment system in accordance with an embodiment of the present technology.

FIG. 2C illustrates a longitudinal cross-sectional view of the distal portion 210 of the catheter 102. FIG. 3A1 illustrates a cross-sectional view of the catheter shaft 214 along the line A-A shown in FIG. 2C, according to an embodiment. FIG. 3A2 illustrates a cross-sectional view of the catheter shaft 214 along the line A-A shown in FIG. 2C, according to an alternative embodiment. FIG. 3B illustrates a cross-sectional view of the ultrasound transducer 111 along the line B-B shown in FIG. 2C, according to an embodiment. In certain embodiments, the catheter shaft 214 may be about 1.8 mm in diameter. The catheter shaft 214 can be made, e.g., from a thermoplastic elastomer (such as those marked under the trademark PEBAX™), a medical-grade thermoplastic polyurethane elastomers (such as those marketed under the trademark PELLETHANE™), pellethane, isothane, or other suitable polymers or any combination thereof, but is not limited thereto. The catheter shaft 214 includes one or more lumens that may be used as fluid conduits, an electrical cabling passageway, a guidewire lumen and/or the like, as described in further detail below with reference to FIGS. 3A1 and 3A2. In certain embodiments suitable, e.g., for renal denervation, the guidewire 216 has a diameter of about 0.36 mm and a length of from about 180 cm to about 300 cm, and is delivered using a 7 French guide catheter, having a minimum inner diameter of 2.06 mm and a length less than about 80 cm. In certain embodiments, a 6 French guide catheter is used to deliver the guidewire 216. In certain embodiments, the guide catheter has a length of about 55 cm. In certain embodiments, the guide catheter has a length of about 85 cm and a hemostatic valve is attached to the hub of the guide catheter to allow for continuous irrigation of the guide catheter to decrease the risk of thromboembolism.

Referring again to FIG. 2C, the ultrasound transducer 111 may include a cylindrical hollow tube 201 made of a piezoelectric material (e.g., lead zirconate titanate (PZT), etc.), with inner and outer electrodes 202, 203 disposed on the inner and outer surfaces of the cylindrical tube 201, respectively. Such a cylindrical hollow tube of piezoelectric material is an example of, and thus can be referred to as, a piezoelectric transducer body 201. The piezoelectric transducer body 201 can have various other shapes and need not be hollow. In certain embodiments suitable, e.g., for renal denervation, the piezoelectric material, of which the piezoelectric transducer body 201 is made, is lead zirconate titanate 8 (PZT8), which is also known as Navy III Piezo Material. Raw PZT transducers may be plated with layers of copper, nickel and/or gold to create electrodes on surfaces (e.g., the inner and outer surfaces) of the piezoelectric transducer body (e.g., 201). Application of a voltage and alternating current across inner and outer electrodes 202, 203 causes the piezoelectric material to vibrate transverse to the longitudinal direction of the cylindrical tube 201 and radially emit ultrasonic waves. While the ultrasound transducer 111 in FIG. 2C is not shown as being surrounded by a balloon, it is noted that the ultrasound transducer 111 can be positioned within a balloon (e.g., 112), e.g., as shown in FIGS. 2A and 2B.

As shown in FIG. 2C, the ultrasound transducer 111 is generally supported via a backing member or post 218. In certain embodiments, the backing member 218 (which can also be referred to as the post 218) comprises stainless steel coated with nickel and gold, wherein nickel is used as a bonding material between the stainless steel and gold plating. In certain embodiments suitable, e.g., for renal denervation, an outer diameter of the transducer 111 is about 1.5 mm, an inner diameter of the transducer 111 is about 1 mm, and the transducer 111 has a length of about 6 mm. Transducers having other inner diameters, outer diameters, and lengths, and more generally dimensions and shapes, are also within the scope of the embodiments described herein. Further, it is noted that the drawings in the FIGS. are not necessarily drawn to scale, and often are not drawn to scale.

As illustrated in FIG. 2C, the backing member 218 may extend from the distal portion 210 of the catheter shaft 214 to a distal tip 215. For example, the distal end of the backing member 218 may be positioned within an adjacent opening in the tip 215, and the proximal end of the backing member 218 may be moveably coupled to the distal portion 210 of the catheter shaft 214 via the electrical cabling 282. In other embodiments, there is a gap (e.g., labeled D in FIG. 2C) between the distal end of the catheter shaft 214 and the proximal end of the ultrasound transducer 111. Additional details of the electrical cabling 282, and how the electrical cabling may be electrically coupled to the transducer 111, are described below.

In order to permit liquid cooling along both the inner and outer electrodes 202, 203, the backing member 218 may include one or more stand-off assemblies **230*a* and 230*b*. The stand-off assemblies 230*a*, 230*b* may define one or more annular openings through which cooling fluid 213 may enter the space of the transducer 111 (which may be selectively insulated) between the backing member 218 and the inner electrode 202. Accordingly, the backing member 218 may serve as a fluid barrier between the cooling fluid 213 circulated within the balloon 112 and the lumen of the backing member 218 that receives the guidewire 216. As shown schematically in FIG. 2C, for example, the stand-off assemblies 230*a*, 230*b* of the backing member 218 may be positioned along or adjacent to each longitudinal end of the ultrasound transducer 111 (separated by a main post body 289) and couple the cylindrical tube 201 of the ultrasound transducer 111 to the backing member 218. With reference to FIG. 3B, a stand-off assembly 230 (230*a* or 230*b*) may have a plurality of lugs, ribs, or attachment points 334 that engage the inner electrode 202 of the transducer 111. In certain embodiments, the attachment points 334 are soldered to the inner electrode 202 of the transducer 111. The number, dimensions, and placement of the ribs 334 may vary, as desired or required. For example, as illustrated in FIG. 3B, a total of three ribs 334 can be generally equally spaced apart from one another at an angle of 120 degrees apart from one another, defining openings 336 through which a cooling fluid or blood may enter an interior space of the cylindrical tube 201 between the inner electrode 202 disposed along the inner surface of the cylindrical tube 201 and the backing member 218. In certain embodiments, the maximum outer diameter of stand-off assemblies 230*a* and 230*b* is about 1 mm, the outer diameter of the main post body 289 is about 0.76 mm, and the inner diameter of backing member 218** is about 0.56 mm.

In accordance with certain embodiments, the stand-off assemblies **230*a*, 230*b* are electrically conductive, so as to electrically couple the inner electrode 202 of the ultrasound transducer 111 to the backing member 218. One or more conductors of the electrical cabling 282 may be electrically coupled to the backing member 218. Thus, as the controller 120 is activated, current may be delivered from the electrical cabling 282 to the inner electrode 202 of the ultrasound transducer 111 via the backing member 218 and the stand-off assemblies 230*a*, 230*b*, which advantageously eliminates the need to couple the cabling 282 directly to the inner electrode 202 of the transducer 111. In other embodiments, the backing member 218 and the stand-off assemblies 230*a*, 230*b* are made of one or more electrical insulator material(s), or if made of an electrically conductive material(s) are coated with one or more electrical insulator material(s). In certain embodiments, one or more electrical conductors of the cabling 282 are directly coupled (e.g., soldered) to the inner electrode 202 of the transducer 111**.

Moreover, as illustrated in FIG. 2C, the backing member 218 may have an isolation tube 219 disposed along its interior surface so as to prevent or reduce the likelihood of electrical conduction between the guidewire 216 (shown in FIG. 2B) and the backing member 218, for use in embodiments where such an electrical conduction is not desired. The isolation tube 219 can be formed of a non-electrically conductive material (e.g., a polymer, such as polyimide), which can also be referred to as an electrical insulator. As illustrated in FIG. 2C, the isolation tube 219 may extend from the catheter shaft 214 through the lumen of the backing member 218 within the transducer 111 to the tip 215. In this manner, the transducer 111 is distally offset from the distal end of the catheter shaft 214.

As illustrated in FIGS. 2C, the catheter 102 may also include a bore 277 extending from the distal end of the catheter 102 proximally within the catheter 102, and sized and shaped to receive at least a portion of the backing member 218, thereby electrically insulating the isolation tube 219 and/or the ultrasound transducer 111. Accordingly, during delivery of the catheter 102 to the anatomical region being treated, the backing member 218, the isolation tube 219, and/or the ultrasound transducer 111 may be at least partially retracted within the bore 277 of the catheter 102, e.g., by retracting the electrical cabling 282, thereby providing sufficient stiffness to the catheter 102 such that the catheter 102 may be delivered in a safe manner.

Figure 2D:
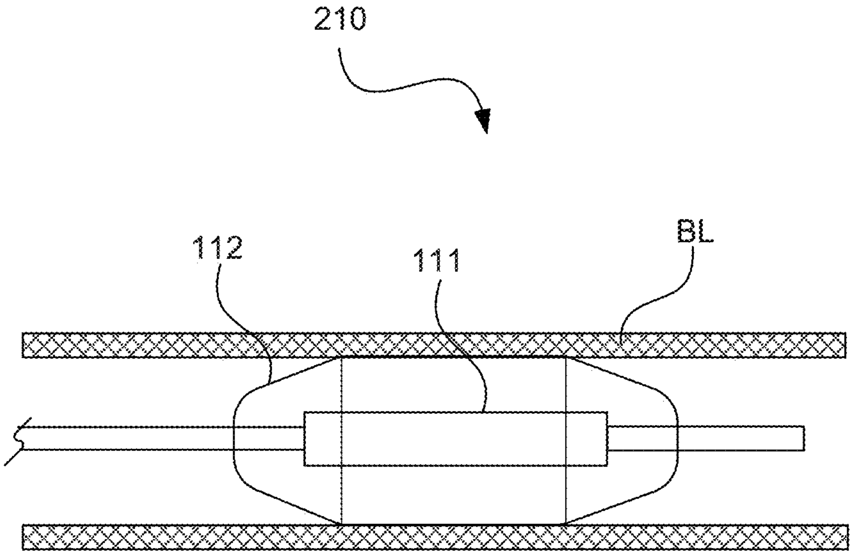
FIG. 2D illustrates how a balloon that surrounds an ultrasound transducer and is in apposition with a body lumen can be used to center the transducer within the body lumen, in accordance with certain embodiments.
Figure 3B:
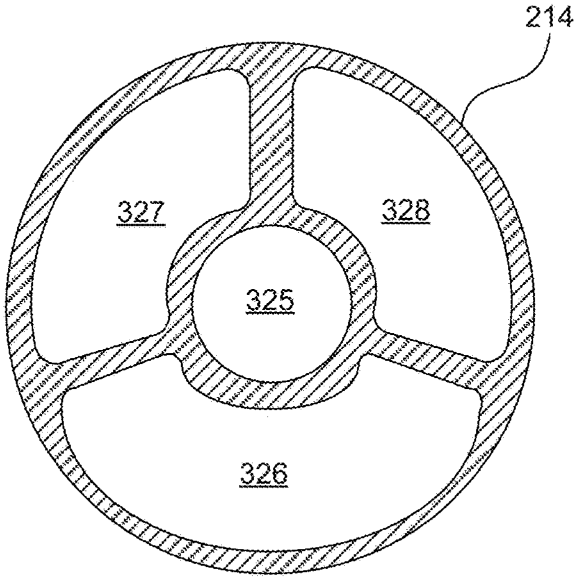
FIG. 3B illustrates a cross-sectional view across a portion of the ultrasound transducer of the catheter, along the line B-B in FIG. 2C, in accordance with certain embodiments.
Figure 3B:
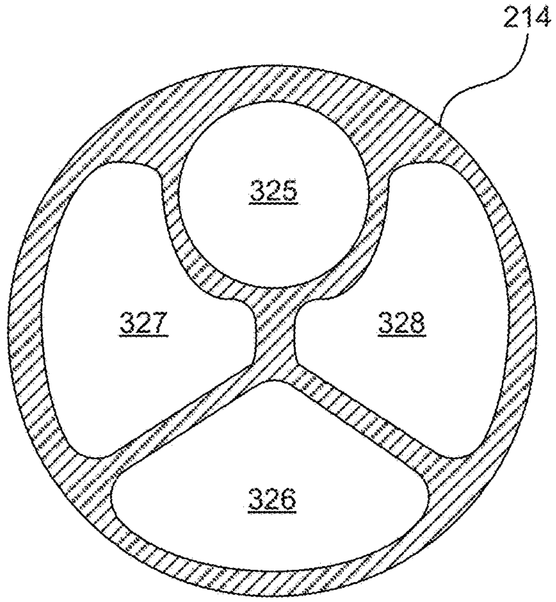
Figure 3B:
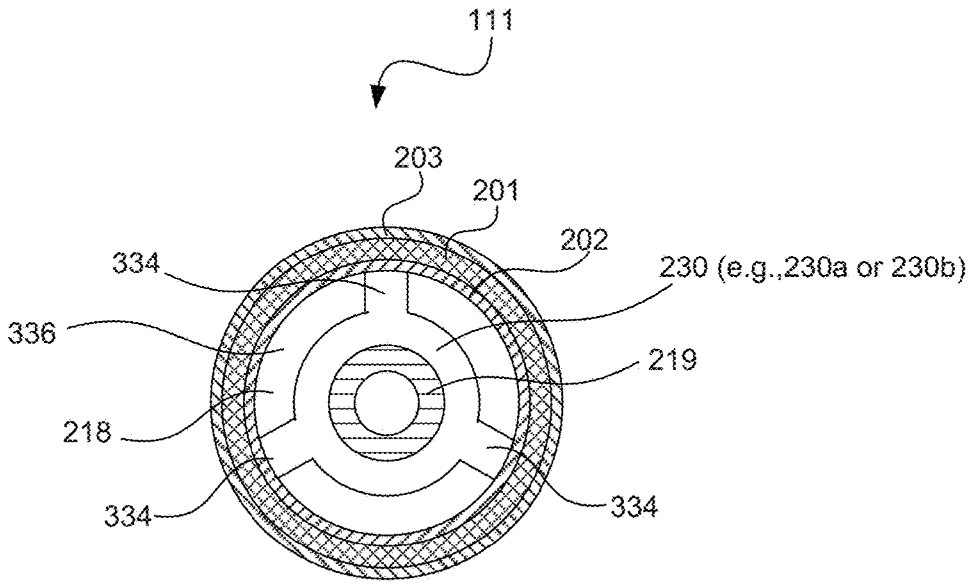

FIG. 2D shows a distal portion 210 of the catheter 102 inserted into a body lumen (BL), such as a renal artery, such that the balloon 112 when sufficiently inflated with cooling fluid is in apposition with the body lumen BL. More specifically, the balloon 112 is shown as being inflated such that an outer circumference of the balloon 112 contacts an inner circumference of the biological lumen BL and thereby restricts blood from flowing past the balloon. As will be described in additional detail below, where the balloon 112 includes a distal electrode and a proximal electrode (e.g., on an outer surface of the balloon 112), as is the case in certain embodiments, the balloon 112 prevents blood from flowing a first location adjacent the distal electrode to a second location adjacent the proximal electrode, and/or vice versa, which provides for certain benefits described below.

As illustrated in FIGS. 3A1 and 3A2, the catheter shaft 214 includes one or more lumens that can be used as fluid conduits, electrical cabling passageways, guidewire lumen, and/or the like. For example, as illustrated in FIGS. 3A1 and 3A2, the catheter shaft 214 may comprise a guidewire lumen 325 that is shaped, sized and otherwise configured to receive the guidewire 216. In certain embodiments, as illustrated in FIG. 3A1, the guidewire lumen 325 is located in the center of the catheter shaft 214 in order to center the transducer 111 within the catheter shaft 214. Alternatively, the guidewire lumen 325 can be offset from the center of the catheter shaft 214, e.g., as shown in FIG. 3A2. The catheter shaft 214 may also include a cable lumen 326 for receiving electrical cabling 282. Further, the catheter shaft 214 can include one or more fluid lumens 327, 328 for transferring the cooling fluid 213 (e.g., water, sterile water, saline, 5% dextrose (D5 W)), other liquids or gases, etc., from and to a fluid source, e.g., the reservoir 110 and cartridge 130, at the proximal portion 220 of the catheter 102 (external to the patient) to the balloon 112 under control of the controller 120. Active cooling of about the first millimeter of tissue is designed to preserve the integrity of the blood vessel wall, e.g., the renal arterial wall. The guidewire lumen 325 can extend longitudinally through the entire catheter shaft 214, parallel to the fluid lumens 327, 328. Alternatively, the guidewire lumen 325 may extend longitudinally through only a portion of the catheter shaft 214, e.g., where the catheter 102 is a rapid exchange (Rx) type of catheter.

The catheter 102 may include only a single fluid lumen or two or more fluid lumens (e.g., 3, 4, more than 4, etc.), as desired or required. As illustrated in FIG. 3A1, in an embodiment, the fluid lumens 327 and 328 and the cable lumen 326 all have a kidney-shaped or D-shaped cross-sections configured to maximize efficiency of fluid flow delivery and distribute fluid uniformly across the ultrasound transducer 111 by maximizing area, while minimizing the perimeter of the fluid lumens 327 and 328. In certain embodiments, each of the fluid lumens 327 and 328 and the cable lumen 326 are substantially symmetrical, the same size, the same geometry, and/or are interchangeable, e.g., as shown in FIG. 3A1. Changes in fluid flow rate within the catheter can lead to delayed, incomplete, or over treatment. In certain embodiments, the catheter shaft 214 is configured to enable a fluid flow rate of about 40 mL/min. In certain embodiments, the catheter shaft 214 is configured to enable a fluid flow rate of about 35 to 45 mL/min. In certain embodiments, the catheter shaft 214 is configured to enable a fluid flow rate of about 20 to 45 mL/min. In certain embodiments, e.g., suitable for radial delivery during a renal denervation procedure, the catheter shaft 214 is configured to enable a fluid flow rate of about 10 to 20 mL/min. Each of one or more lumens (e.g., 328) may be in fluid communication with the same or separate, individual fluid sources external to the patient at the proximal portion 220 of the catheter 102.

In certain embodiments, as illustrated in FIG. 3A2, the guidewire lumen 325 is located proximal to and/or shares a wall with the catheter shaft 214 so as to enable expedited exchange of catheters during a procedure. In such embodiments, the cable lumen 326 may be located opposite the guidewire lumen 225 and also share a wall with the catheter shaft 214. The cable lumen 326 may be, e.g., triangular or rectangular in shape, and may be configured to maximize the area available for and minimize the perimeter of the fluid lumens 327 and 328, thereby enabling a higher flow rate for the same pressure. The fluid lumens 327 and 328 may be shaped so as to optimize flow rate and reduce, and preferably minimize, fluidic friction. In such embodiments, the area of fluid lumens 327 and 328 may not be maximized, but instead the walls of the fluid lumens 327 and 328 may be rounded to avoid pockets that may otherwise cause fluidic friction, thereby optimizing flow rate of the cooling fluid 213 within the fluid lumens 327 and 328.

The catheter shaft 214 may include within at least the cable lumen 326, the electrical cabling 282 (e.g., a coaxial cable, parallel coaxial cables, a shielded parallel pair cable, one or more wires, or one or more other electrical conductors) coupling the inner and outer electrodes 202, 203 of the ultrasound transducer 111 to the controller 120, such that the controller 120 may apply a suitable voltage across such electrodes so as to cause the piezoelectric material of the transducer 111 to emit ultrasonic energy to a subject. In certain embodiments, the cable lumen 326 is shaped, sized and otherwise configured to receive the electrical cabling 282 (e.g., coaxial cable(s), wire(s), other electrical conductor(s), etc.). The electrical cabling 282 permits the electrodes 202, 203 of the ultrasound transducer 111 to be selectively activated in order to emit acoustic energy to a subject. More specifically, the electrical cabling 282 can allow for the communication of transducer information, such as operating frequency and power, from the catheter 102 to the controller 120 and/or vice versa, as well as the transfer of electrical energy to the ultrasound transducer 111 during a procedure.

The distal portion 210 of the catheter 102 may be percutaneously delivered to the target anatomical location (e.g., at a specified location within the body lumen BL) via any suitable intraluminal access route, e.g., via a gastrointestinal route or via an intravascular route such as the femoral or radial route. In certain embodiments, the controller 120 is configured so as to fill the balloon 112 with the cooling fluid 213 only after the distal portion 210 of the catheter 102 is suitably positioned at the target anatomical location. The catheter 102 may be delivered through the body lumen BL with or without the assistance of a commercially available guidewire. For example, the catheter 102 and the balloon 112 may be delivered over the guidewire 216 (shown in FIG. 2B) and through a renal guide catheter. For further examples of guidewire-based delivery of ultrasound transducers, see U.S. Pat. No. 10,456,605, which was incorporated herein by reference above. However, it should be appreciated that any suitable steerable catheter or sheath, or any other suitable guiding device or method, may be used to deliver the distal portion 210 of the catheter 102 to a target anatomical location of the subject. Once delivered to a suitable location within the body lumen BL, the balloon 112 may be inflated with the cooling fluid 213 (e.g., under control of controller 120), and the transducer 111 may be actuated (e.g., by applying a voltage across the inner and outer electrodes 202, 203 under control of the controller 120) so as to deliver unfocused ultrasonic energy to the target anatomical location. The transducer 111 is sized for insertion in the body lumen BL and, in the case of insertion of the renal artery, for example, the transducer 111 may have an outer diameter of less than 2 mm, for example, about 1.5 mm and an inner diameter of less than 1.8 mm, for example, about 1 mm. As described in greater detail below, the length L of the transducer 111 optionally may be selected such that the ultrasonic waves that it generates has a near field depth suitable for generating a lesion only within a desired region relative to the wall of a target body lumen BL.

It will be appreciated that the frequency, power, and amount of time for which the transducer 111 is actuated suitably may be selected based on the treatment to be performed. For example, the frequency optionally is in a range of from 1 to 20 MHz, e.g., 1-5 MHz, 5-10 MHz, 8.5-9.5 MHz, 10-15 MHz, 15-20 MHz, or 8-10 MHz, for example, about 9 MHz. Or, for example, the frequency optionally is in a range of below 1 MHz, e.g., 0.1-0.2 MHz, 0.2-0.3 MHz, 0.3-0.4 MHz, 0.4-0.5 MHz, 0.5-0.6 MHz, 0.6-0.7 MHz, 0.7-0.8 MHz, 0.8-0.9 MHz, or 0.9-1.0 MHz. Or, for example, the frequency optionally is in a range of above 20 MHz, e.g., 20-25 MHz, 25-30 MHz, or above 30 MHz. Optionally, the power may be in a range of 5 to 80 W (e.g., 5 to 50 W, 5 to 10 W, 12.1-16.6 W, 10 to 20 W, 20 to 30 W, 30 to 40 W, 40 to 50 W, 50 to 60 W, 60 to 70 W, or 70 to 80 W, or may be more than 80 W). For example, the power may be 20 to 40 W with 20 to 30 W for balloons with smaller diameters (e.g., 3.5 to 5 mm) and 30 to 40 W for balloons with larger diameters (e.g., 5 to 8 mm). The period of time during which the transducer 111 is actuated may be sufficient to complete the particular treatment being performed, and may depend on factors such as the power at the transducer, the frequency of ultrasonic energy emitted, the size of the tissue region being treated, the age, weight and gender of the patient being treated, and/or the like. Illustratively, in some configurations the time period for which the transducer 111 may be actuated may be in a range of about 3 seconds to 5 minutes, e.g., 3-10 seconds, 3-30 seconds, 30 seconds to 1 minute, 30 seconds to 5 minutes, 1 to 3 minutes, about 2 minutes, 10 seconds to 1 minute, 1 to 2 minutes, 2 to 3 minutes, 3 to 4 minutes, or 4 to 5 minutes. Or, for example, the transducer 111 may be actuated for less than 10 seconds (s), e.g., 0.1-10 s, 1-2 s, 2-3 s, 3-4 s, 4-5 s, 5-6 s, 6-7 s, 7-8 s, 8-9 s, or 9-10 s. Or, for example, the transducer 111 may be actuated for more than 5 minutes (m), e.g., 5-6 m, 6-7 m, 7-8 m, 8-9 m, 9-10 m, 10-15 m, 15-20 m, or for more than 20 minutes.

In various configurations, the delivery of ultrasound energy during the treatment may be continuous or substantially continuous, e.g., without any interruptions or fluctuations in frequency, power, duty cycle and/or any other parameters. Alternatively, one or more of the frequency, power, duty cycle, or any other parameter may be modified during the treatment. For example, in some configurations, the delivery of ultrasonic energy is modulated, e.g., between on and off, or between a relatively high level and a relatively low level, so as prevent or reduce the likelihood of overheating of adjacent (e.g., targeted or non-targeted) tissue. For examples of such modulation, see U.S. Pat. No. 10,499,937 to Warnking, the entire contents of which are incorporated herein by reference.

In example configurations in which nerve tissue is to be treated, e.g., the nerves N illustrated in FIG. 2B, the transducer 111 may be positioned and configured so as to deliver ultrasonic energy through the wall of a body lumen BL that is adjacent to that nerve tissue, e.g., through the wall of the body lumen BL. In one nonlimiting example, renal nerves to be treated using the transducer 111 may be located about 0.5 mm to 8 mm (e.g., about 1 mm to 6 mm) from the inner wall of the renal artery. In other examples, nerve tissue to be treated may be located less about 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, less than 0.5 mm, or more than 8 mm from the inner wall of a body lumen in which transducer is disposed. Under control of the controller 120, the transducer 111 generates unfocused ultrasonic energy that heats any suitable nerve tissue so as to at least partially neuromodulate such nerve tissue, e.g., cause complete or partial ablation, necrosis, or stimulation of such nerve tissue. The ultrasonic energy generated by the transducer 111 may radiate radially outward so as to target the nerve tissue regardless of the radial orientation of such nerve tissue relative to the body lumen. In some configurations, the unfocused ultrasonic energy is delivered along an entire, continuous circumference of the transducer 111. In other configurations, the ultrasonic energy is emitted non-continuously or intermittently around the circumference of the transducer 111. It should be appreciated that nerve tissue, and more specifically the renal nerves, are only one example of tissue that may be treated using an ultrasound transducer. Other examples of target anatomical regions that may be treated with an ultrasound transducer 111 are described elsewhere herein.

Additional options regarding designs and uses of ultrasound transducers and catheter-based ultrasound delivery systems are provided in the following patents and published applications, the entire contents of each of which are incorporated by reference herein: U.S. Pat. Nos. 6,635,054; 6,763,722; 7,540,846; 7,837,676; 9,707,034; 9,981,108; 10,350,440; 10,456,605; 10,499,937; and PCT Publication No. WO 2012/112165.

In accordance with certain embodiments of the present technology, the piezoelectric transducer body of the ultrasound transducer comprises a hollow tube of piezoelectric material having an inner surface and an outer surface. In certain such embodiments, a first electrode is disposed on one of the inner and outer surfaces of the hollow tube of piezoelectric material, and a second electrode is disposed on the other one of the inner and outer surfaces of the hollow tube of piezoelectric material. The hollow tube of piezoelectric material can be cylindrically shaped, such that it has a circular shaped radial cross-section. In certain embodiments suitable, e.g., for renal denervation, the piezoelectric material, of which the piezoelectric transducer body is made, is lead zirconate titanate 8 (PZT8), which is also known as Navy III Piezo Material. Raw PZT transducers may be plated with layers of copper, nickel and/or gold to create electrodes on surfaces (e.g., the inner and outer surfaces) of the piezoelectric transducer body. In alternative embodiments the hollow tube of piezoelectric material can have other shapes besides being cylindrical with a circular cross-section. Other cross-sectional shapes for the hollow tube of piezoelectric material, and more generally the piezoelectric transducer body, include, but are not limited to, an oval or elliptical cross-section, a square or rectangular cross-section, pentagonal cross-section, a hexagonal cross-section, a heptagonal cross-section, an octagonal cross-section, and/or the like. In still other embodiments, the piezoelectric transducer body is not hollow, e.g., can have a generally solid rectangular shape, or some other solid shape. The piezoelectric transducer body can be configured, e.g., to deliver acoustic energy in a frequency range of 8.5 to 9.5 MHz, but is not limited thereto. In accordance with certain embodiments, the piezoelectric transducer body is configured to produce an acoustic output power within a range of 5 to 45 Watts in response to an input electrical power within a range of 10 to 80 Watts, but is not limited thereto.

Figure 4:
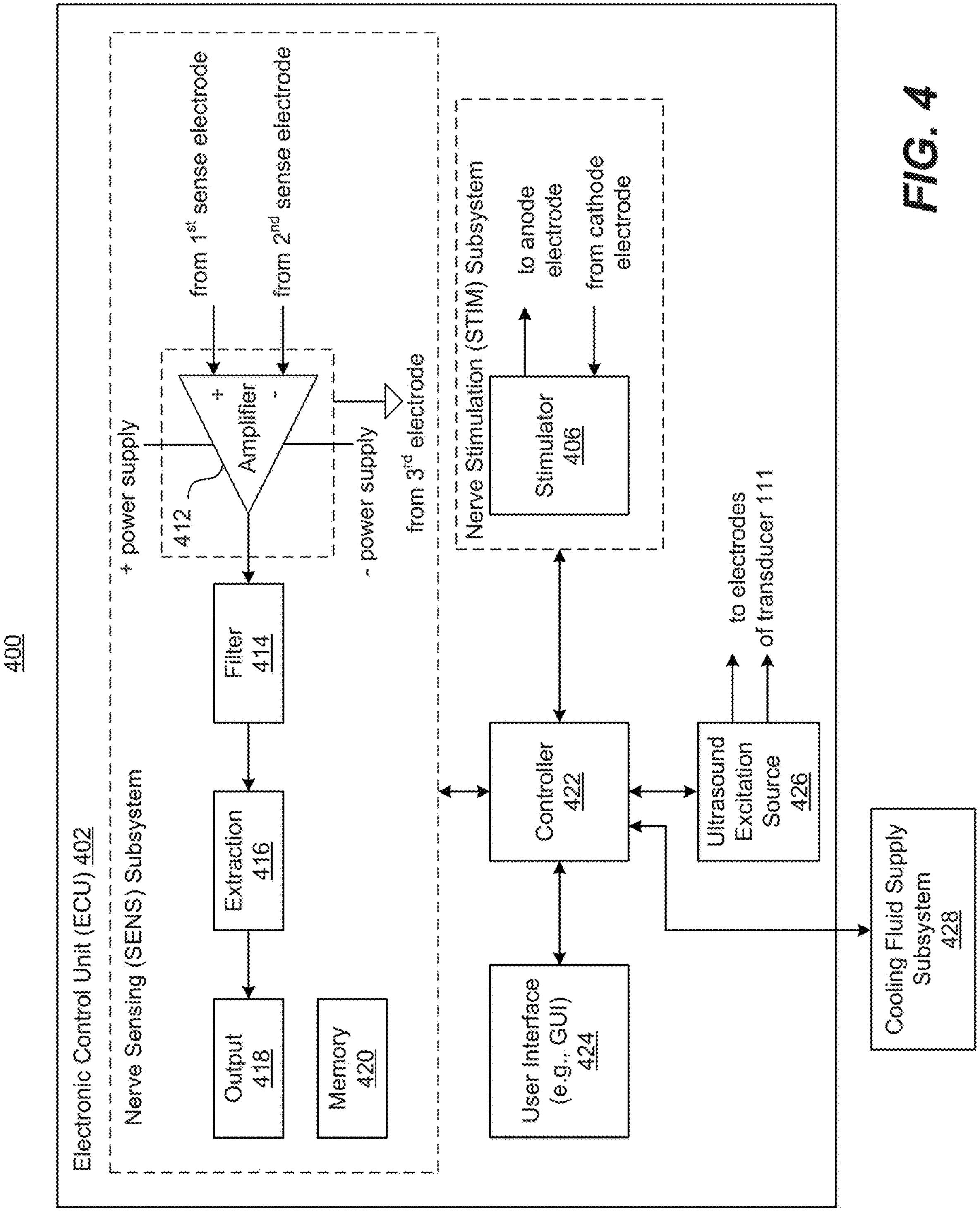
FIG. 4 is a high-level block diagram of an electronic control unit (ECU) that is configured to be in electrical communication with a catheter, such as the catheter introduced in FIGS. 1, 2A and 2B, in accordance with certain embodiments.

FIG. 4 is a high-level block diagram of an electronic control unit (ECU) 402 that is configured to be in electrical communication with a catheter, such as the catheter 102 described above. The ECU 402, and the catheter (e.g., 102) to which the ECU 402 is electrically coupled via a cable (e.g., 140), can be referred to more generally as a system 400. The ECU 402 can process a received signal to produce an output signal, and present information including information about the output signal, the received signal, or processing information. Such a system can be used, for example, in diagnostic procedures for assessing the status of a patient's nervous activity proximate a biological lumen, such as a vein or an artery, e.g., a renal artery, or another type of blood vessel.

In the illustrated embodiment of FIG. 4, the ECU 402 includes an amplifier 412 including a non-inverting (+) input terminal, an inverting (−) input terminal, a power supply input terminal, and a ground or reference terminal. As can be appreciated from FIG. 4, the non-inverting (+) input terminal is electrically coupled to a first sense electrode of the catheter and the inverting (−) input terminal is electrically coupled to a second sense electrode of the catheter, the power supply input terminal is electrically coupled to a voltage source (e.g., a reference voltage generator). Additionally, the ground or reference terminal of the amplifier 412 is electrically coupled to a further electrode, e.g., a ring or tip electrode on the catheter 102, or to a reference electrode that is located on a distal end of an introducer or that is located on the skin of the patient, but is not limited thereto.

In some embodiments, the ECU 402 can include a switching network configured to interchange which of electrodes of a catheter (e.g., 102) are coupled to which portions of the ECU. In some such embodiments, a user can manually switch which inputs receive connections to which electrodes of the catheter 102. Such configurability allows for a system operator to adjust the direction of propagation of the elicited potential as desired. For example, the switching network, or more generally switches, can be used to select which electrodes of a catheter connect to the stimulator during a period of time during which stimulation pulses are to be emitted by the catheter 102, and the switches can then be used to select which electrodes of the catheter are connected to the amplifier 412 during a period of time during which the elicited response to the stimulation pulses are to be sensed. More generally, the switching network can be used to select which two or more electrodes of a catheter are being used as sense electrodes, and which two or more electrodes of the catheter are being used as stimulation electrodes. It is noted that one or more electrodes that are used as stimulation electrodes during a period of time can be used as sense electrodes during another period of time, and/or vice versa.

The amplifier 412 can include any appropriate amplifier for amplifying desired signals or attenuating undesired signals. In some examples, the amplifier has a high common-mode rejection ratio (CMRR) for eliminating or substantially attenuating undesired signals present at the sensing electrodes. In some embodiments, the amplifier 412 can be adjusted, for example, via an adjustable capacitance or via other attributes of the amplifier.

In the example system 400 of FIG. 4, the ECU 402 further includes a filter 414 for enhancing the desired signal in the signal received via the sense electrodes. The filter 414 can include a band-pass filter, a notch filter, or any other appropriate filter to isolate desired signals from the received signals. In some embodiments, various properties of the filter 414 can be adjusted to manipulate its filtering characteristics. For example, the filter may include an adjustable capacitance or other parameter to adjust its frequency response.

At least one of amplification and filtering of the signal received at the sense electrodes can allow for extraction of the desired signal at 416. In some embodiments, extraction 416 comprises at least one additional processing step to isolate desired signals from the signal sensed using the sense electrodes such as preparing the signal for output at 418. In some embodiments, the functionalities of any combination of amplifier 412, filter 414, and extraction 416 may be combined into a single entity. For instance, the amplifier 412 may act to filter undesired frequency content from the signal without requiring additional filtering at a separate filter.

In some embodiments, the ECU 402 can record emitted stimuli and/or received signals. Such data can be subsequently stored in permanent or temporary memory 420. The ECU 402 can comprise such memory 420 or can otherwise be in communication with external memory (not shown). Thus, the ECU 402 can be configured to emit stimulus pulses to electrodes of the catheter, record such pulses in a memory, receive signals from the catheter, and also record such received signal data. The memory 420 in or associated with the ECU 402 can be internal or external to any part of the ECU 402 or the ECU 402 itself.

The ECU 402 or separate external processor can further perform calculations on the stored data to determine characteristics of signals either emitted or received via the catheter. For example, in various embodiments, the ECU 402 can determine any of the amplitude, duration, or timing of occurrence of the received or emitted signals. The ECU 402 can further determine the relationship between the received signal and the emitted stimulus signal, such as a temporal relationship therebetween. In some embodiments, the ECU 402 performs signal averaging on the signal data received from the catheter. Such averaging can act to reduce random temporal noise in the data while strengthening the data corresponding to any elicited potentials received by the catheter.

Averaging as such can result in a signal in which temporally random noise is generally averaged out and the signal present in each recorded data set, such as elicited potentials, will remain high. In some embodiments, each iteration of the process can include a synchronization step so that each acquired data set can be temporally registered to facilitate averaging the data. That is, events that occur consistently at the same time during each iteration may be detected, while temporally random artifacts (e.g., noise) can be reduced. In general, the signal to noise ratio (SNR) resulting in such averaging will improve by the square root of the number of samples averaged in order to create the averaged data set.

The ECU 402 can further present information regarding any or all of the applied stimulus, the signal, and the results of any calculations to a user of the system, e.g., via output 418. For example, the ECU 402 can generate a graphical display providing one or more graphs of signal strength vs. time representing the stimulus and/or the received signal.

In some embodiments, the ECU 402 can include a controller 422 in communication with one or both of stimulator 406 and SENS subsystem 410. The controller 422 can be configured to cause stimulator 406 to apply a stimulation signal to a catheter, e.g., the catheter 102. Additionally or alternatively, the controller 422 can be configured to analyze signals received and/or output by the SENS subsystem 410. In some embodiments, the controller 422 can act to control the timing of applying the stimulation signal from stimulator 406 and the timing of receiving signals by the SENS subsystem 410. The controller 422 can be implemented, e.g., using one or more processors, field programmable gate arrays (FPGAs), state machines, and/or application specific integrated circuits (ASICs), but is not limited thereto.

Example electrical control units have been described. In various embodiments, the ECU 402 can emit stimulus pulses to the catheter 102, receive signals from the catheter 102, perform calculations on the emitted and/or received signals, and present the signals and/or results of such calculations to a user. In some embodiments, the ECU 402 can comprise separate modules for emitting, receiving, calculating, and providing results of calculations. Additionally or alternatively, the functionality of controller 422 can be integrated into the ECU 402 as shown, or can be separate from and in communication with the ECU.

The catheter 102, according to an embodiment of the present technology, is configured to be introduced into a biological lumen, such as an artery, in a location near a body organ, such as a kidney. The catheter 102 can be introduced via a sheath that is advanced to the intended catheter location in the biological lumen, and then withdrawn sufficiently to expose the shaft 214 to the biological lumen (e.g., renal artery).

For example, where the catheter is inserted into a renal artery close to a kidney, the electrodes can be positioned near a nerve bundle that connects the kidney to the central nervous system, as the nerve bundle tends to approximately follow the artery leading to most body organs. The nerve bundle tends to follow the artery more closely at the end of the artery closer to the kidney, while spreading somewhat as the artery expands away from the kidney. As a result, it is desired in some examples that the catheter shaft 214 is small enough to introduce relatively near the kidney or other organ, as nerve proximity to the artery is likely to be higher nearer the organ.

Once the catheter 102 is in place, a practitioner can use instrumentation (e.g., the ECU 402) coupled to stimulation electrodes to stimulate the nerve, and monitor for nerve response signals used to characterize the nervous system response to certain stimulus. In some embodiments, an ablation element (not shown) is included in or on the shaft and configured to ablate nerve tissue, such as by using radio frequency, microwave, cryotherapy, ultrasound, or other energy, such that the catheter can actively stimulate the nerve and sense resulting neural signals in between applications of energy via the ablation element, enabling more accurate control of the degree and effects of nerve ablation. In other examples, a catheter 102 lacking an ablation element can be removed via the sheath, and an ablation probe inserted, with the ablation probe removed and the catheter 102 reinserted to verify and characterize the effects of the ablation probe.

The ECU 402 includes a nerve sensing (SENS) subsystem and a nerve stimulation (STIM) subsystem. The ECU 402 also includes an ultrasound excitation source 426, and a user interface 424. In FIG. 4, the controller 422 is also shown as being communicatively coupled to a cooling fluid supply subsystem 428. Such a system 400 can be used, for example, in both diagnostic procedures and treatment procedures. The diagnostic procedures can be used for assessing the status of a patient's nervous activity proximate a biological lumen, such as a vein or an artery, e.g., a renal artery, or another type of blood vessel. The treatment procedures can be used to neuromodulate (e.g., fully or partially ablate, necrose, or stimulate) the nerve tissue that surrounds such a biological lumen.

The user interface 424 interacts with the controller 422 (and more specifically, e.g., a processor thereof) to cause transmission of electrical signals at selected actuation frequencies to the transducer 111. Wires or other types of electrically conductive traces can electrically couple the transducer 111 to the excitation source 426 of the ECU 402, to thereby enable the controller 422 to control the excitation source 426 to control the amplitude and timing of the electrical signals so as to control the power level and duration of the ultrasound signals emitted by transducer 111. More generally, the controller 422 can control one or more ultrasound treatment parameters that are used to perform sonication. In certain embodiments, the SENS subsystem can also detect electrical signals generated by transducer 111 and communicate such signals to the controller 422. While the ultrasound excitation source 426 in FIG. 4 is shown as being part of the ECU 402, it is also possible that the ultrasound excitation source 426 is external to the ECU 402 while still being controlled by the controller 422. It is also noted that a different type of transducer can be used, such as, but not limited to, a radio frequency (RF) or microwave transducer, in which cases a different excitation source 426 may be used.

The user interface 424 can include a touch screen and/or buttons, switches, etc., to allow for an operator (aka user) to enter patient data, select a treatment parameters, view records stored on a storage/retrieval unit (not shown), and/or otherwise communicate with the controller 422. The user interface 424 can include a voice-activated mechanism to enter patient data or may be able to communicate with additional equipment so that control of the controller 422 is through a separate user interface, such as a wired or wireless remote control. In some embodiments, the user interface 424 is configured to receive operator-defined inputs, which can include, e.g., a duration of energy delivery, one or more other timing aspects of the energy delivery pulses (e.g., frequency, duty cycle, etc.), power, and/or mode of operation, or a combination thereof. Example modes of operation can include (but are not limited to): system initiation and set-up, catheter preparation, balloon inflation, verification of balloon apposition, pre-cooling, sonication, post-cooling, balloon deflation, and catheter removal, but are not limited thereto. In certain embodiments, the user interface 424 provides a graphical user interface (GUI) that instructs a user how to properly operate the system 400. The user interface 424 can also be used to process and/or display treatment data for review and/or download, as well as to allow for software updates, and/or the like.

Figure 5:
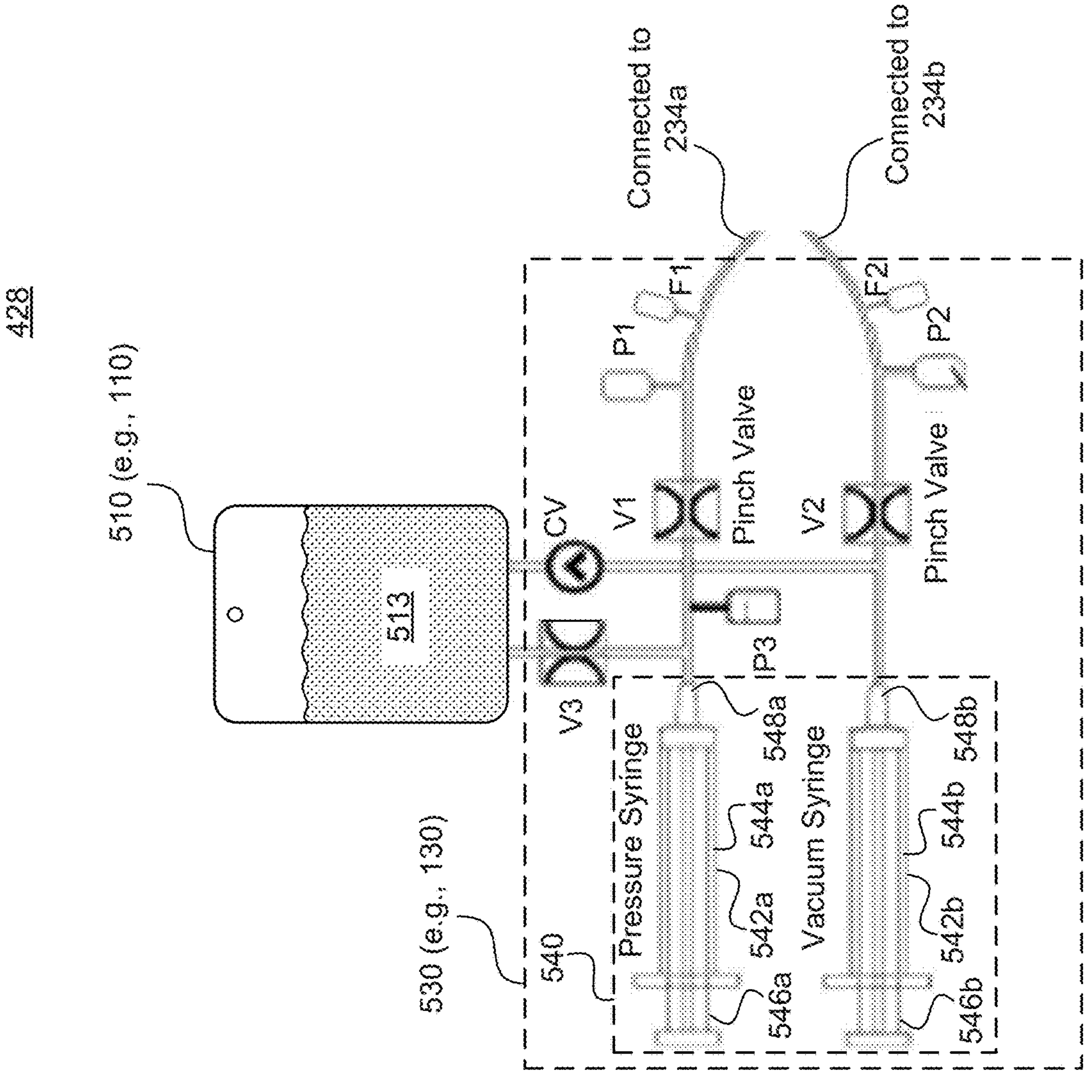
FIG. 5 illustrates example details of a cooling fluid supply subsystem of a tissue treatment system, in accordance with certain embodiments.

The controller 422 can also control a cooling fluid supply subsystem 428, which can include a cartridge and a reservoir, which are described below with reference to FIG. 5, but can include alternative types of fluid pumps, and/or the like. The cooling fluid supply subsystem 428 is fluidically coupled to one or more fluid lumens (e.g., 327, 328, in FIGS. 9A, 9B) within the catheter shaft 214 which in turn are fluidically coupled to the balloon 112. The cooling fluid supply subsystem 428 can be configured to circulate a cooling liquid through the catheter shaft 214 to the transducer 111 in the balloon 112.

Example details of the cooling fluid supply subsystem 428, which were introduced above in the above discussion of FIG. 4, will now be described with reference to FIG. 5. Referring to FIG. 5, the cooling fluid supply subsystem 428 is shown as including a cartridge 530 (e.g., 130) and a reservoir 510 (e.g., 110). The reservoir 510 is shown as being implemented as a fluid bag, which can be the same or similar to an intravenous (IV) bag in that it can hang from a hook, or the like. The reservoir 510 and the cartridge 530 can be disposable and replaceable items.

The reservoir 510 is fluidically coupled to the cartridge 530 via a pair of fluidic paths, one of which is used as a fluid outlet path (that provides fluid from the reservoir to the cartridge), and the other one of which is used as a fluid inlet path (the returns fluid from the cartridge to the reservoir). The cartridge 530 is shown as including a syringe pump 540, which includes a pressure syringe 542*a* and a vacuum syringe 542*b*. The pressure syringe 542*a* includes a barrel 544*a*, a plunger 546*a*, and a hub 548*a*. Similarly, the vacuum syringe 542*b* includes a barrel 544*b*, a plunger 546*b*, and a hub 548*b*. The hub 548*a*, 548*b* of each of the syringes 542*a*, 542*b* is coupled to a respective fluid tube or hose. The cartridge 530 is also shown as including pinch valves V1, V2 and V3, pressure sensors P1, P2, and P3, and a check valve CV. While not specifically shown in FIG. 5, the syringe pump 540 can include one or more gears and step-motors, and/or the like, which are controlled by the controller 422 (in FIG. 4) to selectively maneuver the plungers 546 of the pressure syringe 542*a* and the vacuum syringe 542*b*. Alternatively, the gear(s) and/or step-motor(s) can be used to control the syringe pump 540.

In order to at least partially fill the barrel of the pressure syringe 542*a* with a portion of the cooling fluid that is stored in the reservoir 510, the pinch valves V1 and V2 are closed, the pinch valve V3 is opened, and the plunger 546*a* of the pressure syringe 542*a* is pulled upon to draw cooling fluid 513 into the barrel 544*a* of the of the pressure syringe 542*a*. The pinch valve V3 is then closed and the pinch valves V1 and V2 are opened, and then the plunger 546*a* of the pressure syringe 542*a* is pushed upon to expel cooling fluid from the barrel 544*a* of the pressure syringe 542*a* through the fluid tube attached to the hub 548*a* of the pressure syringe 542*a*. The cooling fluid expelled from the pressure syringe 542*a* enters a fluid lumen (e.g., 327 in the catheter shaft 214), via the fluidic inlet port 234*a* of the catheter 102, and then enters and at least partially fills the balloon 112. Simultaneously, the plunger 546*b* of the vacuum syringe 542*b* can be pulled upon to pull or draw cooling fluid from the balloon 112 into a fluid lumen (e.g., 904*b* in the catheter shaft 214), through the fluidic outlet port 234*b* of the catheter 102, and then through fluid tube attached to the hub 548*b* of the vacuum syringe 542*b* and into the barrel 544*b* of the vacuum syringe 542*b*. In this manner, the cooling fluid can be circulated through the balloon 112. The balloon 112 can be inflated by supplying more cooling fluid to the balloon than is removed from the balloon. One or more of the pressure sensors P1, P2, and P3 can be used to monitor the pressure in the balloon 112 to achieve a target balloon pressure, e.g., of 10 pounds per square inch (psi), but not limited thereto. Once the balloon 112 is inflated to a target pressure, e.g., 10 psi, and/or size, the cooling fluid can be circulated through the balloon 112 without increasing or decreasing the amount of fluid within the balloon by causing the same amount of fluid that is removed from the balloon 112 to be the same as the amount of fluid that is provided to the balloon 112. Also, once the target balloon pressure is reached, the ultrasound transducer 111 can be excited to emit ultrasound energy to treat tissue that surrounds the portion of the body lumen (e.g., a portion of a renal artery) in which the balloon 112 and the transducer 111 are inserted. When the ultrasound transducer 111 is emitting ultrasound energy it can also be said that the ultrasound transducer 111 is performing sonication, or that sonication is occurring. During the sonication, cooling fluid should be circulated through the balloon 112 by continuing to push on the plunger 546*a* of the pressure syringe 542*a* and continuing to pull on the plunger 546*b* of the vacuum syringe 542*b*.

After the sonication is completed, and the balloon 112 is to be deflated so that the catheter 102 can be removed from the body lumen, the cooling fluid should be returned from the barrel 544*b* of the vacuum syringe 542*b* to the reservoir 510. In order to return the cooling fluid from the barrel 544*b* of the vacuum syringe 542*b* to the reservoir 510, the pinch valves V1, V2, and V3 are all closed, and the plunger 546*b* of the vacuum syringe 542*b* is pushed on to expel the cooling fluid out of the barrel of the vacuum syringe 542*b*, past the check valve CV, and into the reservoir 510.

The pressure sensors P1, P2, and P3 can be used to monitor the fluidic pressure at various points along the various fluidic paths within the cartridge 530, which pressure measurements can be provided to the controller 422 as feedback that is used for controlling the syringe pump 540 and/or for other purposes, such as, but not limited to, determining the fluidic pressure within the balloon 112. Additionally, flow rate sensors F1 and F2 can be used, respectively, to monitor the flow rate of the cooling fluid that is being injected (aka pushed, provided, or supplied) into the balloon 112, and to monitor the flow rate of the cooling fluid that is being drawn (aka pulled or removed) from the balloon 112. The pressure measurements obtained from the pressure sensors P1, P2, and P3 can be provided to the controller 422 so that the controller 422 can monitor the balloon pressure. Additionally, flow rate measurements obtained from the flow rate sensors F1 and F2 can be provided to the controller 422 so that the controller 422 can monitor the flow rate of cooling fluid being pushed into and pulled from the balloon 112. It would also be possible for one or more pressure sensors and/or flow rate sensors to be located at additional or alternative locations along the fluidic paths that provide cooling fluid to and from the balloon 112.

Figure 6B:
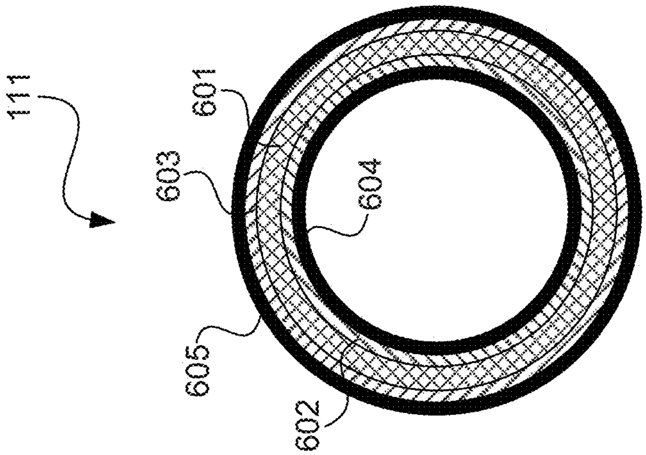
FIGS. 6A and 6B illustrate, respectively, a longitudinal cross-sectional view and a radial cross-sectional view of an example embodiment of the transducer of the catheter introduced in FIGS. 1, 2A and 2B, in accordance with certain embodiments.
Figure 6A:
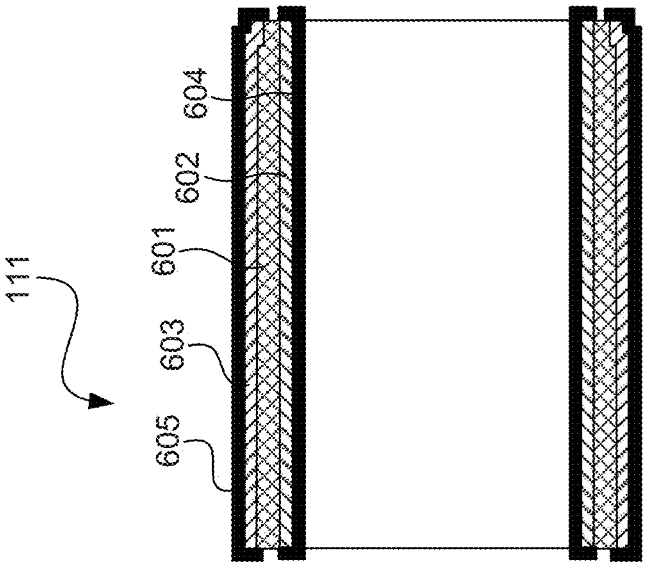

FIGS. 6A and 6B illustrate, respectively, a longitudinal cross-sectional view and a radial cross-sectional view of an example embodiment of the transducer 111 of the catheter 102 introduced above in the discussion of FIGS. 1, 2A and 2B, in accordance with certain embodiments of the present technology. The transducer 111 includes a piezoelectric transducer body 601 that comprises a hollow tube of piezoelectric material having an inner surface and an outer surface, with an inner electrode 602 disposed on the inner surface of the hollow tube of piezoelectric material, and an outer electrode 603 disposed on the outer surface of the hollow tube of piezoelectric material. The hollow tube of piezoelectric material, or more generally the piezoelectric transducer body 601, is cylindrically shaped and has a circular radial cross-section. However, in alternative embodiments the transducer body 601 can have other shapes besides being cylindrical with a circular radial cross-section. In FIGS. 6A and 6B, the inner electrode 602 is covered by an electrical insulator 604, and the outer electrode 603 is covered by an electrical insulator 605. It is also possible that only one of the electrodes 602, 603 is covered by an electrical insulator, or that neither of the electrodes 602, 603 is covered by an electrical insulator.

Figure 7:
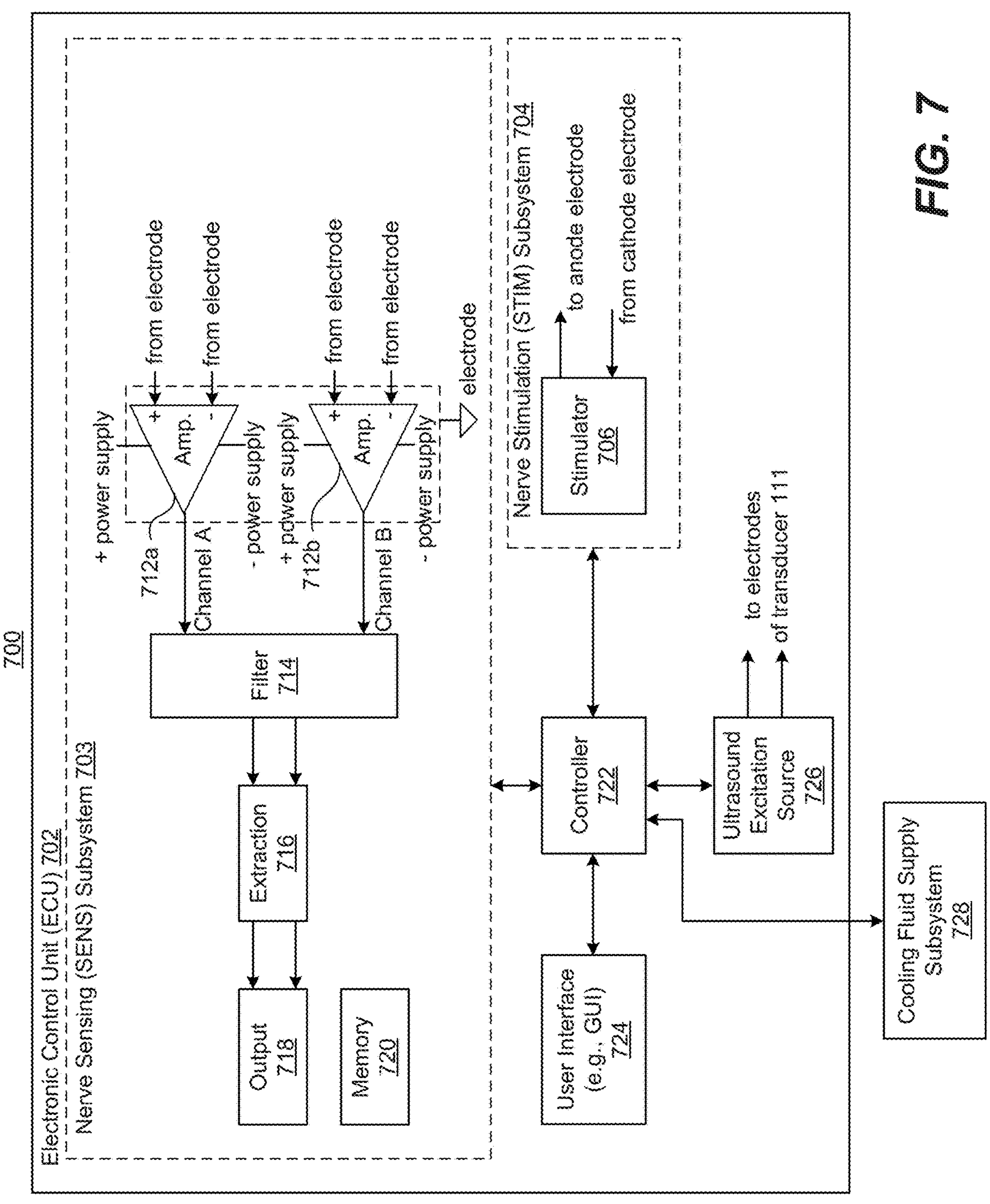
FIG. 7 is used to describe certain embodiments that provide for multi-channel sensing capabilities, which embodiments can be used where a catheter includes at least four electrodes that can be used for sensing.

FIG. 7 is used to describe certain embodiments that provide for multi-channel sensing capabilities, which embodiments can be used where the catheter 102 includes at least four electrodes that can be used for sensing. Referring to FIG. 7, a system 700 is shown as including an ECU 702, which includes a nerve sensing subsystem 703 and a nerve stimulation subsystem 704. The ECU 702 is also shown as including a controller 722, a GUI 724 and an optional excitation source 726. The system 700 can also include an optional cooling fluid supply subsystem 728. The controller 722, GUI 724, excitation source 726, and cooling fluid supply subsystem 728, operate similarly to the commonly named components described above with reference to FIG. 4, and thus, need not be described again.

In the embodiment of FIG. 7, the nerve sensing subsystem 703 can be referred to more specifically as a multi-channel nerve sensing subsystem 703, because it includes multiple channels, as will be described below. A first channel (which can also be referred to as channel 1, or channel A) includes a first amplifier 712*a*, and a second channel (which can also be referred to as channel 2, or channel B) includes a second amplifier 712*b*. The signal output by the first amplifier 712*a* can be referred to as a first channel signal, and the signal output by the second amplifier 712*b* can be referred to as a second channel signal. By contrast, referring briefly back to FIGS. 4 and 10, the nerve sensing subsystems shown therein can be referred to as single channel nerve sensing subsystems, since there is only a single amplifier 412 that outputs a single signal in those systems.

A benefit of using multi-channel sensing is that it enables additional information to be extracted from sensed signals, compared to if single-channel sensing is used. For example, with multi-channel sensing, the signals sensed by different channels can be compared to one another, to enable nerve depths to be quantified, to provide for better discrimination between sensed neural activity originating from afferent nerve fibers and sensed neural activity originating from efferent nerve fibers, and to enable nerve type identification. Additionally, by knowing the distances between the various electrodes that are used to simultaneously sense signals using multiple channels, nerve transmission velocities can be better quantified compared to if single-channel sensing is used.

Additionally, multi-channel sensing can be used to reduce and preferably eliminate noise in sensed signals. For example, two signals sensed by two different channels can be compared to one another to identify signal features (which can be temporal features and/or frequency features) that are common to both of the signals. In other words, noise common to both a first channel signal and a second channel signal can be filtered out, while first signal components unique to the first channel signal, and second signal components unique to the second channel signal, can be retained. As will be appreciated from the following discussion, each channel includes a respective differential amplifier that outputs a respective channel signal indicative of a difference between voltages at the differential inputs of the differential amplifier. Accordingly, a difference between the two channel signals sensed by two different channels is essentially a difference of differences, which difference of differences can be determined and used by an extraction module (1316) of the ECU 702 described below with reference to FIG. 8.

Referring again to FIG. 7, the first amplifier 712*a* of the first channel, and the second amplifier 712*b* of the second channel, are each shown as having a non-inverting (+) input terminal, an inverting (−) input terminal, an output terminal, power supply terminals and a ground reference terminal. The non-inverting (+) input terminal, the inverting (−) input terminal and the output terminal, can be referred to more succinctly herein as the non-inverting (+) input, the inverting (−) input and the output, respectively. It is also noted that the non-inverting (+) input and the inverting (−) input of an amplifier can also be referred to herein as a pair of inputs of the amplifier.

In accordance with certain embodiments, as shown in FIG. 7, in order to provide for multi-channel sensing, the inverting (−) inputs of the two amplifiers 712*a*, 712*b* are electrically coupled the same electrode, the ground reference terminals of the two amplifiers 712*a*, 712*b* are electrically coupled to the same electrode, and the non-inverting (+) input of the first amplifier 712*a* and the non-inverting (+) input of the second amplifier 712*b* are electrically coupled to different ones of a pair of electrodes. A benefit of having the inverting (−) inputs of the two amplifiers 712*a*, 712*b* electrically coupled the same electrode is that it eliminates bias that would otherwise occur if the inverting (−) inputs of the two amplifiers 712*a*, 712*b* were coupled to different electrodes than one another. Nevertheless, it would also be possible for the inverting (−) inputs of the two amplifiers 712*a*, 712*b* to instead be electrically coupled to different electrodes that one another to create a decoupled reference, which may be useful if the different electrodes coupled to the inverting (−) inputs of the two amplifiers 712*a*, 712*b* span an ablation lesion. A benefit of having the ground reference terminals of the two amplifiers 712*a*, 712*b* electrically coupled to the same electrode is that it introduces an identical ground reference, which provides for increased confidence in signal reliability. Nevertheless, although less preferred, it would also be possible for the ground reference terminals of the two amplifiers 712*a*, 712*b* to be electrically coupled to different electrodes than one another.

More generally, in accordance with certain embodiments, each of the amplifiers 712*a*, 712*b* includes a respective ground reference terminal that is coupled to a same ground reference electrode. In accordance with certain embodiments, the ground reference electrode comprises one of the electrodes of the catheter that is not electrically coupled to any of the inputs of the amplifiers 712*a*, 712*b*. In accordance with certain embodiments, the ground reference electrode comprises one of an external surface electrode configured to be placed against skin of a patient, or an external needle electrode configured to be placed into skin of a patient.

While not specifically shown in FIG. 7, so as to not overly complicate the figure, the ECU 702 can include switches (e.g., transistor switches, multiplexers, or relays, but not limited thereto) that can be controlled (e.g., by the controller 722) to select which electrodes, at any given time, are electrically coupled to the various terminals of the amplifiers 712*a*, 712*b* and the stimulator 706.

In accordance with certain embodiments, the same electrodes used to deliver the stimulation pulse(s) during a first period of time, can also be used to sense the evoked neural response to the stimulation pulse(s) during a second period of time. In accordance with certain embodiments, in order to mitigate the chance that such electrodes are polarized during the second period of time, as well as to prevent the amplifiers 712*a* and 712*b* from being saturated during the second period of time, deblocking and/or switching can be performed to isolate the amplifiers 712*a* and 712*b* during the first period of time that the stimulation pulse(s) is/are delivered, as well as for a short temporal window (e.g., a 15 millisecond window) following deliver of the stimulation pulse(s).

As can be appreciated from the above discussion, the nerve sensing subsystem 703 can be used to sense an evoked neural response to one or more electrical stimulation pulses delivered using the nerve stimulation subsystem 704. However, it is also noted that the nerve sensing subsystem 703 can also be used to sense native electrical neural activity, if so desired.

As shown in FIG. 7, the signals output by the first and second amplifiers 712*a*, 712*b*, which can be referred to as the first channel signal (or signal A, or signal 1) and the second channel signal (or signal B, or signal 2), are shown as being provided to filter module 714, and outputs of the filter circuitry 714 are shown as being provided to extraction circuitry 716. The filter circuitry 714, which can also be referred to as a filter module 714 or more succinctly as a filter 714, is used to remove noise and other signal components that are not of interest. The extraction circuitry 716, which can also be referred to as an extraction module 716, is used to extract information of interest from filtered signals received from the filter module 714. More generally, the filter circuitry 714 and the extraction module 716 collectively provide for signal processing of the multi-channel signals output 718 by the first and second amplifiers 712*a*, 712*b*. Additional details of the filter circuitry 714 and the extraction circuitry 716, according to certain embodiments of the present technology, are described below with reference to FIG. 8.

As noted above, the filter circuitry 714 is used to remove noise and other signal components that are not of interest. Additional details of the filter circuitry, according to specific embodiments of the present technology, are described below with reference to FIG. 8. In some embodiments, various properties of the filter circuitry 714 can be adjusted to manipulate its filtering characteristics. For example, the filter module may include one or more adjustable capacitances and/or other parameter(s) to adjust its frequency response.

Figure 8:
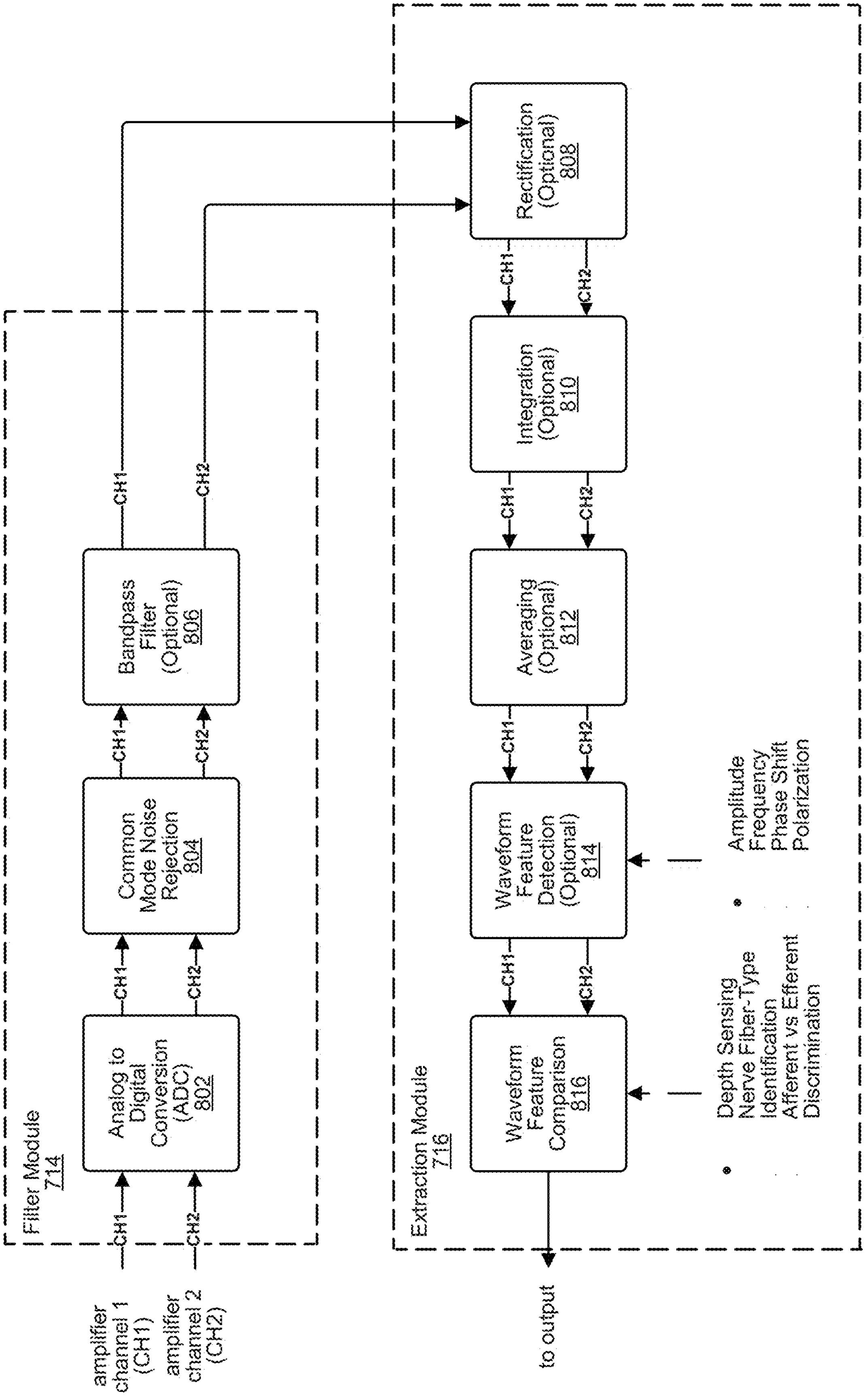
FIG. 8 provides additional details of the filter module and extraction module, introduced in FIG. 7, according to certain embodiments.

Referring now to FIG. 8, the filter circuitry 714 is shown as including a multi-channel analog-to-digital converter (ADC) 802, common noise rejection circuitry 804, and optional bandpass filter circuitry 806. The multi-channel ADC 802 converts the analog signals output by the first and second amplifiers 712*a*, 712*b* to digital signals, so that the multi-channel signals can be processed in the digital domain, using digital signal processing. While the multi-channel ADC 802 is shown as being part of the filter module 714, it would be equivalent for the multi-channel ADC 802 to be located upstream of the filter module 714, i.e., between the outputs of the first and second amplifiers 712*a*, 712*b* and inputs to the filter module 714. It is also noted that two separate ADCs, that are preferably commonly grounded, can be used in place of the multi-channel ADC 802.

In accordance with certain embodiments, the common noise rejection circuitry 804, which can also be referred to as the common noise rejection module 804, includes one or more digital notch filters that filter out noise, intrinsic to the channels, that is within the bandwidth of interest. Noise intrinsic to the channels, which is attenuated using one or more notch filters, can be noise from a known source of noise, such as line noise, but is not limited thereto. An example frequency range that such one or more notch filters can be used to attenuate is from 50 Hz to 60 Hz, but is not limited thereto. It is also noted that each of the differential amplifiers 712*a* and 712*b* provides for common noise rejection.

The common noise rejection circuitry 804 can additionally be used to identify signal components of the first and second channel signals that are the same, and/or to identify signal components of the first and second channel signals that differ from one another, depending upon the specific implementation. Examples of type of signal components of the first and second channel signals, which can differ from one another, include signal phases and signal amplitudes, but are not limited thereto. Differences between phases of the first and second channel signals can be due to a longitudinal distance between electrodes used to sense the first and second channel signals. For example, signal phases may differ between the first and second channel signals due to a longitudinal distance between first and second deployable electrodes used, respectively, to sense the first and second channel signals. Signal amplitudes may differ between the first and second channel signals due to variations of the depths of nerve fibers and/or nerve bundles relative to a wall of a biological lumen in which sensing electrodes are located. For example, if nerve fibers are located closer to a portion of the wall of a biological lumen that a first deployable electrode is in contact with, than are nerve fibers located in a portion of the wall of the biological lumen that a second deployable electrode is in contact with, then amplitudes of the first channel signal may be greater than amplitudes of the second channel signal. For the below discussion, it is assumed that noise common to both the first and second channel signals is removed by the common mode noise rejection module 804, such that the first and second channel signals output from the common noise rejection module are substantially devoid of such common noise.

The optional bandpass filter circuitry 806, which can also be referred to as the bandpass filter module 806, if present, attenuates frequencies outside a bandwidth of interest. Explained another way, the bandpass filter circuitry 806 is configured to filter out frequency components of the first and second channel signals outside the bandwidth of interest, and to pass frequency components of the first and second channel signals within the bandwidth of interest. The bandwidth of interest, which is passed by the bandpass filter circuitry 806, can be, e.g., from 150 Hz to 2 kHz, but is not limited thereto. In certain embodiments, each bandpass filter can be implemented by a combination of a low pass filter (that filters out frequencies above an upper limit of the bandpass of interest) followed by a high pass filter (that filters out frequencies below a lower limit of the bandpass of interest), or by one filter that passes frequencies between the lower and upper limits of interest and filters out, aka rejects, frequencies below the lower limit of the bandpass of interest and above the upper limit of the bandpass of interest. The first and second channel signals, which are provided from the filter module 714 to the extraction module 716, can be referred to more specifically herein as filtered first and second channel signals, or equivalently as first and second channel filtered signals.

As noted above, the extraction module 716 is used to extract information of interest from filtered signals received from the filter module 714. Examples of information that can be extracted from the filtered signals include nerve depth information related to the depth of nerves of interest (e.g., renal nerves), nerve fiber type information which can be used to identify nerve fiber types (e.g., A, B, or C type fibers), and discrimination information which can be used to distinguish afferent nerves from efferent nerves, but are not limited thereto.

Nerves can be classified as afferent or efferent depending on the direction in which information travels, with afferent nerves carrying information from an organ (such as a kidney) to the central nervous system (i.e., brain and spinal cord), and efferent nerves carrying information from the central nervous system to an organ (such as a kidney). If a common signal component (e.g., a common evoked neural response component) appears in both the first channel filtered signal and the second channel filtered signal, then the relative phase of the signals can be used to determine whether the signal component originated from either an afferent nerve or an efferent nerve. For a more specific example, if a common evoked neural response component appears in the first channel signal (sensed using a distal deployable electrode) prior to appearing in the second channel signal (sensed using a proximal deployable electrode), then it can be determined that the nerves (whose evoked neural response was sensed) are afferent nerves. Conversely, if a common evoked neural response component appears in the second channel signal (sensed using the proximal deployable electrode) prior to appearing in the first channel signal (sensed using the distal deployable electrode), then it can be determined that the nerves (whose evoked neural response was sensed) are efferent nerves. Morphological analysis can be used to determine whether evoked neural response components included in both the first and second channel signals are a common evoked neural response component. Time stamps, and/or the like, can be used to determine which of the channels a common evoked neural response component initially appears in for the purpose of determining whether the signal component originated from either an afferent nerve or an efferent nerve.

A velocity of a sensed neural signal can be determined based on a time delay between when a common evoked neural response component appears in the second channel signal (sensed using the proximal deployable electrode) and when the common evoked neural response component appears in the first channel signal (sensed using the distal deployable electrode), and knowing the distance between the proximal deployable electrode and the distal deployable electrode. More specifically, since velocity is a rate of change of position with respect to time, the velocity of a neural signal can be determined by dividing the distance between the proximal deployable electrode and the distal deployable electrode, by the time delay between when a common evoked neural response component appears in the second channel signal (sensed using the proximal deployable electrode) and when the common evoked neural response component appears in the first channel signal (sensed using the distal deployable electrode). This is just one example, which is not intended to be all encompassing. Since different nerve fibers carry information at different speeds (aka velocities), the determined velocity of a neural response can be used to identify (aka classify) a type of nerve fiber from which the neural response originated. Accordingly, for example, if there is a desire to identify where C type nerve fibers are positioned about a biological lumen, so that the C type nerve fibers can be targeted for a denervation procedure, then embodiments of the present technology described herein can be used to identify where C type nerve fibers are located. Example details of selectively deployable distal and proximal electrodes are discussed below with reference to FIGS. 9A through 16.

Still referring to FIG. 8, the extraction module 716 is shown as including rectification circuitry 808, integration circuitry 810, averaging circuitry 812, waveform feature detection circuitry 814, and waveform feature comparison circuitry 816. As can be appreciated from FIG. 8, some of the above types of circuitry of the extraction module, which circuitry can also be referred to as modules, is optional. The rectification module 808, if present, rectifies each of the filtered first and second channel signals. The integration module 810, if present, integrates (aka sums) the filtered (and optionally also rectified) first and second channel signals. The averaging module 812, if present, takes several inputs over a period, t0 to tn, and sums then divides by the number to time points to arrive at a signal average. This methodology eliminates random variation from the primary signal. Beneficially, the averaging module 812 smooths out spikes and higher frequency signals when comparing multiple data windows referencing an event, such as, a stimulation or a heartbeat. This assists in signal analysis by reducing noise and allows repetitive, strong signals to be visualized.

The waveform detection module 814, if present, can be used to detect waveform features of the processed (e.g., filtered, rectified, integrated and/or averaged) first and second channel signals. Such waveform features, which can be detected by the waveform detection module 814, include, but are not limited to, amplitudes, frequency components, phase shifts, polarizations, and/or the like. The waveform feature comparison module 816 compares the first and second channel signals, and/or the features thereof already detected by the waveform feature detection module 814, and outputs information determined based on the comparison. The information output by the waveform feature comparison module 816 can include, e.g., nerve depth information related to the depth of nerves of interest (e.g., renal nerves), nerve fiber type information which can be used to identify nerve fiber types (e.g., A, B, or C type fibers), and discrimination information which can be used to distinguish afferent nerves from efferent nerves, but are not limited thereto. The nerve depth information can be determined by relative signal strengths. In certain embodiments, nerves can be polled to create a reference point based upon a known depth. Alternatively, a signal can be emitted using one or more electrodes from a distant point (e.g., in the abdominal aorta) and then one or more further electrodes can be used to listen for signals from known nerve depths. In certain embodiments, signal strength versus nerve depth from a reference is previously known based on direct coupling study versus depth to get a baseline from which to make inferences. The information output by the waveform feature comparison module 816 can be stored in memory 720 and/or used to display information via the GUI 724, but is not limited thereto.

More generally, in accordance with certain embodiments, the multi-channel nerve sensing subsystem 703 includes one or more analog-to-digital converters configured to convert the first and second channel signals from analog signals to digital signals, and digital signal processing circuitry configured to extract information from the first and second channel signals, based on least in part on the comparison between the first and second channel signals, after the first and second channel signals have been converted to digital signals.

In accordance with certain embodiments, the filter module 714 and the extraction module 716, and the modules thereof, can be implemented using one or more processors, which can include one or more Digital Signal Processors (DSPs).

Alternatively, or additionally, the filter module 714 and the extraction module 716, and the modules thereof, can be implemented using one or more field-programmable gate arrays (FPGAs), one or more Signal on Chip (SOCs), and/or one or more application specific integrated circuits (ASICs). More generally, the filter module 714 and the extraction module 716 can be implemented using hardware, software, firmware, and/or combinations thereof.

Balloons with Electrodes

Referring back to FIG. 2A, the catheter 102 shown therein can be referred to more specifically as a treatment catheter 102, since it is being used to neuromodulate (e.g., fully or partially ablate, or necrose) the nerve tissue that is adjacent to the transducer 111 of the catheter 102 while at least a distal portion of the catheter 102 is inserted into a biological lumen, such as the renal artery. Prior to inserting the treatment catheter 102 into the biological lumen, a separate catheter, which can be referred to as a measurement catheter, may first be inserted into the biological lumen to stimulate nerves, and monitor for nerve response signals used to characterize the nervous system response to the stimulus. Such a measurement catheter can include one or more deployable electrodes and/or one or more non-deployable electrodes which are electrically coupled to an electronic control unit (ECU). Such electrodes of the measurement catheter can be used to evoke nerve activity (e.g., renal nerve activity) by delivering stimulation, and measuring the evoked neural response thereto, in order to obtain one or more baseline measurements of neural activity prior to the treatment catheter being inserted into the biological lumen and use to perform an ablation or other neuromodulation procedure. However, this requires that the measurement catheter be inserted into the biological lumen and then removed before the treatment catheter is inserted into the biological lumen and used to perform the ablation or other neuromodulation procedure. Additionally, where there is a desire to evoke neural activity following the ablation or other neuromodulation procedure, in order to determine whether the procedure was sufficiently successful, or whether further treatment is necessary, the treatment catheter may need to be removed so that the measurement catheter can be reinserted into the biological lumen. Such exchanging (aka swapping) of the measurement catheter and the treatment catheter, which may occur a few times, can be time consuming for both the patient and the medical personnel, as well as costly to the patient in terms of increasing their medical bills. Accordingly, it would be beneficial if the same catheter that is used for treatment can also be used to obtain measurements. In other words, it would be beneficial if an all-in-one catheter could be used to eliminate the need to exchange catheters.

Certain embodiments of the present technology, which are described below, are directed to all-in-one catheters that can be used for both measuring evoke neural activity as well as performing ablation or another neuromodulation procedure. Such all-in-one catheters can be used to reduce the time it takes for an ablation or other type neuromodulation procedure to be performed by reducing and potentially eliminating the need to exchange catheters. The reduction or elimination in catheter exchanges also helps ensure the sensing of neural activity is being performed in substantially the same location that ablation is performed, because the catheter does not have to be moved to allow for the exchange.

As will be described in additional details below, such all-in-one catheters include a transducer (e.g., 111) within a balloon (e.g., 112), as was described above with reference to FIGS. 2A-2D, and also include an electrode that is distal to the transducer and an electrode that is proximal the transducer, with at least a portion of the balloon being between the distal and proximal electrodes. In some embodiments the balloon generally lies between distal and proximal electrodes. In other embodiments, the proximal and distal electrodes are in position or deployable around, within, or on the balloon or both. The proximal and distal electrodes are designed and/or positioned to not interfere with ultrasonic ablation or PZT function of the transducer.

Intussusceptable Electrodes

Figure 9A:
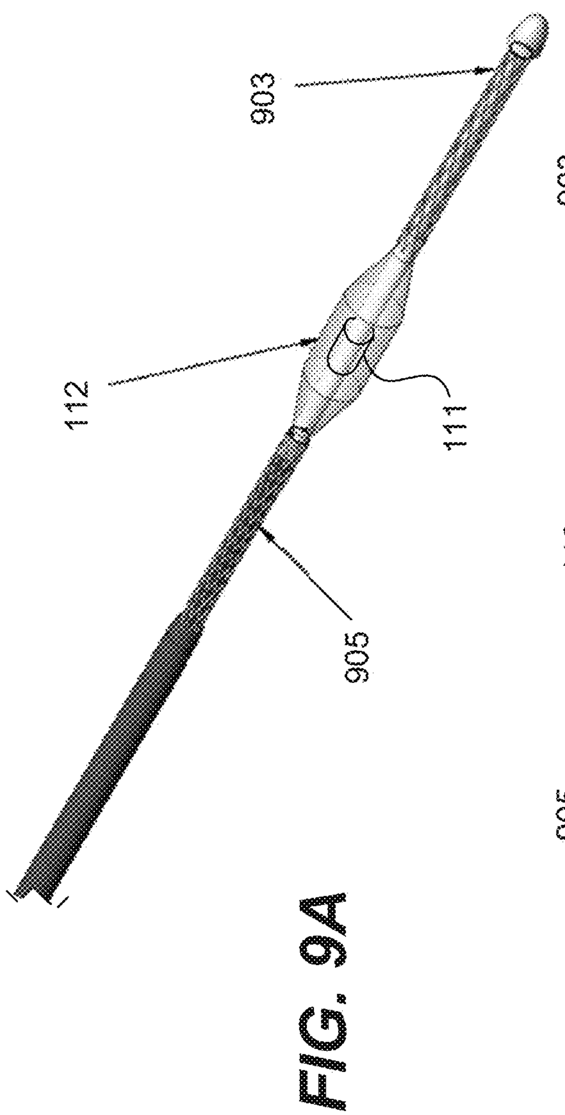
FIGS. 9A and 9B are respectively perspective and side views of a catheter shaft having selectively intussusceptable electrodes in their non-intussuscepted positions, in accordance with certain embodiments.
Figure 9B:
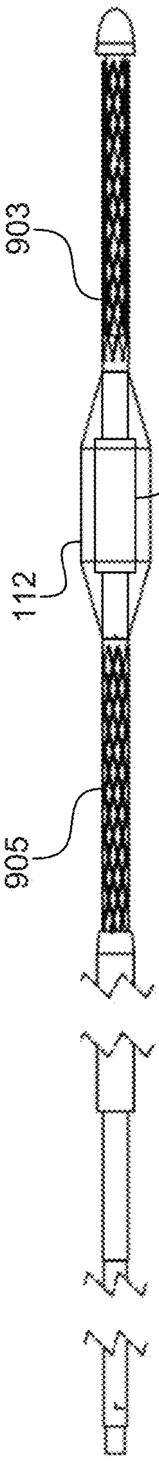
Figure 9C:
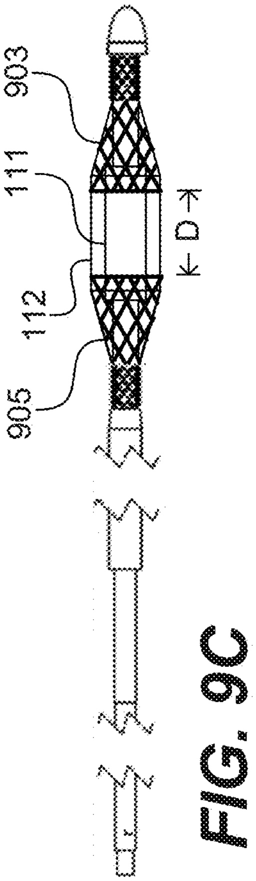
FIG. 9C is a side view of the catheter shaft shown in FIGS. 9A and 9B after the electrodes have been transitioned to their intussuscepted positions, in accordance with certain embodiments.

FIGS. 9A-9C are now used to describe certain embodiments of the catheter 102 introduced above with reference to FIGS. 1, 2A and 2B, wherein elements in FIGS. 9A-9C that are the same as the elements in FIGS. 1, 2A and 2B are labeled the same and need not be described again in detail. In FIGS. 9A-9C only the distal portion 210 of the catheter 102 is shown. More specifically, FIGS. 9A-9C show an implementation of the catheter shaft 214 and the balloon 112 within which is located the transducer 111, wherein the catheter 102 also includes a selectively deployable distal electrode 903 and a selectively deployable proximal electrode 905. More specifically, each of the selectively deployable distal electrode 903 and the selectively deployable proximal electrode 905 is configured to be selectively transitioned between a non-intussuscepted position and an intussuscepted position. The non-intussuscepted position can also be referred to herein as the non-deployed position, and the intussuscepted position can also be referred to herein as the deployed position. FIGS. 9A and 9B are, respectively, perspective and side views of the distal portion 210 of the catheter 102 when the electrodes 903 and 905 are in their non-intussuscepted positions. FIG. 9C is a side view of the distal portion 210 of the catheter 102 after the electrodes 903 and 905 have been transitioned from their non-intussuscepted positions into their intussuscepted positions.

Figure 9I:
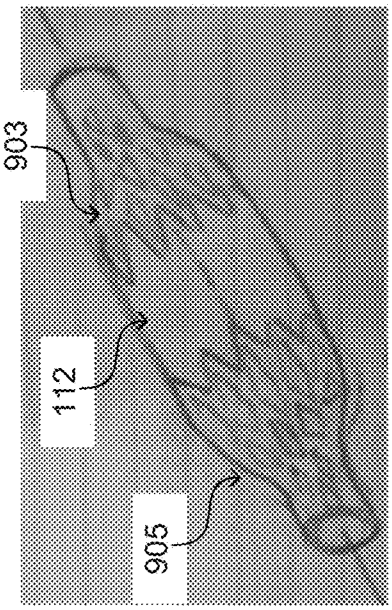
FIG. 9I is a perspective view of the catheter shaft introduced in FIGS. 9A-9C after the distal and proximal electrodes have been transitioned to their intussuscepted positions and resemble cones over distal and proximal portions of the underlying balloon, in accordance with certain embodiments.

In FIGS. 9A and 9B, the transducer 111 is shown as being located within the balloon 112, wherein the balloon is sandwiched between a distal electrode 903 and a proximal electrode 905 in their non-deployed positions. More specifically, in FIGS. 9A and 9B the non-deployed distal electrode 903 is shown as being located distal of the balloon 112 and surrounding and conforming to a tubular distal portion of the underlying catheter shaft 214, and the non-deployed proximal electrode 905 is shown as being located proximal of the balloon 112 and surrounding and conforming to a tubular proximal portion of the underlying catheter shaft 214. As can be appreciated from FIGS. 9A and 9B, when the electrodes 903, 905 are in their non-deployed positions (aka non-intussuscepted positions), the distal electrode 903 does not longitudinally overlap with the balloon 112 and the transducer 111, and the proximal electrode 905 does not longitudinally overlap with the balloon 112 and the transducer 111. By contrast, and as can be appreciated from FIG. 9C, when the electrodes 903, 905 are in their deployed positions (aka intussuscepted positions), the distal electrode 903 longitudinally overlaps with distal portions of the balloon 112 and the transducer 111, and the proximal electrode 905 longitudinally overlaps with proximal portions of the balloon 112 and the transducer 111. As shown in FIGS. 9C and 9I, when the electrodes 903, 905 are in their non-deployed positions they respectively form electrically conductive cones around distal and proximal portions of the underlying balloon 112, and are configured to come into within inner wall portions of the biological lumen within which they are positioned.

Beneficially, when the electrodes 903, 905 are in their non-deployed positions (aka non-intussuscepted positions), the overall profile of the shaft 214 of the catheter 102 is reduced, which is desirably when the shaft 214 is being inserted into a biological lumen because it reduces the probability of damaging the biological lumen and surrounding tissue. Furthermore, when the electrodes 903, 905 are in their non-deployed positions (aka non-intussuscepted positions), the electrodes 903, 905 do not block or otherwise adversely affect the emission pattern of the transducer 111.

In additional to including the selectively deployable (aka selectively intussuscepted) electrodes 903 and 905, the catheter shaft 214 can also include one or more ring electrodes and/or a tip electrode that is/are distal to the selectively deployable distal electrode 903 and/or one or more ring electrodes that is/are proximal the selectively deployable proximal electrode 905. As mentioned above, ring electrodes can also be referred to as marker band electrodes, since they can be used as markers when imaging is used to monitor a position of the catheter 102 within a biological lumen.

In accordance with certain embodiments, after the distal portion 210 of the catheter 102 is inserted into a body lumen (e.g., a renal artery), and positioned at a desired position within the body lumen, the balloon 112 can be at least partially filled with a fluid (e.g., a cooling fluid) so that an outer surface of at least a central portion of the balloon 112 comes into contact with an inner surface of the body lumen. For example, the cooling fluid supply subsystem 428, described above with reference to FIGS. 4 and 5, can be used to at least partially fill the balloon 112 with the cooling fluid. Thereafter (i.e., after the balloon 112 is at least partially filled with the cooling fluid), the electrodes 903 and 905 can be selectively deployed (aka selectively intussuscepted) so that at least a portion of the distal electrode 903 covers a distal portion of the balloon 112 (as shown in FIGS. 9C and 9I), and at least a portion of the proximal electrode 905 covers a proximal portion of the balloon 112 (as also shown in FIGS. 9C and 9I).

While the electrodes 903 and 905 are deployed (aka intussuscepted), the electrodes 903 and 905, respectively, contact first and second portions of an inner surface of the body lumen (e.g., renal artery) that are spaced apart from one another by a distance (D) between the deployed electrodes 903 and 905. At this point, the electrodes 903 and 905 can be used in one or more of various different manners. For example, the deployed electrodes 903 and 905 alone, or in combination with one or more additional electrodes (e.g., ring and/or tip electrodes), can be used to sense native electrical neural activity. More specifically, the electrodes 903 and 905 can be coupled to the inputs of the amplifier 412 in FIG. 4, or the inputs of one of the amplifiers 712*a* or 712*b* in FIG. 7, to thereby sense native electrical neural activity.

Alternatively, or additionally, the electrodes 903 and 905 can be used (alone, or together with other electrodes, such as one or more ring electrodes, and/or a tip electrode) to selectively deliver the stimulation pulse(s) and sense an evoked neural response to the stimulation pulse(s). For example, during a first period of time, the electrodes 903 and 905 can be coupled to the stimulator 406 in FIG. 4 (as anode and cathode electrodes) and used to deliver stimulation, and during a second period of time the electrodes 903 and 905 can be coupled to the amplifier 412 in FIG. 4 (as sense electrodes) to thereby sense an evoked neural response to the stimulation. For another example, during a first period of time, the electrodes 903 and 905 can be coupled to the stimulator 706 in FIG. 7 (as anode and cathode electrodes) and used to deliver stimulation, and during a second period of time the electrodes 903 and 905 can be coupled to the amplifier 712*a* or 712*b* in FIG. 7 (as sense electrodes) to thereby sense an evoked neural response to the stimulation. It is also possible that just one of the electrodes 903 and 905 is used for delivering stimulation (together with one or more ring and/or tip electrodes), and the other one of the electrodes 903 and 905 (together with one or more ring and/or tip electrodes) is used to sense the evoked neural response to the stimulation. Other variations are also possible and within the scope of the embodiments described herein. A description of how the electrodes 903 and 905 can be transitioned from their non-intussuscepted (aka non-deployed) state to their intussuscepted (aka deployed) state is provided below.

In certain embodiments, the catheter shaft 214 includes a plurality of nested and concentric tubes, wherein one or more of the tubes can be selectively maneuvered longitudinally using actuators (e.g., 221 in FIG. 2A) that are located on a proximal portion (e.g., on a handle) of the catheter 102. FIG. 10A-10E illustrate examples of the various nested and concentric tubes of the catheter shaft 214. More specifically, referring to FIGS. 10A-10E, the catheter shaft 214 is shown as including four concentric and nested tubes 1031, 1032, 1033, and 1034, which can be referred to respectively as a first tube 1031, a second tube 1032, a third tube 1033, and a fourth tube 1034. The catheter shaft 214, which can also be referred to more succinctly as the shaft 214, also includes the aforementioned electrodes 903 and 905, the balloon 112 and the transducer 111. As noted above, and as will be described in additional detail below, each of the electrodes 903 and 905 can be selectively transitioned between its non-deployed (aka non-intussuscepted) position and its deployed (aka intussuscepted) position using one or more actuators (e.g., 221 in FIG. 2A) on the handle 220 of the catheter 102. As will be described in further detail below, in accordance with certain embodiments the shaft 214 can additionally include one or more non-deployable ring electrodes and/or a tip electrode. For example, the shaft 214 can include a proximal ring electrode located near the distal end of the first tube 1031 and/or a distal tip or ring electrode located at or near the distal end of the fourth tube 1034. As noted above, the aforementioned ring electrodes can also be referred to as marker band electrodes, since they can be used to as markers when imaging is used to monitor a position of the catheter within a biological lumen.

In accordance with certain embodiments of the present technology, each of the electrodes 903, 905 is made of a unitary nitinol tube that is laser cut to include apertures or openings having a predetermined pattern. The electrodes 903, 905 can alternatively be made of a mesh of braded wires. The use of alternative types of metals, alloys or other electrically conductive materials for the electrodes are also possible and within the scope of the embodiments described herein.

Figures 10A, 10B, 10C, 10D, 10E:
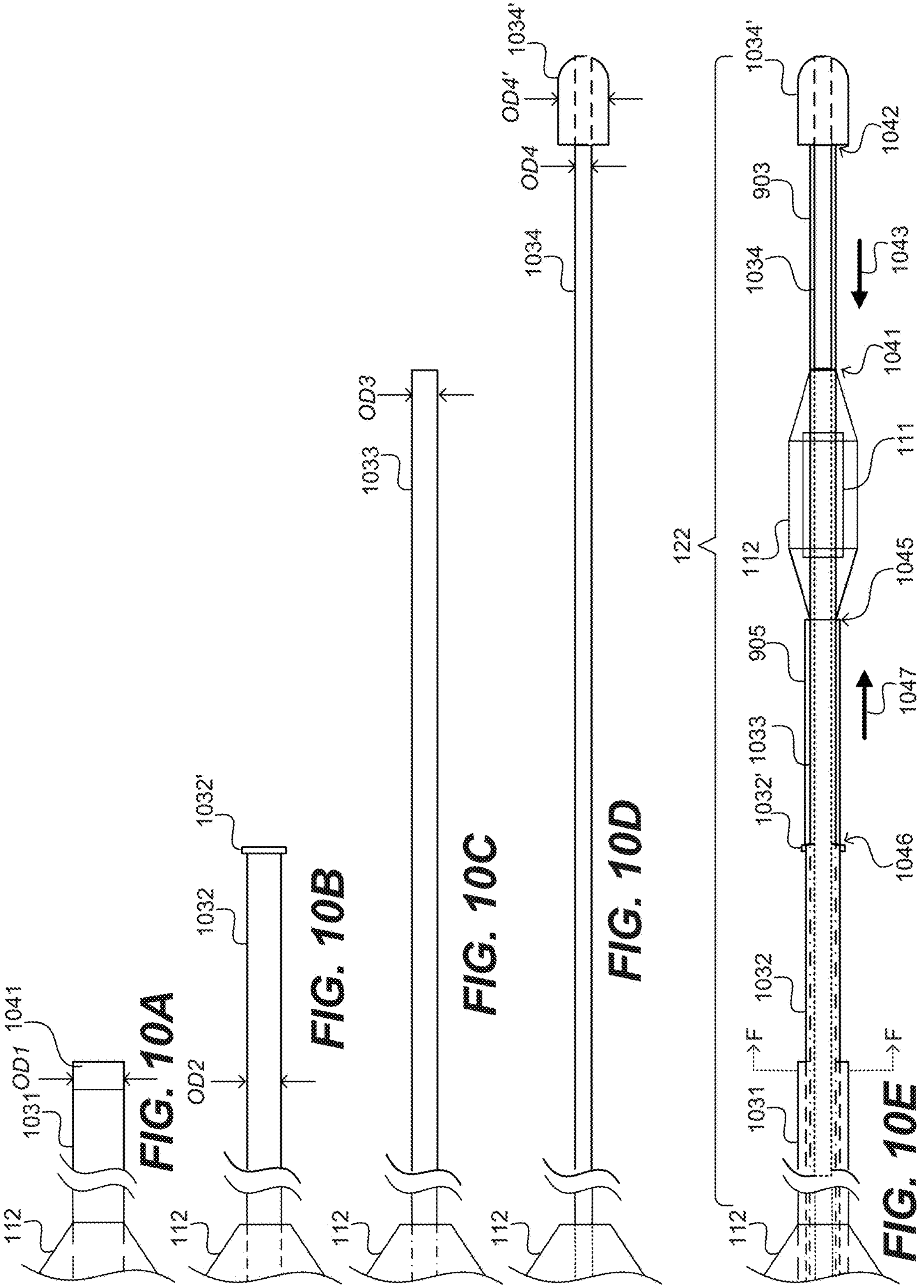
FIG. 10A-10E illustrates how a catheter shaft can include multiple nested concentric tubes, in accordance with certain embodiments.
Figure 10F:
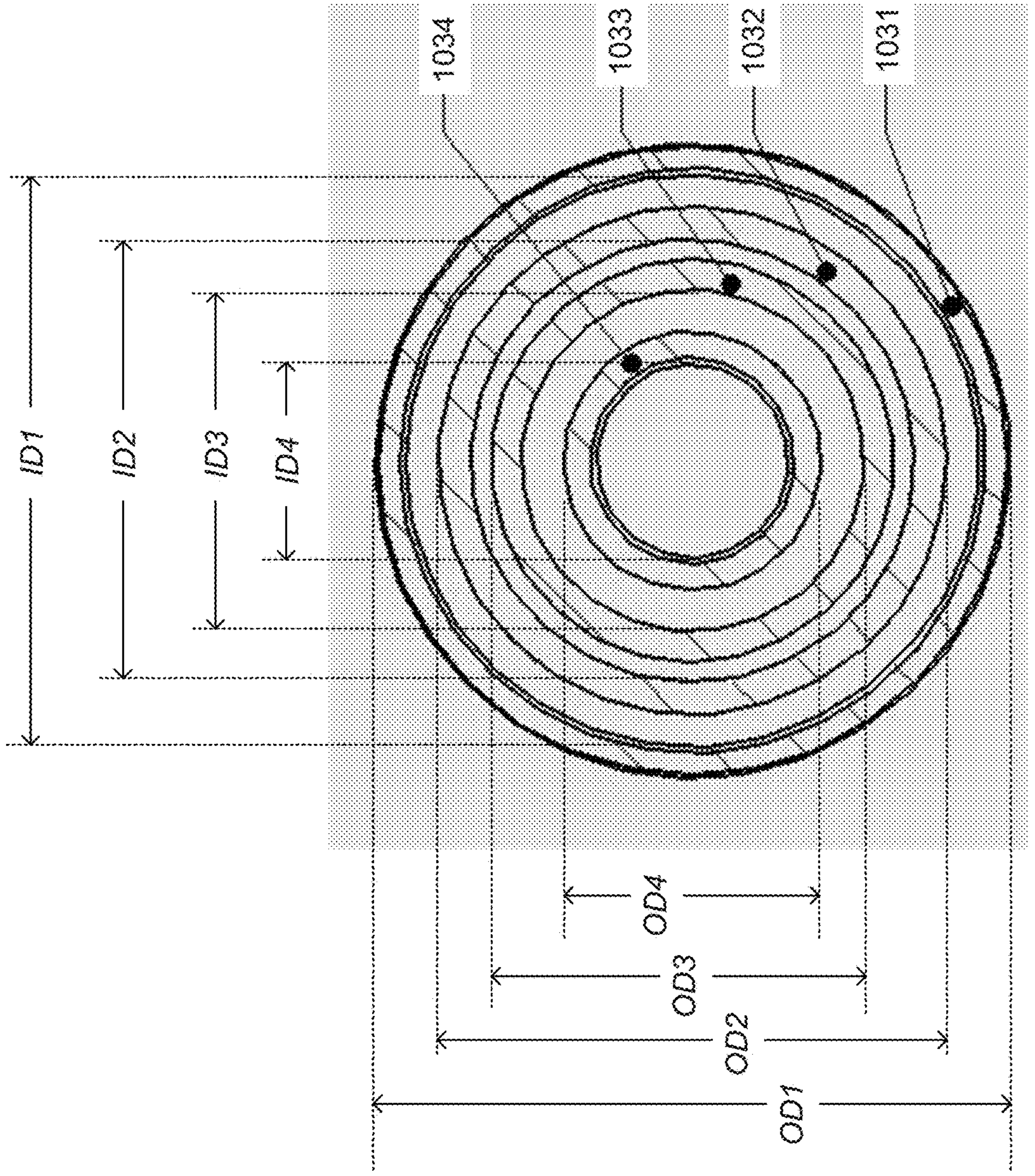
FIG. 10F is a cross section of the tubes shown in FIG. 10E along the dashed line F-F, in accordance with certain embodiments.

Additional details of the concentric tubes 1031, 1032, 1033, and 1034 of the catheter shaft 214, according to certain embodiments of the present technology, will now be described with reference to FIGS. 10A-10F, wherein FIG. 10F is a cross section of the shaft 214 along the dashed line F-F shown in FIG. 10E. As will be described in additional detail below, and as can be appreciated from FIGS. 10A-10F, proximal portions of the concentric tubes 1031, 1032, 1033, and 1034 extend into the handle 220 (aka proximal portion 220) of the catheter 102. The wall thickness of each of the tubes 1031, 1032, 1033, 1034, in accordance with certain embodiments, is 0.006 inches. The use of thicker or thinner walls is also possible and within the scope of the embodiments described herein. Referring to FIGS. 10A and 10F, the first tube 1031 is shown as extending from the handle 220 and having an outer diameter OD1, and an inner diameter ID1. Referring to FIGS. 10B and 10F, the second tube 1032 is shown as extending from the handle 220 and having an outer diameter OD2 (which is less than the inner diameter ID1 of the first tube 1031), and having an inner diameter ID2.

FIG. 10E shows that a portion of a length of the fourth tube 1034 extends through the first, second, and third tubes 1031, 1032, and 1033; a portion of a length of the third tube 1033 extends through the first and second tubes 131 and 132; and a portion of a length of the second tube 1032 extends through the first tube 1031. It can also be appreciated from FIG. 10E that a portion of each of the second, third, and fourth tubes 1031, 1032, and 1033 extends through a hollow lumen of the proximal electrode 905, and a portion of the fourth tube 1034 extends through a hollow lumen of the distal electrode 903.

In accordance with an embodiment, the outer diameter OD1 of the first tube 1031 is 0.078 inches, the outer diameter OD2 of the second tube 1032 is 0.063 inches, the outer diameter OD3 of the third tube 1033 is 0.050 inches, and the outer diameter OD4 of the fourth tube 1034 is 0.032 inches. Assuming the wall thickness of each of the tubes 1031, 1032, 1033, and 1034 is 0.006 inches, then the inner diameter ID1 of the first tube 1031 is 0.064 inches (i.e., 0.078−(2×0.006)=0.066), the inner diameter ID2 of the second tube 1032 is 0.51 inches, the inner diameter ID3 of the third tube 1033 is 0.038 inches, and the inner diameter ID4 of the fourth tube 1034 is 0.020 inches. The use of alternative outer and inner diameters, and the use of other wall thicknesses, are also within the scope of the embodiments of the present technology described herein, so long as the outer diameter OD4 of the fourth tube 1034 is less than the inner diameter ID3 of the third tube 1033, the outer diameter ID3 of the third tube 1033 is less than the inner diameter ID2 of the second tube 1032, and the outer diameter ID2 of the second tube 1032 is less than the inner diameter ID1 of the first tube 1031.

As can be appreciated from FIGS. 10A-10E, the longitudinal length of the fourth tube 1034 is greater than the longitudinal length of the third tube 1033, the longitudinal length of the third tube 1033 is greater than the longitudinal length of the second tube 1032, and the longitudinal length of the second tube 1032 is greater than the longitudinal length of the first tube 1031.

As can be appreciated from FIG. 10E, the transducer 111 and the balloon 112 are shown as being located on a distal portion of the third tube 1033. The proximal electrode 905 is shown as resting over a portion of the third tube 1033 between the proximal end of the balloon 112 and a flange 1032' that is at a distal end of the second tube 1032. The distal electrode 903 is shown as resting over a portion of the fourth tube 1034 between the distal end of the balloon 112 and a flange 1034' that it at a distal end of the fourth tube 1034.

In accordance with an embodiment, a proximal end of the distal electrode 903 is physically connected to a distal end of the third tube 1033 (at the region labeled 1041), and a distal end of the distal electrode 903 is physically connected to a distal portion of the fourth tube (at the region labeled 1042) or abuts against a proximal end of the flange 1034' of the fourth tube 1034. Additionally, a distal end of the proximal electrode 905 is physically connected to in intermediate portion of the third tube 1033 (at the region labeled 1045), and a proximal end of the proximal electrode 1033 is physically connected to a distal portion of the second tube (at the region labeled 1046) or abuts against a distal end of the flange 1032' of the second tube 1032.

Figure 9F:
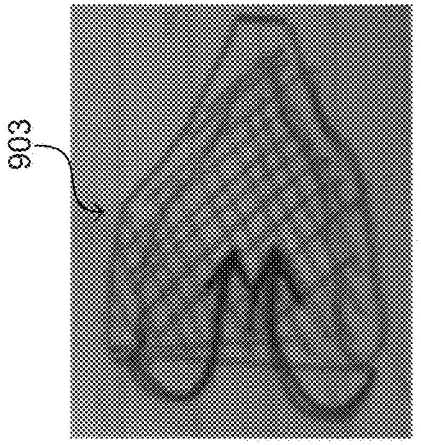
FIGS. 9E and 9F illustrates how the distal electrode initially bulges outward and then folds in on itself when transitioned from the non-intussuscepted position to the intussuscepted position, in accordance with certain embodiments.
Figure 9H:
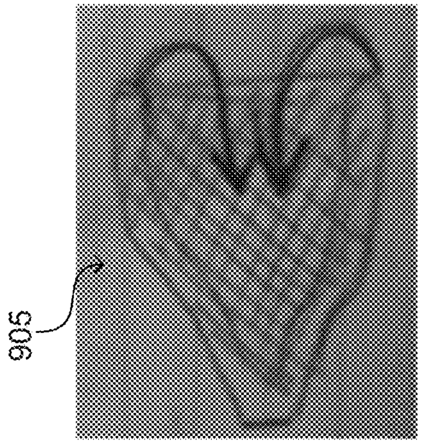
FIGS. 9G and 9H illustrates how the proximal electrode initially bulges outward and then folds in on itself when transitioned from the non-intussuscepted position to the intussuscepted position, in accordance with certain embodiments.
Figure 9E:
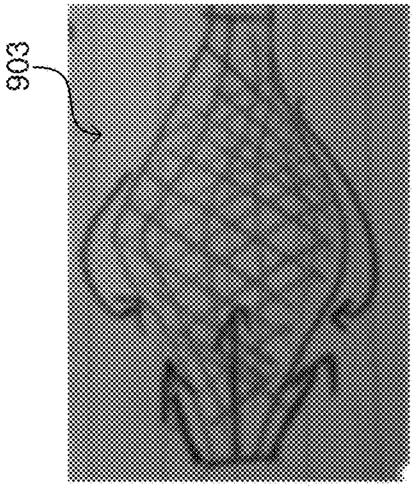
Figure 9G:
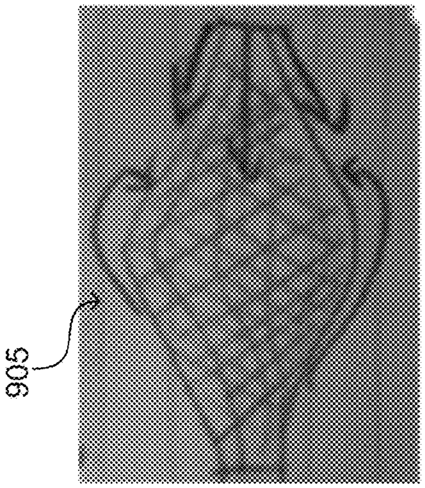

In order to transition the distal electrode 903 from its non-intussuscepted (aka non-deployed) position to its intussuscepted (aka deployed) position, the fourth tube 1034 is moved in the proximal direction indicated by the arrow 1043. This has the effect of causing the distal electrode 903 to initially bulge outward (as shown in FIG. 9E) and then fold-over itself (as shown in FIG. 9F) and over a distal portion of the balloon 112 (as shown in FIG. 9I). In order to transition the proximal electrode 905 from its non-intussuscepted (aka non-deployed) position to its intussuscepted (aka deployed) position, the second tube 1032 is moved in the distal direction indicated by the arrow 1047. This has the effect of causing the proximal electrode 905 to initially bulge outward (as shown in FIG. 9G) and then fold-over itself (as shown in FIG. 9H) and over a proximal portion of the balloon 112 (as shown in FIG. 9I). Other techniques for transitioning the electrodes between their non-intussuscepted (aka non-deployed) positions and their intussuscepted (aka deployed) positions are also possible and within the scope of the embodiments described herein. For example, it is also possible that one or more pull wires and/or push wires can be included and used.

Figures 11A, 11B:
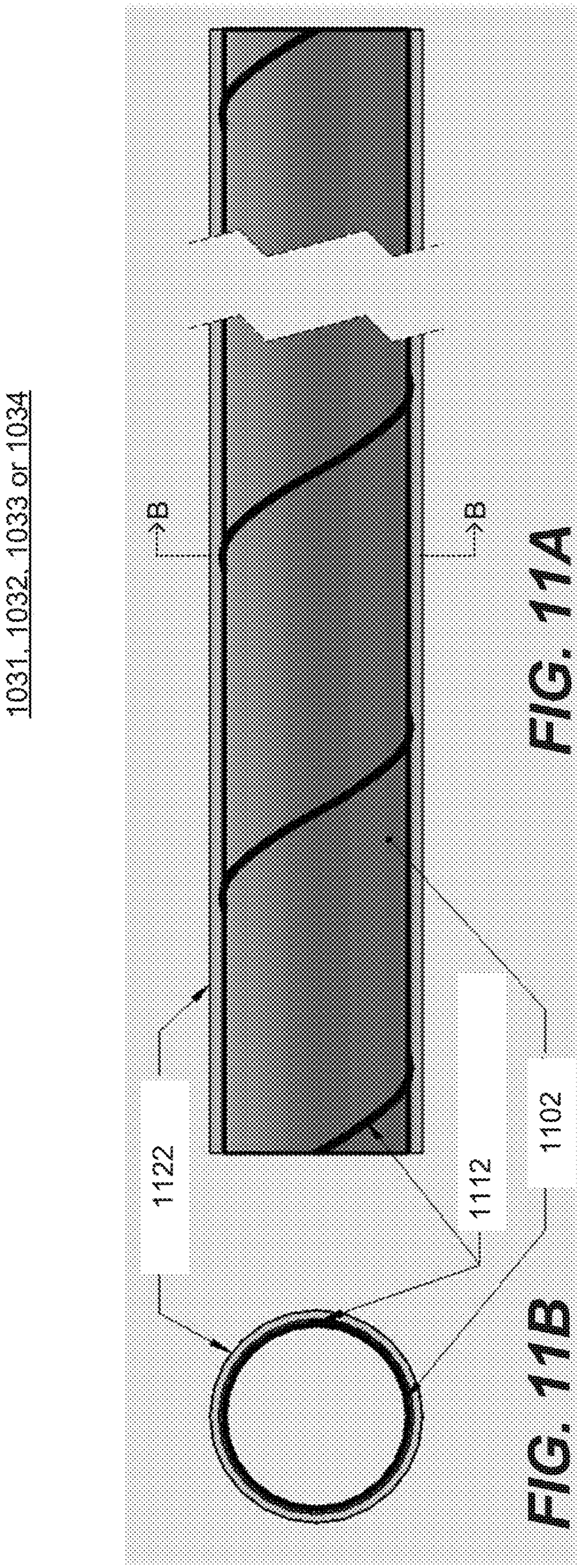
FIGS. 11A and 11B are used to describe additional details of one or more of the tubes introduced in FIGS. 10A-10F, according to certain embodiments of the present technology.

FIGS. 11A and 11B will now be used to described additional details of each of the tubes 1031, 1032, 1033, and 1034, according to certain embodiments of the present technology, wherein FIG. 11A shows an example portion of a length of such tubes, and FIG. 11B shows a cross section along the line B-B in FIG. 11A. Referring to FIGS. 11A and 11B, each of the tubes is shown as including a tubular liner 1102 that is made of a non-electrically conductive material, such as, but not limited to, Polytetrafluoroethylene (PTFE), which is a synthetic fluoropolymer of tetrafluoroethylene. The liner 1102, which is cylindrical and hollow, can also be referred to as the inner liner 1102. Coiled around the tubular inner liner 1102 is a coiled wire 1112 that is made of an electrically conductive material, such as, but not limited to, stainless steel, or a platinum-iridium alloy. Surrounding the coiled wire 1112 is an outer jacket 1122 that is made of a non-electrically conductive material, such as, but not limited to, Polyether block amide (PEBA), which is often marketed under the trademark PEBAX™ (which is a registered trademark of Arkema S.A, headquartered in Colombes, France). Accordingly, it can be appreciated that the coiled wire 1112 is sandwiched between the tubular inner line 1102 and the outer jacket 1122. In accordance with certain embodiments of the present technology, the coiled wire 1112 of each tube provides structural support for the tube, and in some cases also provides an electrically conductive path between an electrode (e.g., 903 or 905) and an electrical control unit (ECU), examples of which are described below with reference to FIGS. 4 and 7. The structural support provided by the coiled wire 1112 provides the tube (that includes the coiled wire 1112) with kink-resistance and crush-resistance. The electrically conductive path provided by the coiled wire 1112 enables an electrical connection to an electrode (e.g., 903 or 905, or a ring or tip electrode) of the catheter 102 without requiring that a wire be positioned within the hollow lumen(s) of one or more of the tubes 1031, 1032, 1033, 1034, or more generally, without requiring that one or more wires extend through one or more lumens within the shaft 214.

One or more of the tubes 1031, 1032, 1033, and 1034 can each include more than one coiled wire (e.g., 1112) so that one such tube can provide two or more electrically conductive paths. For an example, the tube 1033 can include first and second coiled wires (not specifically shown) that are spaced apart from one another or are otherwise electrically insulated from one another.

Referring briefly back to FIGS. 10A-10D, if the catheter 102 included a ring electrode 1041 near the distal end of the first tube 1031, the coiled wire 1112 of the first tube 1031 can be used to provide an electrically conductive path between the ring electrode 1041 and a wire within the handle, which wire is connected to the connection cable 140 (in FIG. 1), to thereby provide an electrically conductive path between the ring electrode 1041 and an ECU (e.g., 402 in FIG. 4, or 702 in FIG. 7). Additionally, or alternatively, a ring or tip electrode can be located near the distal end of the fourth tube 1034, e.g., on the flange 1034' of the fourth tube 1034, in which case the coiled wire 1112 of the fourth tube 1034 can be used to provide an electrically conductive path between the ring or tip electrode (on the flange 1034') and a wire within the handle, which wire is connected to the connection cable 140 (in FIG. 1), to thereby provide an electrically conductive path between the ring or tip electrode (on the flange 1034') and the ECU.

Spiral Electrodes

Figure 12:
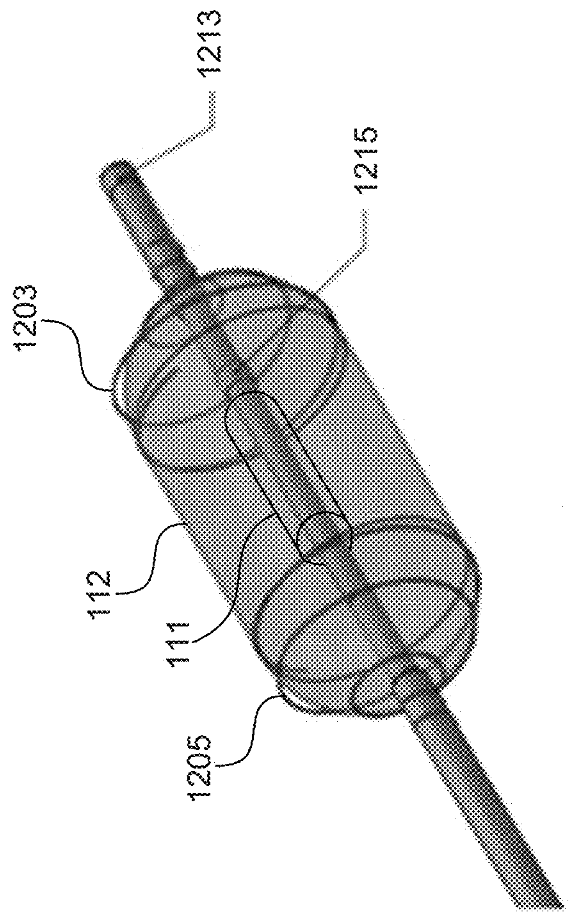
FIG. 12 is a perspective view of a catheter shaft having spiral distal and proximal electrodes that respectively surround distal and proximal portions of an underlying balloon, in accordance with certain embodiments.

FIG. 12 illustrates an embodiment where a distal portion of the balloon 112 is partially surrounded by a distal electrode 1203 and a proximal portion of the balloon 112 is partially surrounded by a proximal electrode 1205. The transducer 111 is shown as being within balloon 112. In the embodiment of FIG. 12, each of the electrodes 1203, 1205 is a spiral electrode, and thus, they can be referred to more specifically as a spiral distal electrode 1203 and a spiral proximal electrode 1205. In accordance with certain embodiments, the balloon 112 and the electrodes 1203 and 1205 are located on a distal portion of the catheter shaft 214 of the catheter 102 introduced above in FIGS. 1, 2A and 2B. The distal spiral electrode 1203 is shown encircling a distal portion of the balloon 112, and the proximal spiral electrode 1205 is shown as encircling a proximal portion of the balloon 112. The spiral electrodes 1203 and 1205 can also be referred to as coiled electrodes.

In certain embodiments, each of the spiral distal and proximal electrodes 1203, 1205 is made of an electrically conductive material that has shape memory that causes the electrodes to generally conform to a tubular portion of the underlying catheter shaft 214 when the balloon 112 is deflated (aka uninflated). In certain embodiments, the spiral distal and proximal electrodes 1203, 1205 are made of Nitinol, which is a metal alloy of nickel and titanium, that is electrically conductive, has shape memory, and has superelasticity. It is also within the scope of the embodiments of the present technology described herein to manufacture the electrodes 1203, 1205 of another known or future developed alloy or material, besides Nitinol, wherein the material is electrically conductive, has shape memory, and preferably has superelasticity.

In the embodiment of FIG. 12, the spiral electrodes 1203 and 1205 will be in their non-deployed tightly wound positions when the balloon 112 is non-inflated, and the spiral electrodes 1203 and 1205 transition to their deployed partially unwound positions in response to the balloon 112 being at least partially inflated by being at least partially filled with a fluid (e.g., a cooling fluid) that is provided to an interior of the balloon 112 through a lumen (e.g., 327) of the catheter 102. More specifically, as the balloon 112 is filled and thereby expands, windings of the spiral electrodes 1203 and 1205 begin to partially unwind and expand in diameter as the diameter of the underlying balloon 112 expands. The shape memory of the distal and proximal spiral electrodes 1203 and 1205 causes them to rewind in response to the balloon 112 being deflated, after the balloon 112 had been at least partially inflated.

Beneficially, when the electrodes 1203, 1205 are in their tightly wound non-deployed positions, the overall profile of the shaft 214 of the catheter 102 is reduced, which is desirably when the shaft 214 is being inserted into a biological lumen because it reduces the probability of damaging the biological lumen and surrounding tissue.

In additional to including the spiral distal and proximal electrodes 1203 and 1205, the catheter shaft 214 can also include one or more ring electrodes and/or a tip electrode that is/are distal to the spiral distal electrode 1203 and/or one or more ring electrodes that is/are proximal the spiral proximal electrode 1205. Such ring electrodes can also be referred to as marker band electrodes, since they can be used as markers when imaging is used to monitor a position of the catheter 102 within a biological lumen. For example, a distal ring or tip electrode 1213 is shown in FIG. 12. Additionally, a ring (aka marker) electrode 1215 is shown within the balloon 112. Additional ring electrodes can be located distal to the balloon 112 and/or proximal to the balloon 112.

In accordance with certain embodiments, after the distal portion 210 of the catheter 102 is inserted into a body lumen (e.g., a renal artery), and positioned at a desired position within the body lumen, the balloon 112 can be at least partially filled with a fluid (e.g., a cooling fluid) so that an outer surface of at least a central portion of the balloon 112 comes into contact with an inner surface of the body lumen. For example, the cooling fluid supply subsystem 428, described above with reference to FIGS. 4 and 5, can be used to at least partially fill the balloon 112 with the cooling fluid. In response to the balloon 112 being at least partially filled with the cooling fluid, the spiral electrodes 1203 and 1205 unwind and expand because the spiral distal electrode 1203 conforms to an underlying expanded distal portion of the at least partially filled balloon 112 and the spiral proximal electrodes 1205 conforms to an underling expanded proximal portion of the at least partially filled balloon 112.

While the spiral electrodes 1203 and 1205 are at least partially unwound and expanded, the electrodes 1203 and 1205, respectively, contact first and second portions of an inner surface of the body lumen (e.g., renal artery) that are spaced apart from one another by a distance between the electrodes 1203 and 1205. At this point, the electrodes 1203 and 1205 can be used in one or more of various different manners. For example, the spiral electrodes 1203 and 1205 alone, or in combination with one or more additional electrodes (e.g., ring and/or tip electrodes), can be used to sense native electrical neural activity. More specifically, the electrodes 1203 and 1205 can be coupled to the inputs of the amplifier 412 in FIG. 4, or the inputs of one of the amplifiers **712*a* or 712*b* in FIG. 7**, to thereby sense native electrical neural activity.

Alternatively, or additionally, the electrodes 1203 and 1205 can be used (alone, or together with other electrodes, such as one or more ring electrodes, and/or a tip electrode) to selectively deliver the stimulation pulse(s) and sense an evoked neural response to the stimulation pulse(s). For example, during a first period of time, the electrodes 1203 and 1205 can be coupled to the stimulator 406 in FIG. 4 (as anode and cathode electrodes) and used to deliver stimulation, and during a second period of time the electrodes 1203 and 1205 can be coupled to the amplifier 412 in FIG. 4 (as sense electrodes) to thereby sense an evoked neural response to the stimulation. For another example, during a first period of time, the electrodes 1203 and 1205 can be coupled to the stimulator 706 in FIG. 7 (as anode and cathode electrodes) and used to deliver stimulation, and during a second period of time the electrodes 1203 and 1205 can be coupled to the amplifier 712*a* or 712*b* in FIG. 7 (as sense electrodes) to thereby sense an evoked neural response to the stimulation. It is also possible that just one of the electrodes 1203 and 1205 is used for delivering stimulation (together with one or more ring and/or tip electrodes), and the other one of the electrodes 1203 and 1205 (together with one or more ring and/or tip electrodes) is used to sense the evoked neural response to the stimulation. Other variations are also possible and within the scope of the embodiments described herein.

Figure 13:
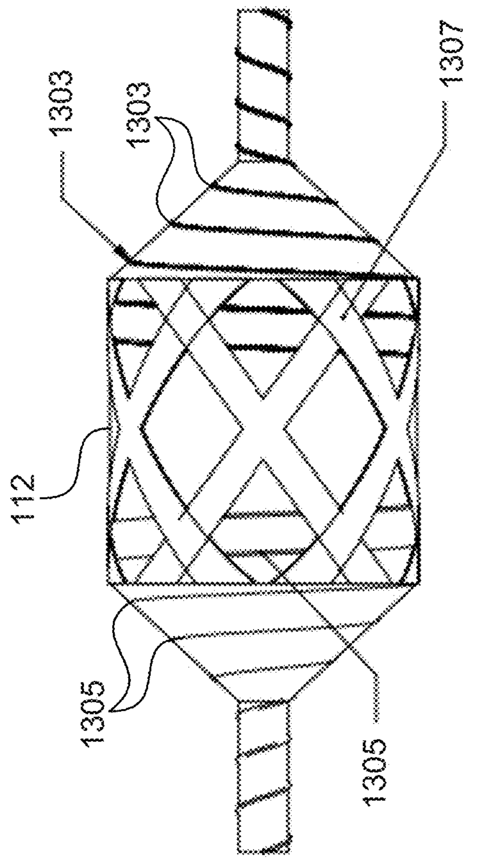
FIG. 13 is a side view of a catheter shaft having spiral distal and proximal electrodes that respectively surround distal and proximal portions of an underlying balloon, wherein the electrodes are held in place by a net, in accordance with certain embodiments.

In the embodiment described above with reference to FIG. 12, the shape memory of the distal and proximal spiral electrodes 1203 and 1205 keeps the electrodes in place over the distal and proximal portions of the balloon 112. In the embodiment of FIG. 13, a net 1307 covers at least a portion of the balloon 112 and at least a portion of distal and proximal spiral electrodes 1303 and 1305 to hold the electrodes in a desired position relative to the underlying balloon 112. In certain embodiments, the material from which the net 1307 is made is the same non-electrically conductive material from which the underlying balloon 112 is made, so that the expansion and retraction properties of net 1307 is the same as the expansion and retraction properties of the underling balloon. For example, the balloon 112 and the net 1307 can be made from nylon, a polyimide film, a thermoplastic elastomer (such as those marked under the trademark PEBAX™), a medical-grade thermoplastic polyurethane elastomers (such as those marketed under the trademark PELLETHANE™), pellethane, isothane, or other suitable polymers or any combination thereof, but is not limited thereto. It is also possible that the net 1307 is made from a different non-electrically conductive material than the underlying balloon 112. The electrodes 1303 and 1305 can be used in the same various different manners that the electrodes 1203 and 1205 described above can be used, and thus, such uses need not be described again. The electrically conductive material of which the electrodes 1303 and 1305 are made can have shape memory, as was also the case with the electrodes 1203 and 1205. Alternatively, the electrodes 1303 and 1305 can be made of an electrically conductive material that lacks shape memory. While not specifically shown in FIG. 13, the transducer 111 can be located within the balloon 112, as was described above with reference to other embodiments.

Figure 14A:
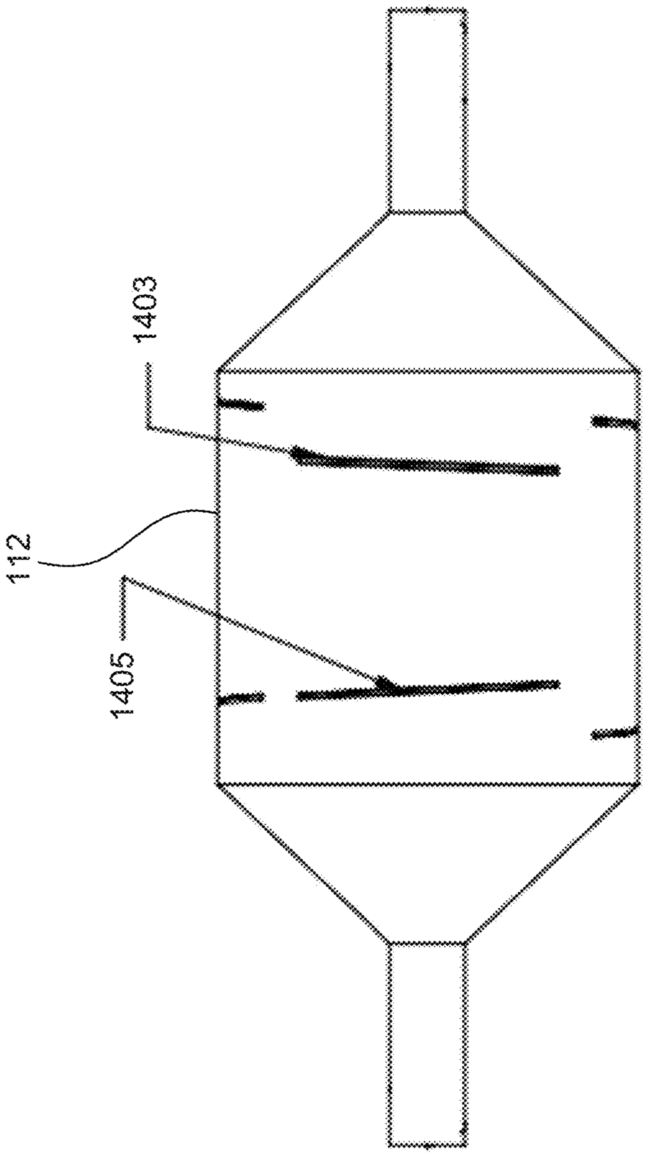
FIGS. 14A and 14B are side views of a catheter shaft having distal and proximal electrodes and a balloon, wherein the balloon is made from an innermost layer and an outermost layer, one or more portions of each of the distal and proximal electrodes are provided by respective wires sandwiched between the layers, and one or more further portions of each of the distal and proximal electrodes are exposed portions of the wires where the outermost layer of the balloon has been removed, in accordance with certain embodiments.
Figure 14B:
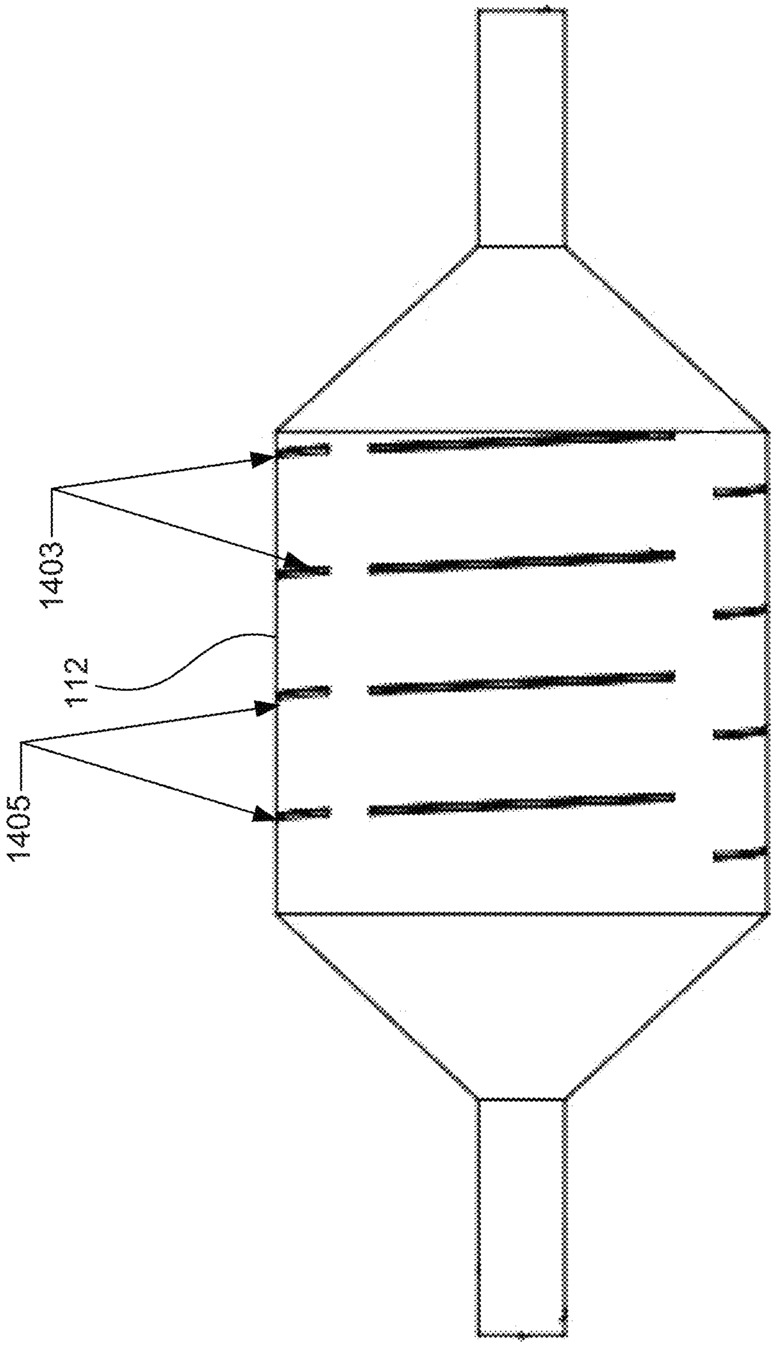
Figure 14C:
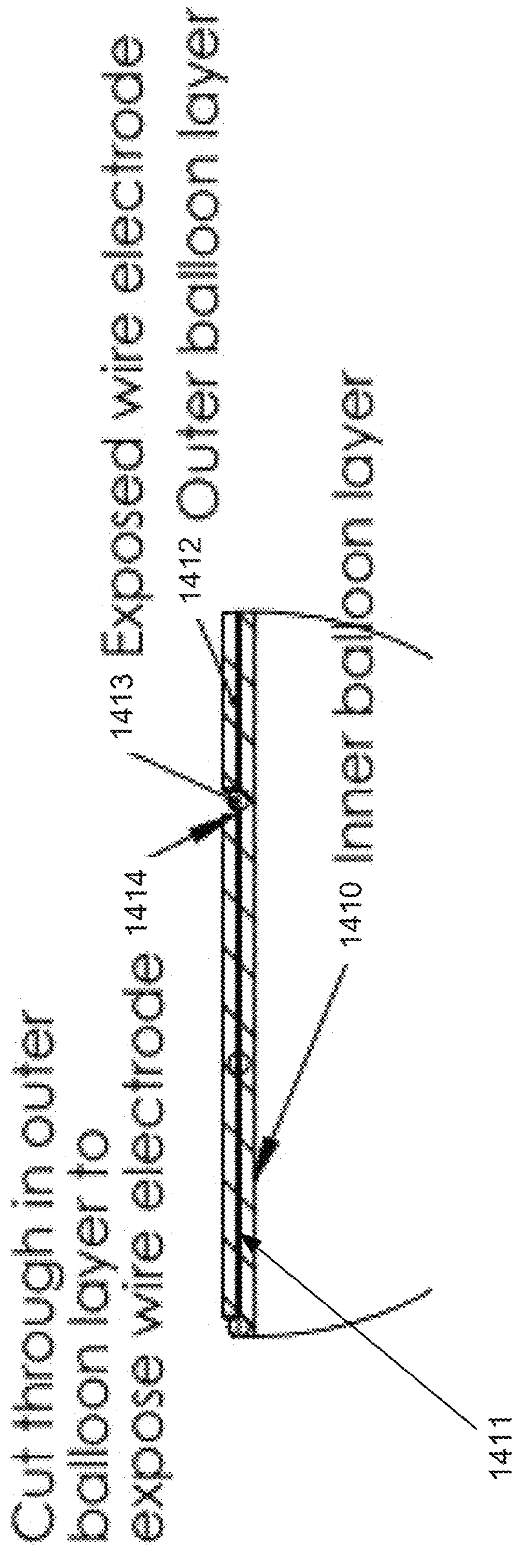
FIG. 14C is a cross-sectional view showing the aforementioned innermost and outermost layers of the balloon, and how the wire that provides one of the electrodes can be exposed by a cut-through in the outermost layer.

In the embodiments of FIGS. 14A-14C, distal and proximal spiral (aka coiled) or braided wire electrodes 1403 and 1404 are laminated between two balloon layers, which are fused together. Following fusing of the two balloon layers, the outermost balloon layer is selectively removed from the wire in order to create an exposed electrode, sandwiched between layers of the balloon 112. Each of the balloon layers can be made from nylon, a polyimide film, a thermoplastic elastomer (such as those marked under the trademark PEBAX™), a medical-grade thermoplastic polyurethane elastomers (such as those marketed under the trademark PELLETHANE™), pellethane, isothane, or other suitable polymers or any combination thereof, but are not limited thereto. The innermost and outermost balloon layers can be made of the same material as one another, or from different materials than one another. The electrodes 1403 and 1405 can be used in the same various different manners that the electrodes 1203 and 1205 described above can be used, and thus, such uses need not be described again. The electrically conductive material of which the electrodes 1403 and 1405 are made can have shape memory, as was also the case with the electrodes 1203 and 1205. Alternatively, the electrodes 1403 and 1405 can be made of an electrically conductive material that lacks shape memory. While not specifically shown in FIGS. 14A and 14B, the transducer 111 can be located within the balloon 112, as was described above with reference to other embodiments. In FIG. 14A, each of the electrodes 1403 and 1404 is shown as encircling the underlying balloon 112 once. Alternatively, as shown in FIG. 14B, each of the electrodes 1403 and 1404 can encircle the underlying balloon 112 multiple times. The cross-sectional view in FIG. 14C is used to further explain the embodiments of FIGS. 14A and 14B. Referring to FIG. 14C, shown therein is a wire 1411 sandwiched between an inner balloon layer 1410 and an outer balloon layer 1412. The wire 1411 is shown as being exposed at region 1413 where there is a cut-through 1414 in the outer balloon layer 1412. Multiple cut-throughs in the outer balloon layer 1412 can be used to expose the wire 1411 at multiple locations about the circumference of the balloon. The wire 1411 in FIG. 14C can correspond to one of the electrodes 1403 and 1404 in FIGS. 14A and 14B, and a separate similar selectively exposed wire can correspond to the other one of the electrodes.

Coated Electrodes

Figure 15:
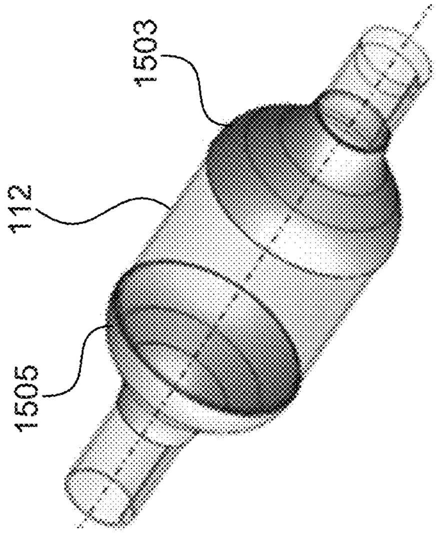
FIGS. 15 and 16 are perspective views of balloons of catheters, wherein the balloons includes distal and proximal coated electrodes on an outer surface of the balloon, in accordance with certain embodiments of the present technology.

FIG. 15 is a perspective view of the balloon 112, according to another embodiments of the present technology. To reduce clutter, the transducer 111 is not shown within the balloon 112. However, it should be understood that in certain embodiments the transducer 111 is indeed included within the balloon 112, in which case cooling fluid can be circulated through an interior of the balloon 112 to thereby cool the transducer 111. Referring to FIG. 15, the balloon 112 is shown as including a distal electrode 1503 located on and encircles a distal portion of the balloon 112, and a proximal electrode 1505 located on and encircles a proximal portion of the balloon 112. Each of the electrodes 1503, 1505 can be created by vapor deposition, printing, painting via masking, or equivalent material deposition process of an electrically conductive metal, such as platinum (Pt), gold (Au), or silver (Ag), but not limited thereto, or an electrically conductive alloy. More generally, each of the electrodes 1503, 1505 is produced by coating a respective portion of the balloon with an electrically conductive metal or alloy coating, and thus, the electrodes 1503, 1505 can also be referred to as electrically conductive coating or coated electrodes. As shown in FIG. 15, there is gap or distance between the electrically conductive coated electrodes 1503, 1505 so that they are electrically isolated from one another.

Each of the electrically conductive coated electrodes 1503, 1505 is electrically coupled to a wire, or insulated strand in a braided jacket, or the like, through the catheter body. Each electrode is electrically connected, and its wire is appropriately insulated or isolated within the catheter body. The electrodes 1503 and 1505 can be used in the same various different manners that the electrodes 1203 and 1205 described above can be used, and thus, such uses need not be described again.

In FIG. 15 only two electrically conductive coating electrodes 1503, 1505 are shown as being located on the balloon 112. However, it should be understood that more than two electrically conductive coating electrodes 1503, 1505 can be located on the balloon 112. In certain embodiments, each of the electrodes 1503, 1505 can provide complete coverage of a cone or balloon body up to a point of physical and electrical isolation from the other electrode. In other embodiments, a pattern of the electrode can be lattice or network to optimize transmission such as fractal antenna.

Figure 16:
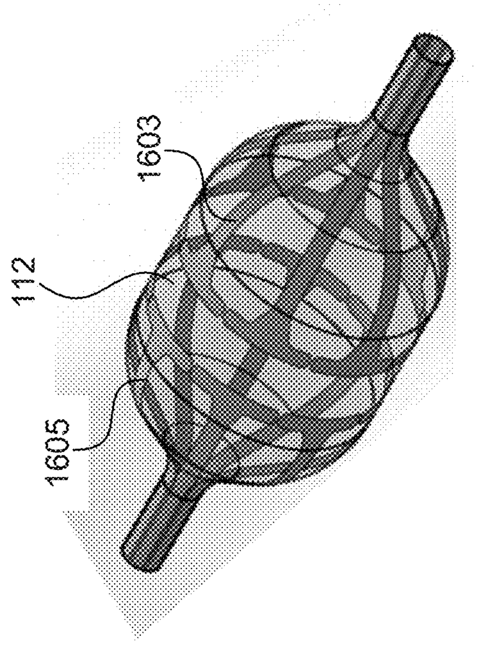

For example, in FIG. 16, each of the electrodes 1603 and 1605 includes a pattern painted onto an outer surface of the underlying balloon 112.

In various embodiments described above, a body of the balloon 112, which is configured to be at least partially filled with a cooling fluid, is made of a non-electrically conductive material, such as nylon, a polyimide film, a thermoplastic elastomer, a medical-grade thermoplastic polyurethane elastomer, pellethane, isothane, or other suitable polymers or any combination thereof, as noted above. While the distal portion 210 of the catheter 102 is positioned within a portion of a biological lumen and the electrically insulated balloon 112 is inflated such that an outer circumference of the electrically insulated balloon contacts an inner circumference of the biological lumen, the balloon 112 restricts blood from flowing from a first location adjacent the distal electrode (e.g., 903, 1203, 1303, 1403 or 1503) to a second location adjacent the proximal electrode (e.g., 905, 1205, 1305, 1405 or 1505), and/or vice versa. This creates an insulating layer between the distal electrode (e.g., 903, 1203, 1303, 1403 or 1503) and the proximal electrode (e.g., 905, 1205, 1305, 1405 or 1505). While the electrically insulated balloon 112 is inflated and restricts blood from flowing past the balloon from the first location adjacent the distal electrode to the second location adjacent the proximal electrode (and thereby creates an insulating layer between the distal and proximal electrodes), stimulation energy can be delivered using the distal electrode and an evoked neural response to the stimulation energy can be sensed using the proximal electrode. Alternatively, or additionally, while the electrically insulated balloon 112 is inflated and restricts blood from flowing past the balloon (and thereby creates an insulating layer between the distal and proximal electrodes), stimulation energy can be delivered using the proximal electrode and an evoked neural response to the stimulation energy can be sensed using the distal electrode. Beneficially, by creating an insulating layer between the distal and proximal electrodes, the electrically insulated balloon, while inflated within the portion of the biological lumen, reduces and preferably prevents the stimulation energy or a portion thereof from traveling through blood (which is electrically conductive) within the biological lumen (e.g., a renal artery) directly from the distal electrode to the proximal electrode, and/or vice versa. Beneficially, such an embodiment should provide for an improved signal-to-noise ratio (SNR) of the sensed evoked neural response signal by allowing more of the stimulation energy to travel via the nerves or neural tissue, compared to if there was no electrically insulated balloon between the distal electrode (e.g., 903, 1203, 1303, 1403 or 1503) and the proximal electrode (e.g., 905, 1205, 1305, 1405 or 1505).

Methods according to certain embodiments of the present technology will now be described below with reference to the high level flow diagram of FIG. 17. Such methods are for use with a catheter (e.g., 102) including a handle (e.g., 220), a shaft (e.g., 214) extending from the handle, a selectively inflatable balloon (e.g., 112) located on the shaft, and a distal electrode (e.g., 903, 1203, 1303, 1403, 1503 or 1603) and a proximal electrode (e.g., 905, 1205, 1305, 1405, 1505 or 1605) longitudinally spaced apart from one another. In certain embodiments, the catheter also includes a transducer (e.g., 111) located within the selectively inflatable balloon. Examples of such a catheter were described above. Where the steps summarized with reference to FIG. 17 can be performed using a single catheter, without requiring any catheter exchanges (aka swaps), the catheter can be referred to as an all-in-one catheter. Example details of such an all-in-one catheter, according to various difference embodiments of the present technology, can be appreciated from the above discussion of FIGS. 1-16.

Figure 17:
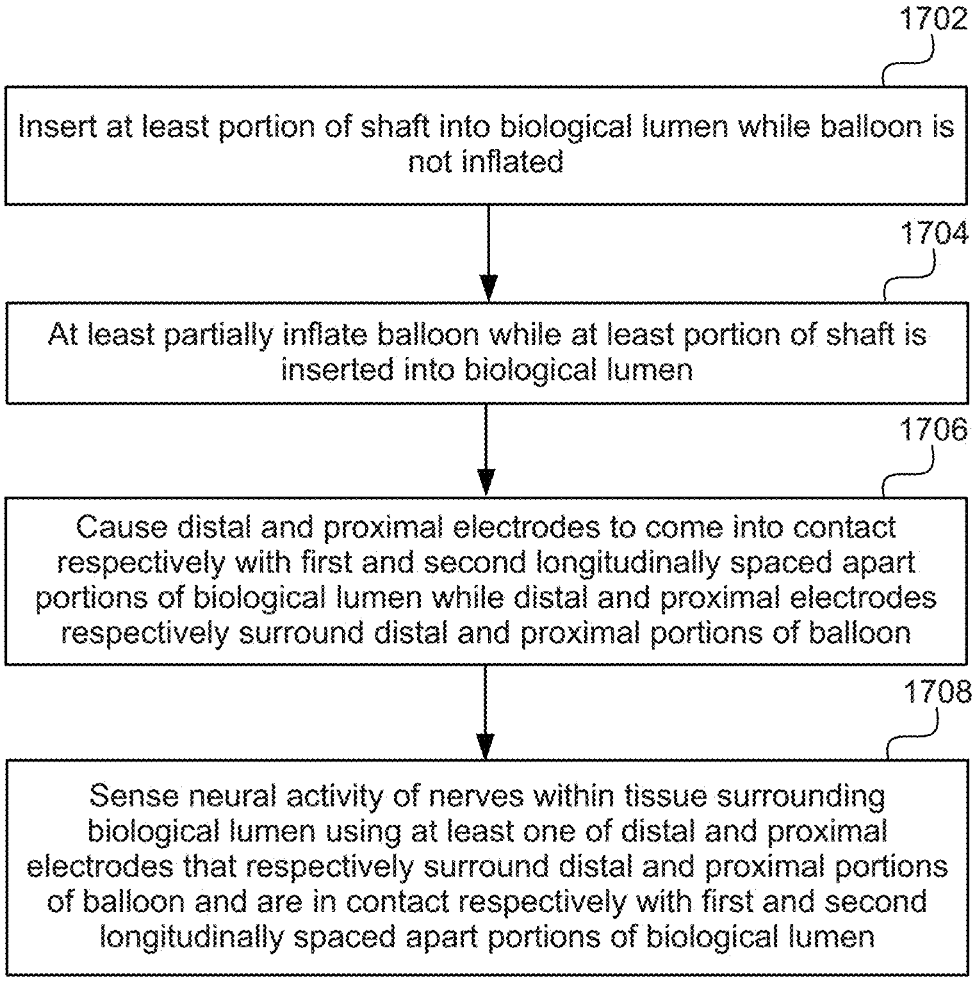
FIG. 17 is a high level flow diagram that is used to summarize methods according to various embodiments of the present technology.

Referring to FIG. 17, step 1702 involves inserting at least a portion of the shaft into a biological lumen (e.g., a renal artery, but not limited thereto) while the balloon is not inflated. Step 1704 involves at least partially inflating the balloon while the at least the portion of the shaft is inserted into the biological lumen. Step 1704 can be performed by at least partially filling the balloon with a cooling fluid, e.g., using the cooling fluid supply subsystem (e.g., 428 or 728, but not limited thereto) and one or more fluid lumens (e.g., 327 and 328, but not limited thereto) in the shaft of the catheter. Step 1706 involves causing the distal and proximal electrodes to come into contact respectively with first and second longitudinally spaced apart portions of the biological lumen while the distal and proximal electrodes respectively surround distal and proximal portions of the balloon. Step 1708 involves sensing neural activity of nerves (e.g., renal nerves, but not limited thereto) within tissue surrounding the biological lumen using at least one of the distal and proximal electrodes that respectively surround the distal and proximal portions of the balloon and are in contact respectively with the first and second longitudinally spaced apart portions of the biological lumen.

The neural activity that is sensed at step 1708, using at least one of the distal and proximal electrodes, can be native neural activity. Alternatively, or additionally, evoked neural activity can be sensed. More specifically, the method can also include delivering stimulation energy using one of the distal and proximal electrodes, in which case the neural activity sensed at step 1708 can be an evoked neural response to the stimulation energy.

As explained above, the shaft of the catheter can also include one or more further electrodes (e.g., non-deployable ring electrodes and/or a tip electrode) that is/are located on a portion of the shaft that does not include the balloon. In such an embodiment, the stimulation energy can also be delivered using at least one of the one or more further electrodes (e.g., a ring electrode or a tip electrode). The neural activity that is sensed can also be sensed using at least one of the one or more further electrodes (e.g., a ring electrode or a tip electrode).

As explained above, the shaft of the catheter can also include a transducer (e.g., 111) within the balloon (112). In such an embodiment, the method can also include energizing the transducer, to thereby treat tissue surrounding the biological lumen, wherein the energizing is performed before and/or after sensing the neural activity of the nerves within the tissue surrounding the biological lumen. In certain such embodiments, prior to delivering the stimulation energy using the one of the distal and proximal electrodes, and prior to sensing the evoked neural response to the stimulation energy using the other one of the distal and proximal electrodes, the method can include selectively transitioning each of the distal and proximal electrodes (e.g., 903 and 905) between a non-intussuscepted position (e.g., shown in FIG. 9B) and an intussuscepted position (e.g., shown in FIG. 9C) and thereby causing the distal and proximal electrodes to come into contact respectively with the first and second longitudinally spaced apart portions of the biological lumen. Then, after delivering the stimulation energy using the one of the distal and proximal electrodes, and sensing the evoked neural response to the stimulation energy using the other one of the distal and proximal electrodes, the method can include selectively transitioning each of the distal and proximal electrodes between the intussuscepted position and the non-intussuscepted position. The method can further include, while each of the distal and proximal electrodes is in the intussuscepted position, performing the energizing the transducer to thereby treat the tissue surrounding the biological lumen. Beneficially, when the electrodes (e.g., 903, 905) are in their non-intussuscepted positions, the electrodes do not block or otherwise adversely affect the emission pattern of the transducer, as was explained above.

In certain embodiments described above, the distal electrode comprises a distal spiral electrode (e.g., 1203) at least partially encircling a distal portion of the balloon, and the proximal electrode comprises a proximal spiral electrode (e.g., 1205) at least partially encircling a proximal portion of the balloon. In certain such embodiments, selectively transitioning each of the distal and proximal spiral electrodes between a non-deployed position and a deployed position occurs in response to the balloon being at least partially inflated while the at least the portion of the shaft is inserted into the biological lumen, as was described above with reference to FIG. 12. As was also described above with reference to FIG. 12, such distal and proximal spiral electrodes can be made from an electrically conductive material having shape memory (e.g., Nitinol), in which case selectively transitioning each of the distal and proximal spiral electrodes between the non-deployed position and the deployed position comprises partially unwinding each of the distal and proximal spiral electrodes in response to the balloon being at least partially inflated. Further, in such an embodiment, the method can also include relying on the shape memory to cause each of the distal and proximal spiral electrodes to rewind in response to the balloon being deflated, after the balloon had been at least partially inflated.

In certain embodiments, such as those described above with reference to FIGS. 13, 14A-14C, 15 and 16, the distal and proximal electrodes are located on and/or attached to the balloon. In certain such embodiments, causing the distal and proximal electrodes to come into contact respectively with the first and second longitudinally spaced apart portions of the biological lumen occurs at step 1706 in response to, and simultaneously with, at least partially inflating the balloon at step 1704 while the at least the portion of the shaft is inserted into the biological lumen. In other words, steps 1704 and 1706 can be performed simultaneously, in which case they can be considered sub-steps of the same step. Additional and alternative details of the methods summarized above with reference to FIG. 17 can be appreciated from the above description of FIGS. 1-16.

The transducers, apparatuses, systems, and methods described herein may be used to treat any suitable tissue, which tissue may be referred to as a target anatomical structure. For example, use of the present systems to treat (e.g., neuromodulate) the renal nerve is described above. It should be appreciated that body lumens, in which the present systems may be positioned for treating tissue, are not necessarily limited to naturally occurring body lumens. For example, the treatment may include creating a body lumen within tissue (e.g., using drilling, a cannula, laser ablation, or the like) and then positioning suitable components within such a body lumen. Other suitable applications for the present system include ablation of pulmonary nerve and tissue responsible veins or cardiac arrhythmia, nerves within that intervertebral disk, nerves within or outside of that intervertebral disk, basivertebral nerves within that vertebral bone, nerves within the brain tissue, tissue responsible for cardiac arrhythmia within the cardiac tissue, nerves along the bronchial tree, one or more esophageal branches of the vagus nerve, and one or more nerves surrounding the bladder.

Advantages of embodiments of the current disclosure include: 1) The ability to determine the appropriate lesion sites along the artery that correspond to the location of nerves; 2) The ability to verify that the destructive devices are appropriately positioned adjacent to the arterial wall, normalizing the tissue/device interface and enabling energy transfer through the vessel wall; and 3) The ability to provide feedback to the clinician intraoperatively to describe lesion completeness or the integrity of the affected nerve fibers.

EXAMPLES

Example 1. A catheter for use in analyzing neural activity of nerves that surround a biological lumen, the catheter comprising: a handle; and a shaft extending from the handle and configured to be inserted into the biological lumen; a selectively inflatable balloon located on the shaft; and a distal electrode and a proximal electrode longitudinally spaced apart from one another on the shaft; wherein each of the distal electrode and the proximal electrode is configured to be selectively transitioned between a non-intussuscepted position and an intussuscepted position.

Example 2. The catheter of example 1, wherein: the distal electrode is distal to the balloon when the distal electrode is in the non-intussuscepted position; the proximal electrode is proximal to the balloon when the proximal electrode is in the non-intussuscepted position; the distal electrode at least partially overlaps a distal portion of the balloon when the distal electrode is in the intussuscepted position; and the proximal electrode at least partially overlaps a proximal portion of the balloon when the proximal electrode is in the intussuscepted position.

Example 3. The catheter of example 1, wherein: the distal and proximal electrodes are configured to come into contact respectively with first and second longitudinally spaced apart portions of the biological lumen when the shaft is inserted into the biological lumen, the balloon is at least partially inflated, and the distal and proximal electrodes are each in the intussuscepted position; and the balloon is configured to create an insulating layer between the distal electrode and the proximal electrode. This can be achieved at least in part by restricting blood from flowing through the biological lumen from a first location adjacent the distal electrode to a second location adjacent the proximal electrode, and/or vice versa.

Example 4. The catheter of example 3, wherein: at least one of the distal and proximal electrodes is configured to be used to sense neural activity of the nerves that surround the biological lumen.

Example 5. The catheter of example 3, wherein: at least one of the distal and proximal electrodes is configured to be used to stimulate the nerves that surround the biological lumen to thereby evoke a neural response.

Example 6. The catheter of example 3, further comprising: at least one of a non-deployable ring electrode or a tip electrode on the shaft, which can be used together with one or both of the distal and proximal electrodes to sense neural activity of the nerves that surround the biological lumen and/or to stimulate the nerves that surround the biological lumen to thereby evoke a neural response.

Example 7. The catheter of example 1, wherein the handle includes: a first actuator configured to transition the distal electrode between the non-intussuscepted position and the intussuscepted position; and a second actuator configured to transition the proximal electrode between the non-intussuscepted position and the intussuscepted position.

Example 8. The catheter of example 1, further comprising: a transducer within the balloon; wherein the transducer is configured to be selectively energized to treat tissue surrounding the biological lumen; and wherein the balloon is configured to be at least partially filled with a cooling fluid to thereby cool the transducer and/or the tissue surrounding the biological lumen.

Example 9. The catheter of example 8, wherein: the transducer comprises an ultrasound transducer.

Example 10. The catheter of example 8, wherein: the shaft includes a fluid lumen configured to inject fluid into the balloon.

Example 11. A catheter for use in analyzing neural activity of nerves that surround a biological lumen, the catheter comprising: a handle; and a shaft extending from the handle and configured to be inserted into the biological lumen; a selectively inflatable balloon located on the shaft; a distal spiral electrode at least partially encircling a distal portion of the balloon; and a proximal spiral electrode at least partially encircling a proximal portion of the balloon; wherein each of the distal and proximal spiral electrodes is configured to be selectively transitioned between a non-deployed and a deployed position in response to the balloon being at least partially inflated.

Example 12. The catheter of example 11, wherein: each of the distal and proximal spiral electrodes is made from an electrically conductive material having shape memory; each of the distal and proximal spiral electrodes partially unwind in response to the balloon being at least partially inflated; and the shape memory of the distal and proximal spiral electrodes causes each of the distal and proximal spiral electrodes to rewind in response to the balloon being deflated, after the balloon had been at least partially inflated.

Example 13. The catheter of example 11, wherein: the distal and proximal spiral electrodes are configured to come into contact respectively with first and second longitudinally spaced apart portions of the biological lumen when the shaft is inserted into the biological lumen, the balloon is at least partially inflated, and the distal and proximal electrodes are each expanded in diameter; and the balloon is configured to create an insulating layer between the distal electrode and the proximal electrode. This can be achieved at least in part by the balloon restricting blood from flowing through the biological lumen from a first location adjacent the distal electrode to a second location adjacent the proximal electrode, and/or vice versa.

Example 14. The catheter of example 13, wherein: at least one of the distal and proximal spiral electrodes is configured to be used to sense neural activity of the nerves that surround the biological lumen.

Example 15. The catheter of example 13, wherein: at least one of the distal and proximal spiral electrodes is configured to be used to stimulate the nerves that surround the biological lumen to thereby evoke a neural response.

Example 16. The catheter of example 13, further comprising: at least one of a non-deployable ring electrode or a tip electrode on the shaft, which can be used together with one or both of the distal and proximal spiral electrodes to sense neural activity of the nerves that surround the biological lumen and/or to stimulate the nerves that surround the biological lumen to thereby evoke a neural response.

Example 17. The catheter of example 11, further comprising: a net that at least partially surrounds the balloon and each of the distal and proximal spiral electrodes to thereby hold the distal and proximal spiral electrodes in place relative to the balloon.

Example 18. The catheter of example 11, wherein: the balloon is made from two layers of non-electrically conductive material including an innermost layer and an outermost layer; one or more portions of each of the distal and proximal spiral electrodes are sandwiched between the two layers of non-electrically conductive material from which the balloon is made; and one or more further portions of each of the distal and proximal spiral electrodes are exposed where the outermost layer has been removed.

Example 19. The catheter of example 11, further comprising: a transducer within the balloon; wherein the transducer is configured to be selectively energized to treat tissue surrounding the biological lumen; and wherein the balloon is configured to be at least partially filled with a cooling fluid to thereby cool the transducer and/or the tissue surrounding the biological lumen.

Example 20. The catheter of example 19, wherein: the transducer comprises an ultrasound transducer.

Example 21. A catheter for use in analyzing neural activity of nerves that surround a biological lumen, the catheter comprising: a handle; and a shaft extending from the handle and configured to be inserted into the biological lumen; a selectively inflatable balloon located on the shaft and made for a non-electrically conductive material; and a distal coated electrode formed on and encircling a circumference of a distal portion of the balloon; a proximal coated electrode formed on and encircling a circumference of a proximal portion of the balloon.

Example 22. The catheter of example 21, wherein: each of the distal and proximal coated electrodes is provided by deposition, printing, or painting via masking.

Example 23. The catheter of example 21, wherein: the distal and proximal coated electrodes are configured to come into contact respectively with first and second longitudinally spaced apart portions of the biological lumen when the shaft is inserted into the biological lumen and the balloon is at least partially inflated; and the balloon is configured to create an insulating layer between the distal electrode and the proximal electrode. This can be achieved at least in part by the balloon restricting blood from flowing through the biological lumen from a first location adjacent the distal coated electrode to a second location adjacent the proximal coated electrode, and/or vice versa.

Example 24. The catheter of example 23, wherein: at least one of the distal and proximal coated electrodes is configured to be used to sense neural activity of the nerves that surround the biological lumen.

Example 25. The catheter of example 23, wherein: at least one of the distal and proximal coated electrodes is configured to be used to stimulate the nerves that surround the biological lumen to thereby evoke a neural response.

Example 26. The catheter of example 23, further comprising: at least one of a non-deployable ring electrode or a tip electrode on the shaft, which can be used together with one or both of the distal and proximal coated electrodes to sense neural activity of the nerves that surround the biological lumen and/or to stimulate the nerves that surround the biological lumen to thereby evoke a neural response.

Example 27. The catheter of example 21, wherein: the distal and proximal coated electrodes each comprises at least one of platinum, gold, or silver.

Example 28. The catheter of example 21, further comprising: a transducer within the balloon; wherein the transducer is configured to be selectively energized to treat tissue surrounding the biological lumen; and wherein the balloon is configured to be at least partially filled with a cooling fluid to thereby cool the transducer and/or the tissue surrounding the biological lumen.

Example 29. The catheter of example 28, wherein: the transducer comprises an ultrasound transducer.

Example 30. The catheter of example 28, wherein: the shaft includes a fluid lumen configured to inject fluid into the balloon.

Example 31. A method for use with a catheter including a handle, a shaft extending from the handle, a selectively inflatable balloon located on the shaft, and a distal electrode and a proximal electrode longitudinally spaced apart from one another, the method comprising: inserting at least a portion of the shaft into a biological lumen while the balloon is not inflated; at least partially inflating the balloon while the at least the portion of the shaft is inserted into the biological lumen; causing the distal and proximal electrodes to come into contact respectively with first and second longitudinally spaced apart portions of the biological lumen while the distal and proximal electrodes respectively surround distal and proximal portions of the balloon; and sensing neural activity of nerves within tissue surrounding the biological lumen using at least one of the distal and proximal electrodes that respectively surround the distal and proximal portions of the balloon and are in contact respectively with the first and second longitudinally spaced apart portions of the biological lumen.

Example 32. The method of example 31, wherein: the neural activity that is sensed using at least one of the distal and proximal electrodes comprises native neural activity.

Example 33. The method of example 31, further comprising: delivering stimulation energy using one of the distal and proximal electrodes; and the sensing neural activity of nerves within tissue surrounding the biological lumen comprises sensing an evoked neural response to the stimulation energy using the other one of the distal and proximal electrodes.

Example 34. The method of example 33, wherein: the shaft also includes one or more further electrodes located on a portion of the shaft that does not include the balloon; and the delivering the stimulation energy is performed also using at least one of the one or more further electrodes.

Example 35. The method of example 34, wherein: the sensing the neural activity is performed also using at least one of the one or more further electrodes.

Example 36. The method of example 31, wherein the shaft also includes a transducer within the balloon, and the method further comprising: energizing the transducer, to thereby treat tissue surrounding the biological lumen, wherein the energizing is performed at least one of before or after the sensing the neural activity of the nerves within the tissue surrounding the biological lumen.

Example 37. The method of example 36, further comprising: prior to delivering the stimulation energy using the one of the distal and proximal electrodes, and prior to sensing the evoked neural response to the stimulation energy using the other one of the distal and proximal electrodes, selectively transitioning each of the distal and proximal electrodes between a non-intussuscepted position and an intussuscepted position and thereby causing the distal and proximal electrodes to come into contact respectively with the first and second longitudinally spaced apart portions of the biological lumen; after delivering the stimulation energy using the one of the distal and proximal electrodes, and sensing the evoked neural response to the stimulation energy using the other one of the distal and proximal electrodes, selectively transitioning each of the distal and proximal electrodes between the intussuscepted position and the non-intussuscepted position; and while each of the distal and proximal electrodes is in the intussuscepted position, performing the energizing the transducer to thereby treat the tissue surrounding the biological lumen.

Example 38. The method of example 36, wherein the distal electrode comprises a distal spiral electrode at least partially encircling the distal portion of the balloon, the proximal electrode comprises a proximal spiral electrode at least partially encircling the proximal portion of the balloon, and the method further comprises: selectively transitioning each of the distal and proximal spiral electrodes between a non-deployed position and a deployed position in response to the at least partially inflating the balloon while the at least the portion of the shaft is inserted into the biological lumen.

Example 39. The method of example 38, wherein each of the distal and proximal spiral electrodes is made from an electrically conductive material having shape memory, and wherein: the selectively transitioning each of the distal and proximal spiral electrodes between the non-deployed position and the deployed position comprises partially unwinding each of the distal and proximal spiral electrodes in response to the balloon being at least partially inflated; and the shape memory causing each of the distal and proximal spiral electrodes to rewind in response to the balloon being deflated, after the balloon had been at least partially inflated.

Example 40. The method of example 31, wherein: the distal and proximal electrodes are at least one of located on or attached to the balloon; and the causing the distal and proximal electrodes to come into contact respectively with first and second longitudinally spaced apart portions of the biological lumen occurs in response to, and simultaneously with, the at least partially inflating the balloon while the at least the portion of the shaft is inserted into the biological lumen.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are example embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

Although several embodiments and examples are disclosed herein, the present application extends beyond the specifically disclosed embodiments to other alternative embodiments and/or uses of the technologies and modifications and equivalents thereof. It is also contemplated that various combinations or subcombinations of the specific features and aspects of the embodiments may be made and still fall within the scope of the technologies. Accordingly, it should be understood that various features and aspects of the disclosed embodiments can be combined with or substituted for one another in order to form varying modes of the disclosed technologies. Thus, it is intended that the scope of the present technologies herein disclosed should not be limited by the particular disclosed embodiments described above, but should be determined only by a fair reading of the claims that follow.

While the technologies are susceptible to various modifications, and alternative forms, specific examples thereof have been shown in the drawings and are herein described in detail. It should be understood, however, that the technologies are not to be limited to the particular forms or methods disclosed, but, to the contrary, the technologies are to cover all modifications, equivalents, and alternatives falling within the spirit and scope of the various embodiments described and the appended claims. Any methods disclosed herein need not be performed in the order recited.

What is claimed is:

1. A catheter for use in analyzing neural activity of nerves that surround a biological lumen, the catheter comprising:
- a handle; and
- a shaft extending from the handle and configured to be inserted into the biological lumen;
- a selectively inflatable balloon located on the shaft; and
- a distal electrode and a proximal electrode longitudinally spaced apart from one another on the shaft;
- wherein each of the distal electrode and the proximal electrode is configured to be selectively transitioned between a non-intussuscepted position and an intussuscepted position.

2. The catheter of claim 1, wherein:
- the distal electrode is distal to the balloon when the distal electrode is in the non-intussuscepted position;
- the proximal electrode is proximal to the balloon when the proximal electrode is in the non-intussuscepted position;
- the distal electrode at least partially overlaps a distal portion of the balloon when the distal electrode is in the intussuscepted position; and
- the proximal electrode at least partially overlaps a proximal portion of the balloon when the proximal electrode is in the intussuscepted position.

3. The catheter of claim 1, wherein:
- the distal and proximal electrodes are configured to come into contact respectively with first and second longitudinally spaced apart portions of the biological lumen when the shaft is inserted into the biological lumen, the balloon is at least partially inflated, and the distal and proximal electrodes are each in the intussuscepted position; and
- the balloon is configured to create an insulating layer between the distal electrode and the proximal electrode.

4. The catheter of claim 3, wherein:
- at least one of the distal and proximal electrodes is configured to be used to sense neural activity of the nerves that surround the biological lumen.

5. The catheter of claim 3, wherein:
- at least one of the distal and proximal electrodes is configured to be used to stimulate the nerves that surround the biological lumen to thereby evoke a neural response.

6. The catheter of claim 3, further comprising:
- at least one of a non-deployable ring electrode or a tip electrode on the shaft, which can be used together with one or both of the distal and proximal electrodes to at least one of sense neural activity of the nerves that surround the biological lumen or stimulate the nerves that surround the biological lumen to thereby evoke a neural response.

7. The catheter of claim 1, wherein the handle includes:
- a first actuator configured to transition the distal electrode between the non-intussuscepted position and the intussuscepted position; and
- a second actuator configured to transition the proximal electrode between the non-intussuscepted position and the intussuscepted position.

8. The catheter of claim 1, further comprising:
- a transducer within the balloon;
- wherein the transducer is configured to be selectively energized to treat tissue surrounding the biological lumen; and
- wherein the balloon is configured to be at least partially filled with a cooling fluid.

9. The catheter of claim 8, wherein:
- the transducer comprises an ultrasound transducer.

10. The catheter of claim 8, wherein:
- the shaft includes a fluid lumen configured to inject the cooling fluid into the balloon.

* * * * *